US008378081B2

(12) United States Patent
Matsubara et al.

(10) Patent No.: US 8,378,081 B2
(45) Date of Patent: Feb. 19, 2013

(54) ANTIBODIES THAT SPECIFICALLY BIND TO Aβ OLIGOMERS AND USES THEREOF

(75) Inventors: Etsuro Matsubara, Aomori (JP); Masao Shibata, Nagano (JP); Tatsuki Yokoseki, Kanagawa (JP)

(73) Assignees: Immunas Pharma, Inc., Kanagawa (JP); National Center for Geriatrics and Gerontology, Aichi (JP)

( * ) Notice: Subject to any disclaimer, the term of this patent is extended or adjusted under 35 U.S.C. 154(b) by 75 days.

(21) Appl. No.: 12/533,348

(22) Filed: Jul. 31, 2009

(65) Prior Publication Data

US 2010/0028357 A1   Feb. 4, 2010

Related U.S. Application Data

(63) Continuation-in-part of application No. PCT/JP2009/052039, filed on Feb. 6, 2009.

(60) Provisional application No. 61/085,545, filed on Aug. 1, 2008.

(30) Foreign Application Priority Data

Feb. 8, 2008   (JP) ................................. 2008-028386
Aug. 4, 2008   (JP) ................................. 2008-201058

(51) Int. Cl.
 *C07K 16/18* (2006.01)
 *C12P 21/08* (2006.01)
 *A61K 39/395* (2006.01)
(52) U.S. Cl. ................. 530/387.3; 530/388.1; 424/141.1
(58) Field of Classification Search ........................ None
See application file for complete search history.

(56) References Cited

U.S. PATENT DOCUMENTS

| | | | |
|---|---|---|---|
| 6,218,506 B1 | 4/2001 | Krafft et al. | |
| 6,706,487 B1 * | 3/2004 | Abdel-Meguid et al. | ...... 435/7.1 |
| 7,339,035 B2 | 3/2008 | Yanagisawa et al. | |
| 7,638,283 B2 | 12/2009 | Krafft et al. | |
| 7,741,448 B2 | 6/2010 | Yanagisawa et al. | |
| 2003/0068316 A1 | 4/2003 | Klein et al. | |
| 2006/0228349 A1 | 10/2006 | Acton et al. | |
| 2006/0257396 A1 * | 11/2006 | Jacobsen | .................... 424/141.1 |
| 2007/0098721 A1 | 5/2007 | Hillen et al. | |
| 2007/0218499 A1 * | 9/2007 | Lambert et al. | ................. 435/7.1 |
| 2010/0183611 A1 * | 7/2010 | Imboden et al. | ............ 424/134.1 |
| 2010/0260783 A1 | 10/2010 | Matsubara et al. | |
| 2010/0291071 A1 | 11/2010 | Matsubara et al. | |
| 2011/0097319 A1 | 4/2011 | Matsubara et al. | |

FOREIGN PATENT DOCUMENTS

| | | | |
|---|---|---|---|
| JP | 3512815 B2 | 1/2004 | |
| JP | 2008-527005 A | 7/2008 | |
| WO | WO 00/56771 A1 | 9/2000 | |
| WO | WO 03/004056 A1 | 1/2003 | |
| WO | WO 03/014162 A1 | 2/2003 | |
| WO | WO 03/104437 A2 | 12/2003 | |
| WO | WO 2006/047254 A1 | 5/2006 | |
| WO | WO 2006/055178 A2 | 5/2006 | |
| WO | WO 2006/083533 A2 | 8/2006 | |
| WO | WO 2006/094724 A2 | 9/2006 | |
| WO | WO 2006/137354 A1 | 12/2006 | |
| WO | WO 2007/010040 A1 | 1/2007 | |
| WO | WO 2008/150946 A1 | 12/2008 | |
| WO | WO 2009/051220 A1 | 4/2009 | |
| WO | WO 2009/099176 A1 | 8/2009 | |
| WO | WO 2010/012004 A2 | 1/2010 | |

OTHER PUBLICATIONS

Casset et al. Biochem Biophys Res Comm. 2003; 307:198-205.*
MacCallum et al. J Mol Biol. 1996; 262:732-745.*
Padlan et al. Proc Natl Acad Sci USA, 1989; 86:5938-5942.*
Paul WE, editor. Fundamental Immunology, Third Edition, 1993, pp. 292-295.*
Rudikoff et al. Proc Natl Acad Sci USA, 1982; 79(6):1979-1983.*
Terryberry et al. Neurobiology Aging, 1998; 19(3):205-216.*
Vajdos et al. J Mol Biol. 2002; 320(2):415-428.*
Haass, C., et al., "Soluble protein oligomers in neurodegeneration: lessons from the Alzheimer's amyloid β-peptide," *Nat. Rev. Mol. Cell Bio.* 8:101-112, Nature Publishing Group, England (2007).
Kayed, R., et al., "Common Structure of Soluble Amyloid Oligomers Implies Common Mechanism of Pathogenesis," *Science* 300:486-489, American Association for the Advancement of Science, United States (2003).
Kayed, R., et al., "Fibril specific, conformation dependent antibodies recognize a generic epitope common to amyloid fibrils and fibrillar oligomers that is absent in prefibrillar oligomers," *Mol. Neurodegener.* 2:18, BioMed Central Ltd., England (2007).
Klein, W. L., et al., "Targeting small Aβ oligomers: the solution to an Alzheimer's disease conundrum?" *Trends Neurosci.* 24(4):219-224, Elsevier Inc., England (2001).
Lambert, M. P., et al., "Vaccination with soluble oligomers generates toxicity-neutralizing antibodies," *J. Neurochem.* 79: 595-605, International Society for Neurochemisty, England (2001).
Lambert, M. P., et al., "Monoclonal antibodies that target pathological assemblies of Aβ," *J. Neurochem.* 100:23-25, International Society for Neurochemistry, England (2007).
Lee, E. B., et al., "Targeting Amyloid-β Peptide (Aβ) Oligomers by Passive Immunization with a Conformation-selective Monoclonal Antibody Improves Learning and Memory in Aβ Precursor Protein (APP) Transgenic Mice," *J. Biol. Chem.* 281: 4292-4299, American Society for Biochemistry and Molecular Biology, United States (2006).

(Continued)

*Primary Examiner* — Elizabeth C Kemmerer
*Assistant Examiner* — Kimberly A Ballard
(74) *Attorney, Agent, or Firm* — Sterne, Kessler, Goldstein & Fox P.L.L.C.

(57) ABSTRACT

The present inventors successfully produced monoclonal antibodies that are specific to only soluble Aβ oligomers, but do not recognize soluble Aβ monomers, which are physiological molecules. It was demonstrated that the antibodies are useful as diagnostic/therapeutic monoclonal antibodies for Alzheimer's disease.

4 Claims, 18 Drawing Sheets

OTHER PUBLICATIONS

Lesné, S., et al., "A specific amyloid-β protein assembly in the brain impairs memory," *Nature* 440:352-357, Nature Publishing Group, England (2006).

Matsubara, E., et al., "Development of a diagnosing system for Alzheimer' disease using anti-Aβ oligomer antibodies," Abstract 1-2-9, The 46th Annual Meeting of Japanese Society of Neurology, Kagoshima, Japan, May 25-27, 2005.

Matsubara, Etsuro, "Aβ oligomers," *Dementia Japan* 21:253-259, Japan (2007).

Matsubara, Etsuro, "Immunotherapy targeting Aβ oligomers for Alzheimer's disease," Abstract S31-2 and presentation, 8th Asia/Oceania Regional Congress of Gerontology and Geriatrics, Beijing, China, Oct. 22, 2007.

Matsubara, Etsuro, "Passive immunotherapy Aβ oligomer in Alzheimer's disease," Abstract S38-4, 128th Annual Meeting of the Pharmaceutical Society of Japan, Yokohama, Japan, Mar. 26-28, 2008.

Matsubara, Etsuro, "The Aβ-oligomer specific passive immunization in Alzheimer's disease," 128th Annual Meeting of the Pharmaceutical Society of Japan, Yokohama, Japan, Feb. 1, 2007.

Matsubara, Etsuro, "Neurotoxic Aβ oligomer being the basis of developmental pathology of Alzheimer's disease," Abstract SY-2-2, The 49th Annual Meeting of Japanese Society of Neurology, Yokohama, Japan, Apr. 25, 2008.

Matsubara, Etsuro, "The Aβ-oligomer specific passive immunization in Alzheimer's disease," The 49th Annual Meeting of Japanese Society of Neurology, Yokohama, Japan, May 16, 2008.

Moretto, N., et al., "Conformation-sensitive Antibodies against Alzheimer Amyloid-β by Immunization with a Thioredoxin-constrained B-cell Epitope Peptide," *J. Biol. Chem.* 282:11436-11445, American Society for Biochemistry and Molecular United States (2007).

Selkoe, Dennis J., "Alzheimer's Disease Is a Syiaptic Failure," *Science* 298:789-791, American Association for the Advancement of Science, United States (2002).

Shoji, M., et al., "Investigation on pathogenicity of Aβ peptide and development of pathogenic Aβ oligomer removal therapy," Health and Labour Sciences ResearchA Grants (Research on specified diseases), pp. 68-72 (2004).

Shoji, M., et al., "Antibody therapy for Alzheimer's disease," Health and Labour Sciences Research Grants, Study and research group on amyloidosis, pp. 76-78 (2008).

Sun, H., et al., "Characterization of therapeutic antibody against Aβ oligomers for Alzheimers disease," *Dementia Japan* 21:183, Abstract p. 2-261, Japan (2007).

Sun, H., et al., "Characterization of therapeutic antibody against Aβ oligomers for Alzheimer's disease," The 26th Annual Meeting of Japan Society for Dementia Research, Oct. 17-18, 2007.

Sun, H., et al., "Characterization of therapeutic antibody against Aβ oligomers for Alzheimer's disease," Abstract, Neuroscience 2007, San Diego, United States, Aug. 16, 2007.

Sun, H., et al., "Characterization of therapeutic antibody against Aβ oligomers for Alzheimer's disease," Poster 485.15/W10, Neuroscience 2007, San Diego, United States, Nov. 5, 2007.

Unverified English language of Matsubara, E., et al., "Development of a diagnosing system for Alzheimer' disease using anti-Aβ oligomer antibodies," Abstract 1-2-9, The 46th Annual Meeting of Japanese Society of Neurology, Kagoshima, Japan, May 25-27, 2005.

Unverified English language translation of Abstract of Matsubara, Etsuro, "Aβ oligomers," *Dementia Japan* 21:253-259, Japan (2007).

Unverified English language translation of Matsubara, Etsuro, "Passive immunotherapy Aβ oligomer in Alzheimer's disease," Abstract S38-4, 128th Annual Meeting of the Pharmaceutical Sociery of Japan, Yokohama, Japan, Mar. 26-28, 2008.

Unverified English language translation of Matsubara, Etsuro, "The Aβ-oligomer specific passive immunization in Alzheimer's disease," 128th Annual Meeting of the Pharmaceutical Society of Japan, Yokohama, Japan, Mar. 28, 2008.

Unverified English language translation of Matsubara, Etsuro, "Neurotoxic Aβ oligomer being the basis of developmental pathology of Alzheimer's disease," Abstract SY-2-2, The 49th Annual Meeting of Japanese Society of Neurology, Yokohama, Japan, May 15-17, 2008.

Unverified English language translation of Matsubara, Etsuro, "The Aβ-oligomer specific passive immunization in Alzheimer's disease," The 49th Annual Meeting of Japanese Society of Neurology, Yokohama, Japan, May 16, 2008.

Unverified English language translation of Shoji, M., et al., "Investigation on pathogenicity of Aβ peptide and development of pathogenic Aβ oligomer removal therapy," Health and Labour Sciences ResearchA Grants (Research on specified diseases), pp. 68-72 (2004).

Unverified English language translation of Shoji, M., et al., "Antibody therapy for Alzheimer's disease," Health and Labour Sciences Research Grants, Study and research group on amyloidosis, pp. 76-78 (2008).

Co-pending U.S. Appl. No. 12/851,233, inventors Matsubara, E., et al., filed Aug. 5, 2010 (Not Yet Published).

Office Action mailed Apr. 13, 2011, in U.S. Appl. No. 12/533,294, inventors Matsubara, E., et al., filed Jul. 31, 2009, U.S. Patent and Trademark Office, Alexandria, VA.

Brookmeyer, R. et al., "Forecasting the global burden of Alzheimer's disease," *Alzheimer's & Dementia* 3:186-191, The Alzheimer's Association (2007).

Ma, Q.-L. et al., "Antibodies Against β-Amyloid Reduce Aβ Oligomers, Glycogen Synthase Kinase-3β Activation and τ Phosphorylation In Vivo and In Vitro," *J. Neurosci. Res.* 83:374-384, Wiley-Liss, Inc. (2006).

Wang, X.-p. et al., "Conformation-dependent single-chain variable fragment antibodies specifically recognize beta-amyloid oligomers," *FEBS Letts.* 583:579-584, Elsevier B.V. (2009).

Office Action mailed Jan. 19, 2012, in U.S. Appl. No. 12/762,878, inventors Matsubara, E., et al., filed Apr. 19, 2010, U.S. Patent and Trademark Office, Alexandria, VA.

Co-pending Application, U.S. Appl. No. 13/264,671, inventors Yokoseki, T., et al., § 371 Date: Dec. 21, 2011 (Not Yet Published).

Co-pending Application, U.S. Appl. No. 13/389,228, inventors Yokoseki, T., et al., Int'l Filing Date: Aug. 5, 2010 (Not Yet Published).

Co-pending Application, U.S. Appl. No. 13/389,229, inventors Yokoseki, T. et al., Int'l Filing Date: Aug. 5, 2010 (Not Yet Published).

Kayed, R. and Glabe, C.G., "Conformation-Dependent Anti-Amyloid Oligomer Antibodies," *Methods in Enzymol.* 413:326-344, Elsevier Inc. (2006).

Klein, W.L., "Aβ toxicity in Alzheimer's disease: globular oligomers (ADDLs) as new vaccine and drug targets," *Neurochemistry International* 41:345-352, Elsevier Science Ltd. (2002).

Office Action mailed Dec. 27, 2012, in U.S. Appl. No. 13/389,228, inventors Yokoseki, T., et al., filed Feb. 6, 2012, U.S. Patent and Trademark Office, Alexandria, VA.

* cited by examiner

A 1A9-TREATED Tg2576 MICE

Aβ              MOUSE IgG

B 2C3-TREATED Tg2576 MICE

Aβ              MOUSE IgG

C PBS-TREATED Tg2576 MICE

Aβ              MOUSE IgG

ANTIBODIES THAT SPECIFICALLY BIND TO Aβ OLIGOMERS AND USES THEREOF

PRIORITY

The present application claims the benefit of U.S. Provisional Application No. 61/085,545, filed on Aug. 1, 2008, and International patent application No. PCT/JP2009/052039, filed on Feb. 6, 2009, the entire contents of which are incorporated by reference herein.

FIELD OF THE INVENTION

The present invention relates to antibodies that specifically bind to Aβ oligomers and uses thereof.

BACKGROUND OF THE INVENTION

Various evidence has shown that deterioration of memory arises from synaptic dysfunction triggered by soluble Aβ oligomers (see Klein W L, Trends Neurosci. 24: 219-224, 2001; and Selkoe D J, Science 298: 789-791, 2002). Excessive accumulation and deposition of Aβ oligomers may be the trigger for a series of pathological cascades that lead to Alzheimer's disease (AD). Therefore, therapeutic intervention targeting Aβ oligomers may be effective for blocking these cascades. However, findings on core molecules of this amyloid cascade hypothesis which are responsible for neurodegeneration, particularly on neurodegeneration mediated by Aβ oligomers, originate from in vitro experiments (see Hass C et al.: Nature Review 8: 101-12, 2007). This neurodegeneration has not been proven directly in vivo. The greatest defect of previously reported in vivo experiments is that they failed to demonstrate synaptic toxicity of endogenous Aβ oligomers due to the lack of conformation-specific molecular tools (see Lee E B, et al.: J. Biol. Chem. 281: 4292-4299, 2006). There has been known no technique capable of proving the toxicity within the human brain, an aspect which is difficult to demonstrate even in Alzheimer's disease mouse models. Thus, the in vivo neurotoxicity of endogenous Aβ has been often disregarded. It has been unknown why NFT formation and loss of nerve cells precede senile plaque formation in the human entorhinal cortex, and how Aβ oligomers are involved in this mechanism.

SUMMARY OF THE INVENTION

The present invention was achieved in view of the above circumstances. An objective of the present invention is to provide antibodies that bind specifically to Aβ oligomers, and uses thereof. More specifically, the present invention provides antibodies that bind specifically to Aβ oligomers, methods for detecting Aβ oligomers using the antibodies, methods for diagnosing Alzheimer's disease using the antibodies, and pharmaceutical agents comprising the antibodies.

The present inventors produced monoclonal antibodies that are specific to only soluble amyloid β (Aβ) oligomers and do not recognize soluble Aβ monomers which are physiological molecules, and confirmed that the antibodies have the following:
(1) anti-neurotoxic activity;
(2) activity to suppress Aβ amyloid fibril formation;
(3) specificity to recognize only Aβ oligomers;
(4) ability to capture Aβ oligomers in AD brain; and
(5) ability to prevent the development of Alzheimer's disease-like phenotypes (memory impairment, brain Aβ accumulation) in APPswe transgenic mice (Tg2576).

Using an ultrafiltration/molecular sieve method, among the antibodies produced, monoclonal 1A9 and 2C3 were determined to specifically recognize oligomers of 30 kDa or more, mainly 100 kDa or more, but not monomers of approximately 4.5 kDa. The two antibodies were confirmed to have neurotoxicity-neutralizing activity by evaluating the neutralizing effect against Aβ 1-42-induced neurotoxicity in PC12 cells differentiated into nerve cells. Thioflavin T assay and electron microscopy showed that the antibodies have activity to suppress Aβ amyloid fibril formation. The ability of 1A9 and 2C3 to capture Aβ oligomers in AD brain was confirmed by immunoprecipitation using the antibodies in the presence of SDS-stable 4-, 5-, 8-, and 12-mers. Furthermore, to determine the in vivo neurotoxicity in the human brain, the amount of polymers recognized by the antibodies was evaluated in the human entorhinal cortex mostly at Braak NFT Stages I to III. By particularly focusing on the 12-mer, which has been reported to have neurotoxicity in animal studies, it was confirmed that the polymer accumulation precedes the occurrence of cognitive impairment, and is increased with the progression of Braak NFT stage. This result shows for the first time that the 12-mer, which is specifically recognized by the antibodies, is a conformational assembly that causes in vivo neurotoxicity in the human brain. The present inventors also discovered that the oligomeric conformational structure recognized by the antibodies is present in cerebrospinal fluid (CSF), and is increased in AD patients. The present inventors used 1A9 or 2C3 in passive immunotherapy by intravenous injection as with other neurological disorders. It was confirmed that Tg2576 mice are protected from memory impairment, senile plaque formation, synaptic dysfunction, and Aβ accumulation by subchronic passive immunotherapy, without harmful side-effects. The results obtained by the present inventors demonstrated for the first time that monoclonal 1A9 and 2C3 are promising candidates for therapeutic antibodies for preventing Alzheimer's disease-like phenotypes in Tg2576 mice, which are expected to show their effect by conventional peripheral intravenous administration, and thus there is no need to consider brain transfer.

The present inventors also confirmed that passive immunotherapy using the 1A9 and 2C3 antibodies suppresses senile plaque amyloid formation and swollen dystrophic neurite formation. Furthermore, the present inventors discovered that a fraction of the 1A9 and 2C3 antibodies administered into the blood transfers into the brain.

As described above, the present inventors disclose herein that monoclonal 1A9 and 2C3, which are antibodies that specifically bind to Aβ oligomers, fulfill all of the diagnostic/therapeutic antibody criteria, and are promising candidates for therapeutic antibodies for diagnosing/preventing Alzheimer's disease.

Furthermore, as with the 1A9 and 2C3 antibodies, the present inventors successfully obtained the 5A5, 5A9, 4F7, 4H5, 6E4, and 6H4 antibodies which bind specifically to Aβ oligomers, but do not recognize Aβ monomers. The present inventors discovered that these six types of antibodies have activity to neutralize Aβ-induced neurotoxicity and to suppress Aβ amyloid fibril formation.

The present inventors disclose that the above-mentioned 5A5, 5A9, 4F7, 4H5, 6E4, and 6H4 antibodies are promising candidates for therapeutic antibodies for diagnosing/preventing Alzheimer's disease.

More specifically, the present invention provides the following:
[1] an antibody binding to an Aβ oligomer that binds to an antibody comprising an H chain having the amino acid sequence of SEQ ID NO: 1 and an L chain having the amino acid sequence of SEQ ID NO: 3;

[2] an antibody binding to an Aβ oligomer that binds to an antibody comprising an H chain having the amino acid sequence of SEQ ID NO: 21 and an L chain having the amino acid sequence of SEQ ID NO: 23;

[3] an antibody binding to an Aβ oligomer that binds to an antibody comprising an H chain having the amino acid sequence of SEQ ID NO: 41 and an L chain having the amino acid sequence of SEQ ID NO: 43;

[4] an antibody binding to an Aβ oligomer that binds to an antibody comprising an H chain having the amino acid sequence of SEQ ID NO: 61 and an L chain having the amino acid sequence of SEQ ID NO: 63;

[5] an antibody binding to an Aβ oligomer that binds to an antibody comprising an H chain having the amino acid sequence of SEQ ID NO: 81 and an L chain having the amino acid sequence of SEQ ID NO: 83;

[6] an antibody binding to an Aβ oligomer that binds to an antibody comprising an H chain having the amino acid sequence of SEQ ID NO: 101 and an L chain having the amino acid sequence of SEQ ID NO: 103;

[7] an antibody of any one of (1) to (38) below:

(1) an antibody that comprises an H chain having the amino acid sequence of SEQ ID NO: 9 as CDR1, the amino acid sequence of SEQ ID NO: 11 as CDR2, and the amino acid sequence of SEQ ID NO: 13 as CDR3;

(2) an antibody that comprises an L chain having the amino acid sequence of SEQ ID NO: 15 as CDR1, the amino acid sequence of SEQ ID NO: 17 as CDR2, and the amino acid sequence of SEQ ID NO: 19 as CDR3;

(3) an antibody that comprises the H chain of (1) and the L chain of (2);

(4) an antibody that comprises an H chain having the amino acid sequence of SEQ ID NO: 5 as VH;

(5) an antibody that comprises an L chain having the amino acid sequence of SEQ ID NO: 7 as VL;

(6) an antibody that comprises the H chain of (4) and the L chain of (5);

(7) an antibody that comprises an H chain having the amino acid sequence of SEQ ID NO: 29 as CDR1, the amino acid sequence of SEQ ID NO: 31 as CDR2, and the amino acid sequence of SEQ ID NO: 33 as CDR3;

(8) an antibody that comprises an L chain having the amino acid sequence of SEQ ID NO: 35 as CDR1, the amino acid sequence of SEQ ID NO: 37 as CDR2, and the amino acid sequence of SEQ ID NO: 39 as CDR3;

(9) an antibody that comprises the H chain of (7) and the L chain of (8);

(10) an antibody that comprises an H chain having the amino acid sequence of SEQ ID NO: 25 as VH;

(11) an antibody that comprises an L chain having the amino acid sequence of SEQ ID NO: 27 as VL;

(12) an antibody that comprises the H chain of (10) and the L chain of (11);

(13) an antibody that comprises an H chain having the amino acid sequence of SEQ ID NO: 49 as CDR1, the amino acid sequence of SEQ ID NO: 51 as CDR2, and the amino acid sequence of SEQ ID NO: 53 as CDR3;

(14) an antibody that comprises an L chain having the amino acid sequence of SEQ ID NO: 55 as CDR1, the amino acid sequence of SEQ ID NO: 57 as CDR2, and the amino acid sequence of SEQ ID NO: 59 as CDR3;

(15) an antibody that comprises the H chain of (13) and the L chain of (14);

(16) an antibody that comprises an H chain having the amino acid sequence of SEQ ID NO: 45 as VH;

(17) an antibody that comprises an L chain having the amino acid sequence of SEQ ID NO: 47 as VL;

(18) an antibody that comprises the H chain of (16) and the L chain of (17);

(19) an antibody that comprises an H chain having the amino acid sequence of SEQ ID NO: 69 as CDR1, the amino acid sequence of SEQ ID NO: 71 as CDR2, and the amino acid sequence of SEQ ID NO: 73 as CDR3;

(20) an antibody that comprises an L chain having the amino acid sequence of SEQ ID NO: 75 as CDR1, the amino acid sequence of SEQ ID NO: 77 as CDR2, and the amino acid sequence of SEQ ID NO: 79 as CDR3;

(21) an antibody that comprises the H chain of (19) and the L chain of (20);

(22) an antibody that comprises an H chain having the amino acid sequence of SEQ ID NO: 65 as VH;

(23) an antibody that comprises an L chain having the amino acid sequence of SEQ ID NO: 67 as VL;

(24) an antibody that comprises the H chain of (22) and the L chain of (23);

(25) an antibody that comprises an H chain having the amino acid sequence of SEQ ID NO: 89 as CDR1, the amino acid sequence of SEQ ID NO: 91 as CDR2, and the amino acid sequence of SEQ ID NO: 93 as CDR3;

(26) an antibody that comprises an L chain having the amino acid sequence of SEQ ID NO: 95 as CDR1, the amino acid sequence of SEQ ID NO: 97 as CDR2, and the amino acid sequence of SEQ ID NO: 99 as CDR3;

(27) an antibody that comprises the H chain of (25) and the L chain of (26);

(28) an antibody that comprises an H chain having the amino acid sequence of SEQ ID NO: 85 as VH;

(29) an antibody that comprises an L chain having the amino acid sequence of SEQ ID NO: 87 as VL;

(30) an antibody that comprises the H chain of (28) and the L chain of (29);

(31) an antibody that comprises an H chain having the amino acid sequence of SEQ ID NO: 109 as CDR1, the amino acid sequence of SEQ ID NO: 111 as CDR2, and the amino acid sequence of SEQ ID NO: 113 as CDR3;

(32) an antibody that comprises an L chain having the amino acid sequence of SEQ ID NO: 115 as CDR1, the amino acid sequence of SEQ ID NO: 117 as CDR2, and the amino acid sequence of SEQ ID NO: 119 as CDR3;

(33) an antibody that comprises the H chain of (31) and the L chain of (32);

(34) an antibody that comprises an H chain having the amino acid sequence of SEQ ID NO: 105 as VH;

(35) an antibody that comprises an L chain having the amino acid sequence of SEQ ID NO: 107 as VL;

(36) an antibody that comprises the H chain of (34) and the L chain of (35);

(37) an antibody that comprises one or more amino acid substitutions, deletions, additions, and/or insertions in the antibody of any one of (1) to (36), which has equivalent activity to the antibody of any one of (1) to (36); and

(38) an antibody that binds to the epitope bound by the antibody of any one of (1) to (36);

[8] the antibody of [7], wherein the antibody is a chimeric antibody or a humanized antibody;

[9] a composition comprising the antibody of any one of [1] to [8] and a pharmaceutically acceptable carrier;

[10] an agent against cognitive impairment, which comprises the antibody of any one of [1] to [8] or the composition of [9] as an active ingredient;

[11] a therapeutic agent for Alzheimer's disease, which comprises the antibody of any one of [1] to [8] or the composition of [9] as an active ingredient;
[12] an agent for suppressing the progression of Alzheimer's disease, which comprises the antibody of any one of [1] to [8] or the composition of [9] as an active ingredient;
[13] an agent for suppressing senile plaque formation, which comprises the antibody of any one of [1] to [8] or the composition of [9] as an active ingredient;
[14] an agent for suppressing Aβ accumulation, which comprises the antibody of any one of [1] to [8] or the composition of [9] as an active ingredient;
[15] an anti-neurotoxic agent, which comprises the antibody of any one of [1] to [8] or the composition of [9] as an active ingredient;
[16] an agent for inhibiting Aβ amyloid fibril formation, which comprises the antibody of any one of [1] to [8] or the composition of [9] as an active ingredient;
[17] an agent against synaptic toxicity, which comprises the antibody of any one of [1] to [8] or the composition of [9] as an active ingredient;
[18] a method for detecting an Aβ oligomer, which comprises the step of detecting an Aβ oligomer contained in a sample collected from a subject using the antibody of any one of [1] to [8];
[19] a method of diagnosing whether or not a subject suffers from or is at a risk of developing Alzheimer's disease, which comprises using the antibody of any one of [1] to [8] to detect an Aβ oligomer in a sample collected from a subject;
[20] a method of diagnosing whether or not a subject suffers from or is at a risk of developing Alzheimer's disease, which comprises the steps of:
(a) contacting a sample collected from a subject with the antibody of any one of [1] to [8]; and
(b) measuring the amount of Aβ oligomer in the sample, wherein the subject is determined to suffer from or be at a risk of developing Alzheimer's disease, when the amount measured in step (b) is higher than that of a healthy individual;
[21] a method of diagnosing whether or not a subject suffers from or is at a risk of developing Alzheimer's disease, which comprises the steps of:
(a) contacting a sample collected from a subject with the antibody of any one of [1] to [8] and an antibody that binds to an Aβ monomer; and
(b) measuring the ratio of Aβ oligomer to Aβ monomer in the sample,
wherein the subject is determined to suffer from or be at a risk of developing Alzheimer's disease, when the ratio measured in step (b) is higher than that of a healthy individual;
[22] the method of any one of [18] to [21], wherein the sample is blood or cerebrospinal fluid;
[23] a pharmaceutical agent for use in the method of any one of [18] to [21]; and
[24] a kit for use in the method of any one of [18] to [21].
Furthermore, the present invention provides the following:
[25] a method for preventing and/or treating cognitive impairment, which comprises the step of administering the antibody of any one of [1] to [8] or the composition of [9] as an active ingredient;
[26] a method for preventing and/or treating Alzheimer's disease, which comprises the step of administering the antibody of any one of [1] to [8] or the composition of [9] as an active ingredient;
[27] a method for suppressing the progression of Alzheimer's disease, which comprises the step of administering the antibody of any one of [1] to [8] or the composition of [9] as an active ingredient;
[28] a method for suppressing senile plaque formation, which comprises the step of administering the antibody of any one of [1] to [8] or the composition of [9] as an active ingredient;
[29] a method for suppressing Aβ accumulation, which comprises the step of administering the antibody of any one of [1] to [8] or the composition of [9] as an active ingredient;
[30] a method for neutralizing neurotoxicity, which comprises the step of administering the antibody of any one of [1] to [8] or the composition of [9] as an active ingredient;
[31] a method for inhibiting Aβ amyloid fibril formation, which comprises the step of administering the antibody of any one of [1] to [8] or the composition of [9] as an active ingredient;
[32] a method for neutralizing synaptic toxicity, which comprises the step of administering the antibody of any one of [1] to [8] or the composition of [9] as an active ingredient;
[33] use of the antibody of any one of [1] to [8] or the composition of [9] in the production of an agent against cognitive impairment;
[34] use of the antibody of any one of [1] to [8] or the composition of [9] in the production of a therapeutic agent for Alzheimer's disease;
[35] use of the antibody of any one of [1] to [8] or the composition of [9] in the production of an agent for suppressing the progression of Alzheimer's disease;
[36] use of the antibody of any one of [1] to [8] or the composition of [9] in the production of an agent for suppressing senile plaque formation;
[37] use of the antibody of any one of [1] to [8] or the composition of [9] in the production of an agent for suppressing Aβ accumulation;
[38] use of the antibody of any one of [1] to [8] or the composition of [9] in the production of an agent for neutralizing (suppressing) neurotoxicity;
[39] use of the antibody of any one of [1] to [8] or the composition of [9] in the production of an agent for inhibiting Aβ amyloid fibril formation;
[40] use of the antibody of any one of [1] to [8] or the composition of [9] in the production of an agent for neutralizing (suppressing) synaptic toxicity;
[41] the antibody of any one of [1] to [8] or the composition of [9] for use in preventing and/or treating cognitive impairment;
[42] the antibody of any one of [1] to [8] or the composition of [9] for use in preventing and/or treating Alzheimer's disease;
[43] the antibody of any one of [1] to [8] or the composition of [9] for use in suppressing the progression of Alzheimer's disease;
[44] the antibody of any one of [1] to [8] or the composition of [9] for use in suppressing senile plaque formation;
[45] the antibody of any one of [1] to [8] or the composition of [9] for use in suppressing Aβ accumulation;
[46] the antibody of any one of [1] to [8] or the composition of [9] for use in neutralizing (suppressing) neurotoxicity;
[47] the antibody of any one of [1] to [8] or the composition of [9] for use in inhibiting Aβ amyloid fibril formation; and
[48] the antibody of any one of [1] to [8] or the composition of [9] for use in neutralizing (suppressing) synaptic toxicity.

BRIEF DESCRIPTION OF THE DRAWINGS

FIG. 7-1 present graphs showing that soluble 1A9- and 2C3-recognized oligomers exist in human CSF. Pooled whole cerebrospinal fluid (CSF) (AD=10 and NC=10) (Panels A and B) and pooled lipoprotein-depleted CSF (AD=10, and NC=10) (Panels C and D) were subjected to size exclusion chromatography (SEC). In Panels A and B, the collected fractions were analyzed for the distribution of Aβ 40 and Aβ 42 monomers by BNT77-BA27 and BNT77-BC05 ELISAs. Panels C and D show the presence of Aβ 40 and Aβ 42 oligomers captured by 1A9/2C3 mixed antibodies.

FIG. 7-2 is the continuation of FIG. 7-1. The amount of 1A9-recognized oligomeric assembly (1A9-BC05 and 1A9-BA27 ELISAs) and the amount of 2C3-recognized assembly (2C3-BC05 and 2C3-BA27 ELISAs) were measured for 12 AD cases (open circle) and 13 NC cases (filled circle) (Panels E and G). The oligomer/monomer ratio is shown in Panels F (1A9) and H (2C3).

Control IgG (3F1), which is an antibody that does not bind to Aβ 42, was used for comparison.

Figure 17:
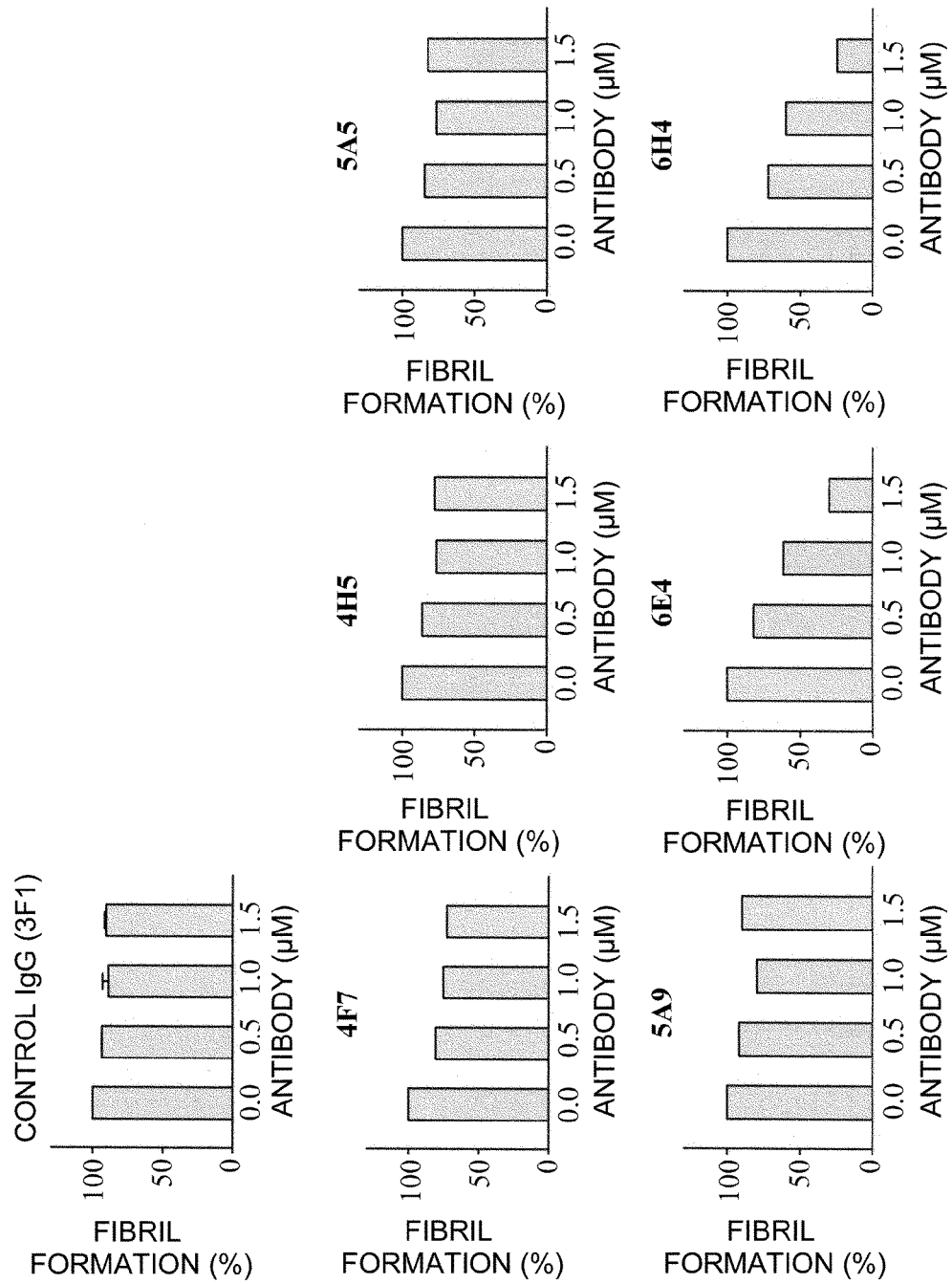

FIG. 17 presents graphs showing the suppressing activity of the six types of antibodies (4F7, 4H5, 5A5, 5A9, 6E4, and 6H4) against Aβ amyloid fibril formation. The antibodies were added at three different concentrations to a Aβ 1-42 solution (12.5 µM). After incubation at 37° C. for 24 hours, the level of Aβ amyloid fibril formation was measured by the ThT fluorescence intensity method. The horizontal axis indicates the amount of antibody added, and the vertical axis shows the level of amyloid fibril formation by the antibody addition that is relative to the level of amyloid fibril formation without antibody addition as the standard.

DETAILED DESCRIPTION OF THE INVENTION

The present invention will be described more specifically below.

As described above, the present inventors succeeded in obtaining antibodies that bind specifically to Aβ oligomers but not to Aβ monomers. That is, the present invention provides antibodies that bind to Aβ oligomers but not to Aβ monomers. The antibodies are preferably isolated or purified.

The terms "isolated" and "purified" used for substances (antibodies and such) of the present invention indicate that the substances do not substantially include at least one other substance that may be contained in the natural source. Therefore, "isolated antibodies" and "purified antibodies" refer to antibodies that do not substantially include cell materials such as hydrocarbons, lipids, or other contaminant proteins from the cell or tissue source from which the antibodies (proteins) are derived. When the antibodies are chemically synthesized, the terms refer to antibodies that do not substantially include chemical precursor substances or other chemical substances. In a preferred embodiment, the antibodies of the present invention are isolated or purified.

"Antibodies" refers to glycoproteins that have the same structural characteristics. Antibodies show binding specificity towards specific antigens. Herein, "antigens" refers to proteins that have the ability to bind to the corresponding antibodies, and induce antigen-antibody reactions in vivo.

Aβ proteins, which are the major constituents of amyloids, are peptides consisting of 40 to 42 amino acids, and are known to be produced from precursor proteins called amyloid precursor proteins (APPs) by the action of proteases. Besides amyloid fibrils collected in ultracentrifuged sediment fractions, the amyloid molecules produced from APPs include oligomeric non-fibrous assemblies in addition to soluble monomers. "Aβ oligomers" of the present invention refer to non-fibrous assemblies. The "Aβ oligomers" of the present invention include, for example, Aβ40 (Aβ 1-40) oligomers and Aβ42 (Aβ 1-42) oligomers. For example, "Aβ42 oligomers" of the present invention are molecules showing a molecular weight of 45 to 160 kDa in SDS-PAGE, and 22.5 to 1,035 kDa in Blue Native PAGE. Using molecular sieves, the molecules are collected mainly in the >100 kDa retention solution. When observed under an atomic force microscope, the molecules show mixed morphologies of granular, bead-shaped, and ring-shaped molecules having a height of 1.5 to 3.1 nm. By the gel filtration method, the molecules can be eluted in the void volume fraction 8 with a molecular weight of 680 kDa or more, and in fraction 15 with a molecular weight of 17 to 44 kDa.

There is no limitation on the origin and form of the antibodies used in the present invention as long as they bind to Aβ oligomers but not to Aβ monomers.

"Antibodies" of the present invention include both monoclonal and polyclonal antibodies. The antibodies of the present invention also include any type of antibodies such as non-human animal antibodies, humanized antibodies, chimeric antibodies, human antibodies, the later-described minibodies, amino acid sequence-modified antibodies, modified antibodies conjugated to other molecules (for example, polymers such as polyethylene glycol), and sugar chain-modified antibodies.

Herein, the term "monoclonal antibodies" refers to antibodies that are obtained from a substantially homogeneous population of antibodies. That is, the individual antibodies constituting the population are identical with the exception of possible natural mutants that may be present in a trace amount. Monoclonal antibodies are highly specific and recognize a single antigenic site. Each of the monoclonal antibodies recognizes a single determinant of the antigen, in contrast to conventional (polyclonal) antibody preparations that typically contain different antibodies against different antigenic determinants (epitopes).

In addition to the above-mentioned specificity, monoclonal antibodies have the advantage that they can be synthesized from a hybridoma culture that is not contaminated with other immunoglobulins. Therefore, "monoclonal" indicates the characteristics of antibodies that can be obtained from a substantially homogeneous antibody population. This term does not indicate the requirement for any specific method for antibody production.

Basically, monoclonal antibodies can be produced by using known techniques. For example, they may be produced by the hybridoma method first described by Kohler and Milstein (Nature 256: 495-7, 1975), or by the recombinant DNA method (Cabilly et al., Proc. Natl. Acad. Sci. USA 81:3273-7, 1984), but the methods are not limited thereto. For example, when using the hybridoma method, an Aβ oligomer (for example, the Aβ tetramer described in the Examples) is used as a sensitizing antigen, and immunization is carried out according to a conventional immunization method. The obtained immune cells are fused with known parent cells by a conventional cell fusion method, and monoclonal antibody-producing cells can be screened and isolated using a conventional screening method.

The monoclonal antibodies of the present invention can be produced as follows. Synthetic Aβ 1-42 (Peptide Institute, Inc., Osaka) is dissolved in distilled deionized water or a 10 mM phosphate buffer solution, and this is incubated at 37° C. for 18 hours. Then, the peptides are separated by 4-12% SDS-PAGE, and visualized by CBB staining, and the portion of the Aβ 1-42 tetramer alone which is not contaminated with the Aβ 1-42 monomer is cut out and used as an antigen. On the other hand, a preparation containing a large amount of the Aβ 1-40 oligomer is prepared by mixing (i) a modified Aβ 1-40 prepared by chemically linking 6-carboxytetramethyl-rhodamine (6-TAMRA) (SIGMA) to the N terminus of a synthetic Aβ 1-40 peptide using a conventional method with (ii) synthetic Aβ 1-40 (Peptide Institute, Inc., Osaka) at a ratio of 5:100, 10:100, 20:100, 30:100, 40:100, 50:100, 60:100, 70:100, or 80:100, preferably 90:100, or more preferably 100:100, and carrying out polymerization reaction for three hours, preferably six hours, or more preferably 20 hours. Next, Balb-c mice are immunized with 2.5 µg of either the Aβ 1-42 tetramer or Aβ 1-40 oligomer emulsified using complete Freund's adjuvant by injecting the antigen into their foot pad. Subsequently, booster immunizations are carried out six times. Hybridomas are produced from the inguinal lymph node by fusion with Sp2/O-Ag14 cells using Polyethylene Glycol 1500.

The animals immunized with sensitizing antigens are not particularly limited, but are preferably selected considering the compatibility with parent cells used for cell fusion. Generally, rodents, lagomorphs, or primates are used. Rodents include, for example, mice, rats, and hamsters. Lagomorphs include, for example, rabbits. Primates include, for example, Catarrhini (old-world) monkeys such as *Macaca fascicularis, Macaca mulatta*, hamadryas, and chimpanzees.

Animals are immunized with sensitizing antigens according to known methods. For example, as a standard method, immunization is performed by intraperitoneal or subcutaneous injection of a sensitizing antigen into mammals.

An example of the parent cells fused with the aforementioned immunocytes is the Sp2/O-Ag14 cell, which will be described below in the Examples. However, various other known cell lines can be used.

Cell fusion between the aforementioned immunocyte and a myeloma cell can be carried out basically according to known methods including the method by Kohler and Milstein (Kohler G. and Milstein C., Methods Enzymol. (1981) 73, 3-46).

Hybridomas obtained in this manner are selected by culturing them in a conventional selection culture medium such as a HAT culture medium, which contains hypoxanthine, aminopterin, and thymidine. Culturing in the above-mentioned HAT culture medium is generally continued for several days to several weeks for an adequate time for killing cells other than the desired hybridomas (non-fused cells). Next, a conventional limiting dilution method is performed for screening and singly-cloning of a hybridoma that produces the desired antibody.

Thereafter, the obtained hybridoma is transplanted into the abdominal cavity of a mouse, and ascitic fluid containing the desired monoclonal antibodies is extracted. For example, the antibodies can be purified from the ascitic fluid by conventional protein separation and/or purification methods such as a selected combination of column chromatography including, but not limited to, affinity chromatography, filtration, ultrafiltration, salt precipitation, dialysis, SDS polyacrylamide gel electrophoresis, and isoelectric focusing (Antibodies: A Laboratory manual, Harlow and David, Lane (edit.), Cold Spring Harbor Laboratory, 1988).

Protein A columns and Protein G columns can be used for affinity columns. Examples of the Protein A columns used include Hyper D, POROS, and Sepharose F.F. (Pharmacia).

Chromatography (excluding affinity chromatography) includes ion exchange chromatography, hydrophobic chromatography, gel filtration, reverse-phase chromatography, and adsorption chromatography ("Strategies for Protein Purification and Characterization: A Laboratory Course Manual", Daniel R Marshak et al., Cold Spring Harbor Laboratory Press, 1996). When chromatography is carried out, liquid-phase chromatography methods such as HPLC and FPLC can be used.

Monoclonal antibody-producing hybridomas prepared in this manner can be subcultured in a conventional culture medium, and they can be stored for a long time in liquid nitrogen.

Any mammal can be immunized using an immunogen for antibody production. However, when preparing monoclonal antibodies by producing hybridomas, the compatibility with parent cells used in cell fusion for hybridoma production is preferably considered.

Generally, rodents, lagomorphs, or primates are used for the immunization. Rodents include, for example, mice, rats, and hamsters. Lagomorphs include, for example, rabbits. Primates include, for example, Catarrhini (old-world) monkeys such as *Macaca fascicularis, Macaca mulatta*, hamadryas, and chimpanzees.

The use of transgenic animals that have a human antibody gene repertoire is known in the art (Ishida I, et al., Cloning and Stem Cells 4: 91-102, 2002). As with other animals, to obtain human monoclonal antibodies, the transgenic animals are immunized, then antibody-producing cells are collected from the animals and fused with myeloma cells to produce hybridomas, and anti-protein human antibodies can be prepared from these hybridomas (see International Publication Nos. WO92/03918, WO94/02602, WO94/25585, WO96/33735, and WO96/34096).

Alternatively, lymphocytes immortalized with oncogenes may be used for monoclonal antibody production. For example, human lymphocytes infected with EB virus or such is immunized in vitro with immunogens. Next, the immunized lymphocytes are fused with human-derived myeloma cells (U266, etc) capable of unlimited division, and thus hybridomas that produce the desired human antibodies are obtained (Japanese Patent Application Kokai Publication No. (JP-A) S63-17688 (unexamined, published Japanese patent application)).

Once monoclonal antibodies can be obtained by any of the aforementioned methods, the antibodies may also be prepared using genetic engineering methods (see, for example, Borrebaeck C A K and Larrick J W, Therapeutic Monoclonal Antibodies, MacMillan Publishers, UK, 1990). For example, recombinant antibodies may be prepared by cloning DNAs that encode the desired antibodies from antigen-producing cells such as hybridomas or immunized lymphocytes that produce the antibodies, then inserting the cloned DNAs into appropriate vectors, and transfecting the vectors into suitable host cells. Such recombinant antibodies are also included in the present invention.

Examples of the monoclonal antibodies of the present invention include the 1A9 monoclonal antibody, 2C3 monoclonal antibody, 5A5 monoclonal antibody, 5A9 monoclonal antibody, 4F7 monoclonal antibody, 4H5 monoclonal antibody, 6E4 monoclonal antibody, and 6H4 monoclonal antibody. Preferably, the monoclonal antibodies include the antibodies of (i) to (vi) below:

(i) an antibody that comprises an H chain (heavy chain) having the amino acid sequence of SEQ ID NO: 1 and an L chain (light chain) having the amino acid sequence of SEQ ID NO: 3;

(ii) an antibody that comprises an H chain (heavy chain) having the amino acid sequence of SEQ ID NO: 21 and an L chain (light chain) having the amino acid sequence of SEQ ID NO: 23;

(iii) an antibody that comprises an H chain (heavy chain) having the amino acid sequence of SEQ ID NO: 41 and an L chain (light chain) having the amino acid sequence of SEQ ID NO: 43;

(iv) an antibody that comprises an H chain (heavy chain) having the amino acid sequence of SEQ ID NO: 61 and an L chain (light chain) having the amino acid sequence of SEQ ID NO: 63;

(v) an antibody that comprises an H chain (heavy chain) having the amino acid sequence of SEQ ID NO: 81 and an L chain (light chain) having the amino acid sequence of SEQ ID NO: 83;

(vi) an antibody that comprises an H chain (heavy chain) having the amino acid sequence of SEQ ID NO: 101 and an L chain (light chain) having the amino acid sequence of SEQ ID NO: 103.

In an embodiment, the antibodies of the present invention include minibodies. A minibody contains an antibody fragment lacking a portion of a whole antibody, and is not particularly limited as long as it has the ability to bind to an antigen. Examples of antibody fragments include Fab, Fab', F(ab')2, and Fv. Examples of minibodies include Fab, Fab', F(ab')2, Fv, scFv (single chain Fv), diabody, and sc(Fv)2 (single chain (Fv)2).

To obtain polyclonal antibodies against the proteins of the present invention, blood is removed from a mammal sensitized with an antigen after the serum level of the desired antibody is confirmed to be increased. Serum is separated from blood by a known method. When a polyclonal antibody is used, serum containing the polyclonal antibody may be utilized. Alternatively, if necessary, a fraction containing the polyclonal antibody may be isolated from serum and then used. For example, immunoglobulin G or M can be prepared by obtaining a fraction that specifically recognizes a protein of the present invention using an affinity column coupled with the protein, and then purifying this fraction using a Protein A or Protein G column.

In the present invention, the antibody that binds to an Aβ oligomer is an antibody binding to an Aβ oligomer that binds 1A9, 2C3, 5A5, 5A9, 4F7, 4H5, 6E4, or 6H4. Preferably, the antibody is any one of the antibodies of (A) to (F) below:

(A) an antibody binding to an Aβ oligomer that binds to an antibody comprising an H chain having the amino acid sequence of SEQ ID NO: 1 and an L chain having the amino acid sequence of SEQ ID NO: 3;

(B) an antibody binding to an Aβ oligomer that binds to an antibody comprising an H chain having the amino acid sequence of SEQ ID NO: 21 and an L chain having the amino acid sequence of SEQ ID NO: 23;

(C) an antibody binding to an Aβ oligomer that binds to an antibody comprising an H chain having the amino acid sequence of SEQ ID NO: 41 and an L chain having the amino acid sequence of SEQ ID NO: 43;

(D) an antibody binding to an Aβ oligomer that binds to an antibody comprising an H chain having the amino acid sequence of SEQ ID NO: 61 and an L chain having the amino acid sequence of SEQ ID NO: 63;

(E) an antibody binding to an Aβ oligomer that binds to an antibody comprising an H chain having the amino acid sequence of SEQ ID NO: 81 and an L chain having the amino acid sequence of SEQ ID NO: 83; and (F) an antibody binding to an Aβ oligomer that binds to an antibody comprising an H chain having the amino acid sequence of SEQ ID NO: 101 and an L chain having the amino acid sequence of SEQ ID NO: 103.

Furthermore, the present invention provides Aβ oligomers to which the antibodies of the present invention bind. Preferably, the antibodies include, for example, the 1A9 monoclonal antibody, 2C3 monoclonal antibody, 5A5 monoclonal antibody, 5A9 monoclonal antibody, 4F7 monoclonal antibody, 4H5 monoclonal antibody, 6E4 monoclonal antibody, and 6H4 monoclonal antibody. Such Aβ oligomers can be used as antigens for preparing antibodies, or vaccines.

In a preferred embodiment, the antibodies of the present invention include, for example, the antibody of any one of (1) to (38) below:

(1) an antibody that comprises an H chain having the amino acid sequence of SEQ ID NO: 9 as CDR1, the amino acid sequence of SEQ ID NO: 11 as CDR2, and the amino acid sequence of SEQ ID NO: 13 as CDR3;

(2) an antibody that comprises an L chain having the amino acid sequence of SEQ ID NO: 15 as CDR1, the amino acid sequence of SEQ ID NO: 17 as CDR2, and the amino acid sequence of SEQ ID NO: 19 as CDR3;

(3) an antibody that comprises the H chain of (1) and the L chain of (2);

(4) an antibody that comprises an H chain having the amino acid sequence of SEQ ID NO: 5 as VH;

(5) an antibody that comprises an L chain having the amino acid sequence of SEQ ID NO: 7 as VL;

(6) an antibody that comprises the H chain of (4) and the L chain of (5);

(7) an antibody that comprises an H chain having the amino acid sequence of SEQ ID NO: 29 as CDR1, the amino acid sequence of SEQ ID NO: 31 as CDR2, and the amino acid sequence of SEQ ID NO: 33 as CDR3;

(8) an antibody that comprises an L chain having the amino acid sequence of SEQ ID NO: 35 as CDR1, the amino acid sequence of SEQ ID NO: 37 as CDR2, and the amino acid sequence of SEQ ID NO: 39 as CDR3;

(9) an antibody that comprises the H chain of (7) and the L chain of (8);

(10) an antibody that comprises an H chain having the amino acid sequence of SEQ ID NO: 25 as VH;

(11) an antibody that comprises an L chain having the amino acid sequence of SEQ ID NO: 27 as VL;

(12) an antibody that comprises the H chain of (10) and the L chain of (11);

(13) an antibody that comprises an H chain having the amino acid sequence of SEQ ID NO: 49 as CDR1, the amino acid sequence of SEQ ID NO: 51 as CDR2, and the amino acid sequence of SEQ ID NO: 53 as CDR3;

(14) an antibody that comprises an L chain having the amino acid sequence of SEQ ID NO: 55 as CDR1, the amino acid sequence of SEQ ID NO: 57 as CDR2, and the amino acid sequence of SEQ ID NO: 59 as CDR3;

(15) an antibody that comprises the H chain of (13) and the L chain of (14);

(16) an antibody that comprises an H chain having the amino acid sequence of SEQ ID NO: 45 as VH;

(17) an antibody that comprises an L chain having the amino acid sequence of SEQ ID NO: 47 as VL;

(18) an antibody that comprises the H chain of (16) and the L chain of (17);

(19) an antibody that comprises an H chain having the amino acid sequence of SEQ ID NO: 69 as CDR1, the amino acid sequence of SEQ ID NO: 71 as CDR2, and the amino acid sequence of SEQ ID NO: 73 as CDR3;

(20) an antibody that comprises an L chain having the amino acid sequence of SEQ ID NO: 75 as CDR1, the amino acid sequence of SEQ ID NO: 77 as CDR2, and the amino acid sequence of SEQ ID NO: 79 as CDR3;

(21) an antibody that comprises the H chain of (19) and the L chain of (20);

(22) an antibody that comprises an H chain having the amino acid sequence of SEQ ID NO: 65 as VH;

(23) an antibody that comprises an L chain having the amino acid sequence of SEQ ID NO: 67 as VL;

(24) an antibody that comprises the H chain of (22) and the L chain of (23);

(25) an antibody that comprises an H chain having the amino acid sequence of SEQ ID NO: 89 as CDR1, the amino acid sequence of SEQ ID NO: 91 as CDR2, and the amino acid sequence of SEQ ID NO: 93 as CDR3;

(26) an antibody that comprises an L chain having the amino acid sequence of SEQ ID NO: 95 as CDR1, the amino acid sequence of SEQ ID NO: 97 as CDR2, and the amino acid sequence of SEQ ID NO: 99 as CDR3;

(27) an antibody that comprises the H chain of (25) and the L chain of (26);
(28) an antibody that comprises an H chain having the amino acid sequence of SEQ ID NO: 85 as VH;
(29) an antibody that comprises an L chain having the amino acid sequence of SEQ ID NO: 87 as VL;
(30) an antibody that comprises the H chain of (28) and the L chain of (29);
(31) an antibody that comprises an H chain having the amino acid sequence of SEQ ID NO: 109 as CDR1, the amino acid sequence of SEQ ID NO: 111 as CDR2, and the amino acid sequence of SEQ ID NO: 113 as CDR3;
(32) an antibody that comprises an L chain having the amino acid sequence of SEQ ID NO: 115 as CDR1, the amino acid sequence of SEQ ID NO: 117 as CDR2, and the amino acid sequence of SEQ ID NO: 119 as CDR3;
(33) an antibody that comprises the H chain of (31) and the L chain of (32);
(34) an antibody that comprises an H chain having the amino acid sequence of SEQ ID NO: 105 as VH;
(35) an antibody that comprises an L chain having the amino acid sequence of SEQ ID NO: 107 as VL;
(36) an antibody that comprises the H chain of (34) and the L chain of (35);
(37) an antibody that comprises one or more amino acid substitutions, deletions, additions, and/or insertions in the antibody of any one of (1) to (36), which has equivalent activity as the antibody of any one of (1) to (36); and
(38) an antibody that binds to the epitope bound by the antibody of any one of (1) to (36).

An example of the VH in the above-mentioned "H chain having the amino acid sequence of SEQ ID NO: 9 (sequence of the 5A5 antibody H-chain CDR1) as CDR1, the amino acid sequence of SEQ ID NO: 11 (sequence of the 5A5 antibody H-chain CDR2) as CDR2, and the amino acid sequence of SEQ ID NO: 13 (sequence of the 5A5 antibody H-chain CDR3) as CDR3" of (1) is a VH having the amino acid sequence of SEQ ID NO: 5 (sequence of the 5A5 antibody VH).

An example of the VL in the above-mentioned "L chain having the amino acid sequence of SEQ ID NO: 15 (sequence of the 5A5 antibody L-chain CDR1) as CDR1, the amino acid sequence of SEQ ID NO: 17 (sequence of the 5A5 antibody L-chain CDR2) as CDR2, and the amino acid sequence of SEQ ID NO: 19 (sequence of the 5A5 antibody L-chain CDR3) as CDR3" of (2) is a VL having the amino acid sequence of SEQ ID NO: 7 (sequence of the 5A5 antibody VL).

An example of the VH in the above-mentioned "H chain having the amino acid sequence of SEQ ID NO: 29 (sequence of the 5A9 antibody H-chain CDR1) as CDR1, the amino acid sequence of SEQ ID NO: 31 (sequence of the 5A9 antibody H-chain CDR2) as CDR2, and the amino acid sequence of SEQ ID NO: 33 (sequence of the 5A9 antibody H-chain CDR3) as CDR3" of (7) is a VH having the amino acid sequence of SEQ ID NO: 25 (sequence of the 5A9 antibody VH).

An example of the VL in the above-mentioned "L chain having the amino acid sequence of SEQ ID NO: 35 (sequence of the 5A9 antibody L-chain CDR1) as CDR1, the amino acid sequence of SEQ ID NO: 37 (sequence of the 5A9 antibody L-chain CDR2) as CDR2, and the amino acid sequence of SEQ ID NO: 39 (sequence of the 5A9 antibody L-chain CDR3) as CDR3" of (8) is a VL having the amino acid sequence of SEQ ID NO: 27 (sequence of the 5A9 antibody VL).

An example of the VH in the above-mentioned "H chain having the amino acid sequence of SEQ ID NO: 49 (sequence of the 4F7 antibody H-chain CDR1) as CDR1, the amino acid sequence of SEQ ID NO: 51 (sequence of the 4F7 antibody H-chain CDR2) as CDR2, and the amino acid sequence of SEQ ID NO: 53 (sequence of the 4F7 antibody H-chain CDR3) as CDR3" of (13) is a VH having the amino acid sequence of SEQ ID NO: 45 (sequence of the 4F7 antibody VH).

An example of the VL in the above-mentioned "L chain having the amino acid sequence of SEQ ID NO: 55 (sequence of the 4F7 antibody L-chain CDR1) as CDR1, the amino acid sequence of SEQ ID NO: 57 (sequence of the 4F7 antibody L-chain CDR2) as CDR2, and the amino acid sequence of SEQ ID NO: 59 (sequence of the 4F7 antibody L-chain CDR3) as CDR3" of (14) is a VL having the amino acid sequence of SEQ ID NO: 47 (sequence of the 4F7 antibody VL).

An example of the VH in the above-mentioned "H chain having the amino acid sequence of SEQ ID NO: 69 (sequence of the 4H5 antibody H-chain CDR1) as CDR1, the amino acid sequence of SEQ ID NO: 71 (sequence of the 4H5 antibody H-chain CDR2) as CDR2, and the amino acid sequence of SEQ ID NO: 73 (sequence of the 4H5 antibody H-chain CDR3) as CDR3" of (19) is a VH having the amino acid sequence of SEQ ID NO: 65 (sequence of the 4H5 antibody VH).

An example of the VL in the above-mentioned "L chain having the amino acid sequence of SEQ ID NO: 75 (sequence of the 4H5 antibody L-chain CDR1) as CDR1, the amino acid sequence of SEQ ID NO: 77 (sequence of the 4H5 antibody L-chain CDR2) as CDR2, and the amino acid sequence of SEQ ID NO: 79 (sequence of the 4H5 antibody L-chain CDR3) as CDR3" of (20) is a VL having the amino acid sequence of SEQ ID NO: 67 (sequence of the 4H5 antibody VL).

An example of the VH in the above-mentioned "H chain having the amino acid sequence of SEQ ID NO: 89 (sequence of the 6E4 antibody H-chain CDR1) as CDR1, the amino acid sequence of SEQ ID NO: 91 (sequence of the 6E4 antibody H-chain CDR2) as CDR2, and the amino acid sequence of SEQ ID NO: 93 (sequence of the 6E4 antibody H-chain CDR3) as CDR3" of (25) is a VH having the amino acid sequence of SEQ ID NO: 85 (sequence of the 6E4 antibody VH).

An example of the VL in the above-mentioned "L chain having the amino acid sequence of SEQ ID NO: 95 (sequence of the 6E4 antibody L-chain CDR1) as CDR1, the amino acid sequence of SEQ ID NO: 97 (sequence of the 6E4 antibody L-chain CDR2) as CDR2, and the amino acid sequence of SEQ ID NO: 99 (sequence of the 6E4 antibody L-chain CDR3) as CDR3" of (26) is a VL having the amino acid sequence of SEQ ID NO: 87 (sequence of the 6E4 antibody VL).

An example of the VH in the above-mentioned "H chain having the amino acid sequence of SEQ ID NO: 109 (sequence of the 6H4 antibody H-chain CDR1) as CDR1, the amino acid sequence of SEQ ID NO: 111 (sequence of the 6H4 antibody H-chain CDR2) as CDR2, and the amino acid sequence of SEQ ID NO: 113 (sequence of the 6H4 antibody H-chain CDR3) as CDR3" of (31) is a VH having the amino acid sequence of SEQ ID NO: 105 (sequence of the 6H4 antibody VH).

An example of the VL in the above-mentioned "L chain having the amino acid sequence of SEQ ID NO: 115 (sequence of the 6H4 antibody L-chain CDR1) as CDR1, the amino acid sequence of SEQ ID NO: 117 (sequence of the 6H4 antibody L-chain CDR2) as CDR2, and the amino acid sequence of SEQ ID NO: 119 (sequence of the 6H4 antibody L-chain CDR3) as CDR3" of (32) is a VL having the amino acid sequence of SEQ ID NO: 107 (sequence of the 6H4 antibody VL).

For the 5A5 antibody of the present invention, the amino acid sequence and the nucleotide sequence of the full-length H chain are shown in SEQ ID NO: 1 and SEQ ID NO: 2, respectively; the amino acid sequence and the nucleotide sequence of the full-length L chain are shown in SEQ ID NO: 3 and SEQ ID NO: 4, respectively; the amino acid sequence and the nucleotide sequence of the H-chain variable region (VH) are shown in SEQ ID NO: 5 and SEQ ID NO: 6, respectively; the amino acid sequence and the nucleotide sequence of the L-chain variable region (VL) are shown in SEQ ID NO: 7 and SEQ ID NO: 8, respectively; the amino acid sequence and the nucleotide sequence of the H-chain CDR1 are shown in SEQ ID NO: 9 and SEQ ID NO: 10, respectively; the amino acid sequence and the nucleotide sequence of the H-chain CDR2 are shown in SEQ ID NO: 11 and SEQ ID NO: 12, respectively; the amino acid sequence and the nucleotide sequence of the H-chain CDR3 are shown in SEQ ID NO: 13 and SEQ ID NO: 14, respectively; the amino acid sequence and the nucleotide sequence of the L-chain CDR1 are shown in SEQ ID NO: 15 and SEQ ID NO: 16, respectively; the amino acid sequence and the nucleotide sequence of the L-chain CDR2 are shown in SEQ ID NO: 17 and SEQ ID NO: 18, respectively; and the amino acid sequence and the nucleotide sequence of the L-chain CDR3 are shown in SEQ ID NO: 19 and SEQ ID NO: 20, respectively.

For the 5A9 antibody of the present invention, the amino acid sequence and the nucleotide sequence of the full-length H chain are shown in SEQ ID NO: 21 and SEQ ID NO: 22, respectively; the amino acid sequence and the nucleotide sequence of the full-length L chain are shown in SEQ ID NO: 23 and SEQ ID NO: 24, respectively; the amino acid sequence and the nucleotide sequence of the H-chain variable region (VH) are shown in SEQ ID NO: 25 and SEQ ID NO: 26, respectively; the amino acid sequence and the nucleotide sequence of the L-chain variable region (VL) are shown in SEQ ID NO: 27 and SEQ ID NO: 28, respectively; the amino acid sequence and the nucleotide sequence of the H-chain CDR1 are shown in SEQ ID NO: 29 and SEQ ID NO: 30, respectively; the amino acid sequence and the nucleotide sequence of the H-chain CDR2 are shown in SEQ ID NO: 31 and SEQ ID NO: 32, respectively; the amino acid sequence and the nucleotide sequence of the H-chain CDR3 are shown in SEQ ID NO: 33 and SEQ ID NO: 34, respectively; the amino acid sequence and the nucleotide sequence of the L-chain CDR1 are shown in SEQ ID NO: 35 and SEQ ID NO: 36, respectively; the amino acid sequence and the nucleotide sequence of the L-chain CDR2 are shown in SEQ ID NO: 37 and SEQ ID NO: 38, respectively; and the amino acid sequence and the nucleotide sequence of the L-chain CDR3 are shown in SEQ ID NO: 39 and SEQ ID NO: 40, respectively.

For the 4F7 antibody of the present invention, the amino acid sequence and the nucleotide sequence of the full-length H chain are shown in SEQ ID NO: 41 and SEQ ID NO: 42, respectively; the amino acid sequence and the nucleotide sequence of the full-length L chain are shown in SEQ ID NO: 43 and SEQ ID NO: 44, respectively; the amino acid sequence and the nucleotide sequence of the H-chain variable region (VH) are shown in SEQ ID NO: 45 and SEQ ID NO: 46, respectively; the amino acid sequence and the nucleotide sequence of the L-chain variable region (VL) are shown in SEQ ID NO: 47 and SEQ ID NO: 48, respectively; the amino acid sequence and the nucleotide sequence of the H-chain CDR1 are shown in SEQ ID NO: 49 and SEQ ID NO: 50, respectively; the amino acid sequence and the nucleotide sequence of the H-chain CDR2 are shown in SEQ ID NO: 51 and SEQ ID NO: 52, respectively; the amino acid sequence and the nucleotide sequence of the H-chain CDR3 are shown in SEQ ID NO: 53 and SEQ ID NO: 54, respectively; the amino acid sequence and the nucleotide sequence of the L-chain CDR1 are shown in SEQ ID NO: 55 and SEQ ID NO: 56, respectively; the amino acid sequence and the nucleotide sequence of the L-chain CDR2 are shown in SEQ ID NO: 57 and SEQ ID NO: 58, respectively; and the amino acid sequence and the nucleotide sequence of the L-chain CDR3 are shown in SEQ ID NO: 59 and SEQ ID NO: 60, respectively.

For the 4H5 antibody of the present invention, the amino acid sequence and the nucleotide sequence of the full-length H chain are shown in SEQ ID NO: 61 and SEQ ID NO: 62, respectively; the amino acid sequence and the nucleotide sequence of the full-length L chain are shown in SEQ ID NO: 63 and SEQ ID NO: 64, respectively; the amino acid sequence and the nucleotide sequence of the H-chain variable region (VH) are shown in SEQ ID NO: 65 and SEQ ID NO: 66, respectively; the amino acid sequence and the nucleotide sequence of the L-chain variable region (VL) are shown in SEQ ID NO: 67 and SEQ ID NO: 68, respectively; the amino acid sequence and the nucleotide sequence of the H-chain CDR1 are shown in SEQ ID NO: 69 and SEQ ID NO: 70, respectively; the amino acid sequence and the nucleotide sequence of the H-chain CDR2 are shown in SEQ ID NO: 71 and SEQ ID NO: 72, respectively; the amino acid sequence and the nucleotide sequence of the H-chain CDR3 are shown in SEQ ID NO: 73 and SEQ ID NO: 74, respectively; the amino acid sequence and the nucleotide sequence of the L-chain CDR1 are shown in SEQ ID NO: 75 and SEQ ID NO: 76, respectively; the amino acid sequence and the nucleotide sequence of the L-chain CDR2 are shown in SEQ ID NO: 77 and SEQ ID NO: 78, respectively; and the amino acid sequence and the nucleotide sequence of the L-chain CDR3 are shown in SEQ ID NO: 79 and SEQ ID NO: 80, respectively.

For the 6E4 antibody of the present invention, the amino acid sequence and the nucleotide sequence of the full-length H chain are shown in SEQ ID NO: 81 and SEQ ID NO: 82, respectively; the amino acid sequence and the nucleotide sequence of the full-length L chain are shown in SEQ ID NO: 83 and SEQ ID NO: 84, respectively; the amino acid sequence and the nucleotide sequence of the H-chain variable region (VH) are shown in SEQ ID NO: 85 and SEQ ID NO: 86, respectively; the amino acid sequence and the nucleotide sequence of the L-chain variable region (VL) are shown in SEQ ID NO: 87 and SEQ ID NO: 88, respectively; the amino acid sequence and the nucleotide sequence of the H-chain CDR1 are shown in SEQ ID NO: 89 and SEQ ID NO: 90, respectively; the amino acid sequence and the nucleotide sequence of the H-chain CDR2 are shown in SEQ ID NO: 91 and SEQ ID NO: 92, respectively; the amino acid sequence and the nucleotide sequence of the H-chain CDR3 are shown in SEQ ID NO: 93 and SEQ ID NO: 94, respectively; the amino acid sequence and the nucleotide sequence of the L-chain CDR1 are shown in SEQ ID NO: 95 and SEQ ID NO: 96, respectively; the amino acid sequence and the nucleotide sequence of the L-chain CDR2 are shown in SEQ ID NO: 97 and SEQ ID NO: 98, respectively; and the amino acid sequence and the nucleotide sequence of the L-chain CDR3 are shown in SEQ ID NO: 99 and SEQ ID NO: 100, respectively.

For the 6H4 antibody of the present invention, the amino acid sequence and the nucleotide sequence of the full-length H chain are shown in SEQ ID NO: 101 and SEQ ID NO: 102, respectively; the amino acid sequence and the nucleotide sequence of the full-length L chain are shown in SEQ ID NO: 103 and SEQ ID NO: 104, respectively; the amino acid sequence and the nucleotide sequence of the H-chain variable region (VH) are shown in SEQ ID NO: 105 and SEQ ID NO: 106, respectively; the amino acid sequence and the nucleotide sequence of the L-chain variable region (VL) are shown in SEQ ID NO: 107 and SEQ ID NO: 108, respectively; the amino acid sequence and the nucleotide sequence of the H-chain CDR1 are shown in SEQ ID NO: 109 and SEQ ID NO: 110, respectively; the amino acid sequence and the nucleotide sequence of the H-chain CDR2 are shown in SEQ ID NO: 111 and SEQ ID NO: 112, respectively; the amino acid sequence and the nucleotide sequence of the H-chain CDR3 are shown in SEQ ID NO: 113 and SEQ ID NO: 114, respectively; the amino acid sequence and the nucleotide sequence of the L-chain CDR1 are shown in SEQ ID NO: 115 and SEQ ID NO: 116, respectively; the amino acid sequence and the nucleotide sequence of the L-chain CDR2 are shown in SEQ ID NO: 117 and SEQ ID NO: 118, respectively; and the amino acid sequence and the nucleotide sequence of the L-chain CDR3 are shown in SEQ ID NO: 119 and SEQ ID NO: 120, respectively.

The above-mentioned antibodies of (1) to (38) include not only monovalent antibodies but also multivalent antibodies with two or more valencies. The multivalent antibodies of the present invention include multivalent antibodies whose antigen binding sites are all the same and multivalent antibodies whose antigen binding sites are partially or completely different.

In a preferred embodiment, the above-mentioned antibody of (37) is an antibody with no modified CDRs. For example, the "antibody that comprises one or more amino acid substitutions, deletions, additions, and/or insertions in the antibody of (1), which has equivalent activity as the antibody of (1)" of the above-mentioned antibody of (37) is preferably "an antibody that has equivalent activity as the antibody of (1), and comprises one or more amino acid substitutions, deletions, additions, and/or insertions in the antibody of (1), and comprises an H chain having the amino acid sequence of SEQ ID NO: 9 as CDR1, the amino acid sequence of SEQ ID NO:11 as CDR2, and the amino acid sequence of SEQ ID NO: 13 as CDR3". Another preferred antibody of the above-mentioned antibody of (37) can be expressed in a similar manner.

Herein, "equivalent activity" means that the antibody of interest has biological or biochemical activity similar to that of an antibody of the present invention. Examples of the "activity" of the present invention include the activity to bind specifically to Aβ oligomers but not to Aβ monomers, anti-neurotoxic activity, activity to suppress Aβ amyloid fibril formation, anti-synaptic toxicity activity, and anti-memory impairment activity.

Methods for preparing a polypeptide having activity equivalent to that of a certain polypeptide that are well known to those skilled in the art include methods for introducing mutations into a polypeptide. For example, one skilled in the art can prepare an antibody having activity equivalent to that of an antibody of the present invention by introducing appropriate mutations into the antibody using site-directed mutagenesis (Hashimoto-Gotoh, T. et al. (1995) Gene 152, 271-275; Zoller, M J, and Smith, M. (1983) Methods Enzymol. 100, 468-500; Kramer, W. et al. (1984) Nucleic Acids Res. 12, 9441-9456; Kramer W, and Fritz H J (1987) Methods. Enzymol. 154, 350-367; Kunkel, T A (1985) Proc. Natl. Acad. Sci. USA. 82, 488-492; Kunkel (1988) Methods Enzymol. 85, 2763-2766) and such. Amino acid mutations may also occur naturally. The antibodies of the present invention also include an antibody that comprises an amino acid sequence with one or more amino acid mutations in the amino acid sequence of an antibody of the present invention, and which has activity equivalent to that of the antibody of the present invention. The number of mutated amino acids in such mutants may be generally 50 amino acids or less, preferably 30 amino acids or less, and more preferably ten amino acids or less (for example, five amino acids or less).

Amino acid residues are preferably mutated into other amino acids that conserve the properties of the amino acid side chains. For example, amino acids are categorized as follows depending on the side chain properties: hydrophobic amino acids (A, I, L, M, F, P, W, Y, and V), hydrophilic amino acids (R, D, N, C, E, Q, G, H, K, S, and T), amino acids with aliphatic side chains (G, A, V, L, I, and P), amino acids with hydroxyl-containing side chains (S, T, and Y), amino acids with sulfur atom-containing side chains (C and M), amino acids with carboxylic acid- and amide-containing side chains (D, N, E, and Q), amino acids with basic side chains (R, K, and H), and amino acids with aromatic ring-containing side chains (H, F, Y, and W) (amino acids are represented by one-letter codes in parentheses).

A polypeptide having an amino acid sequence, in which one or more amino acid residues are modified (deleted, added, and/or substituted with other amino acids) in a certain amino acid sequence, is known to retain its original biological activity (function).

In addition to the above-mentioned modifications, the antibodies of the present invention may be conjugated to other substances as long as the activity is maintained. Examples of the substances include peptides, lipids, sugars and sugar chains, acetyl groups, and natural and synthetic polymers. These modifications may be performed to confer additional functions to the antibodies, or to stabilize the antibodies.

Antibodies in which several amino acid residues have been added to the amino acid sequence of an antibody of the present invention include fusion proteins containing the antibody. In the fusion proteins, the antibody is fused with another peptide or protein. Methods for producing a fusion protein can be carried out by ligating a polynucleotide encoding an antibody of the present invention in frame with a polynucleotide encoding another peptide or polypeptide, and inserting this into an expression vector, and expressing the fusion construct in a host. Techniques known to those skilled in the art can be used for this purpose. The peptides or polypeptides fused with an antibody of the present invention include, for example, known peptides such as FLAG (Hopp, T. P. et al., BioTechnology (1988) 6, 1204-1210), 6×His consisting of six histidine (His) residues, 10×His, Influenza hemagglutinin (HA), human c-myc fragments, VSV-GP fragments, p18HIV fragments, T7-tag, HSV-tag, E-tag, SV40T antigen fragments, lck tag, α-tubulin fragments, B-tag, and Protein C fragments; glutathione-S-transferase (GST); immunoglobulin constant regions; β-galactosidase; and maltose-binding protein (MBP), etc. Commercially available polynucleotides encoding these peptides or polypeptides can be fused with polynucleotides encoding the antibodies of the present invention, and the fusion polypeptides can be produced by expressing the fusion polynucleotides thus prepared.

The antibodies of the present invention may differ in the amino acid sequence, molecular weight, presence or absence of sugar chains, structure and such, depending on the cell or host producing the antibodies or the purification method. However, as long as the obtained antibody has an activity equivalent to an antibody of the present invention, it is included in the present invention.

Antibodies that bind to an epitope to which an antibody of any one of (1) to (36) above binds can be obtained by methods known to those skilled in the art. For example, the antibodies can be obtained by (i) determining the epitope bound by the antibody of any one of (1) to (36) using a conventional method, and producing the antibodies using a polypeptide comprising an amino acid sequence included in the epitope as an immunogen; or (ii) determining the epitopes of antibodies produced by a conventional method, and selecting antibodies whose epitope is the same as that of the antibody of any one of (1) to (36).

The above-mentioned antibodies of (1) to (38) also include any type of antibodies such as the above-described minibodies, antibodies with modified amino acid sequences such as humanized antibodies and chimeric antibodies, non-human animal antibodies, human antibodies, modified antibodies conjugated to other molecules (for example, polymers such as polyethylene glycol), and sugar chain-modified antibodies.

In a preferred embodiment, the antibodies of the present invention are modified antibodies such as chimeric antibodies and humanized antibodies. Examples of preferred antibodies include (i) a chimeric antibody whose variable region is derived from the 2C3 antibody, 1A9 antibody, 5A5 antibody, 5A9 antibody, 4F7 antibody, 4H5 antibody, 6E4 antibody, or 6H4 antibody, and whose constant region is derived from a human immunoglobulin; and (ii) a humanized antibody whose CDR is derived from the 2C3 antibody, 1A9 antibody, 5A5 antibody, 5A9 antibody, 4F7 antibody, 4H5 antibody, 6E4 antibody, or 6H4 antibody, and whose FR is derived from a human immunoglobulin, and whose constant region is derived from a human immunoglobulin. These modified antibodies can be produced using known methods.

Since the antigenicity of a chimeric antibody or a humanized antibody in the human body is reduced, such an antibody is useful for administration to humans for therapeutic purposes or such.

Chimeric antibodies are produced by combining sequences derived from different animals. Examples of chimeric antibodies include antibodies comprising the heavy-chain and light-chain variable regions of a mouse antibody and the heavy-chain and light-chain constant regions of a human antibody. The production of chimeric antibodies can be carried out using known methods (see, for example, Jones et al., Nature 321:522-5, 1986; Riechmann et al., Nature 332:323-7, 1988; and Presta, Curr. Opin. Struct. Biol. 2:593-6, 1992). For example, first, genes encoding the variable regions or CDRs of the antibody of interest are prepared from the RNAs of antibody-producing cells by polymerase chain reaction (PCR) or such (see, for example, Larrick et al., "Methods: a Companion to Methods in Enzymology", Vol. 2: 106, 1991; Courtenay-Luck, "Genetic Manipulation of Monoclonal Antibodies" in Monoclonal Antibodies: Production, Engineering and Clinical Application; Ritter et al. (eds.), page 166, Cambridge University Press, 1995, and Ward et al., "Genetic Manipulation and Expression of Antibodies" in Monoclonal Antibodies: Principles and Applications; and Birch et al. (eds.), page 137, Wiley-Liss, Inc., 1995). The prepared genes encoding the variable regions are linked to genes encoding the constant regions or framework regions. The genes encoding the constant regions or framework regions may be determined in a manner similar to that for the CDR-encoding genes, or alternatively, they can be prepared based on the sequence information of known antibodies. DNA sequences encoding chimeric products and CDR-grafted products may be synthesized completely or partially using oligonucleotide synthesis techniques. For example, the oligonucleotide synthesis described by Jones et al. (Nature 321:522-5, 1986) may be performed. Furthermore, in some cases, site-directed mutagenesis and polymerase chain reaction techniques may be appropriately used. Techniques for oligonucleotide-specific mutagenesis of known variable regions described by Verhoeyen et al. (Science 239: 1534-6, 1988) and Riechmann et al. (Nature 332: 323-7, 1988) may be used for modifying the variable region sequences, for example, to enhance the binding ability of chimeric antibodies. Furthermore, if necessary, enzymatic fill-in of gapped oligonucleotides using T4 DNA polymerase may be performed, for example, as described by Queen et al. (Proc. Natl. Acad. Sci. USA 86: 10029-33, 1989; and WO 90/07861).

For example, CDR-grafting techniques are known in the art ("Immunoglobulin genes", Academic Press (London), pp 260-74, 1989; and Michael A et al., Proc. Natl. Acad. Sci. USA 91: 969-73, 1994). Using the techniques, the CDRs of a certain antibody are replaced with the CDRs of another antibody. Through such replacement, the binding specificity of the former antibody is changed to that of the latter antibody. Among such chimeric antibodies, those in which the framework amino acids are derived from a human antibody are called "humanized antibodies (CDR-grafted antibodies)". When using antibodies to treat humans, human antibodies or humanized antibodies are preferably utilized.

Generally, chimeric antibodies comprise the variable regions of a non-human mammal-derived antibody and the constant regions derived from a human antibody. On the other hand, humanized antibodies comprise the complementarity-determining regions of a non-human mammal-derived antibody and the framework regions and constant regions derived from a human antibody.

After producing the chimeric antibodies or humanized antibodies, amino acids in the variable regions (for example, FRs) or the constant regions may be substituted with other amino acids.

The origin of the variable regions of the chimeric antibodies or the CDRs of the humanized antibodies is not particularly limited.

Human antibody-derived C-regions are used for the C-regions of the chimeric antibodies and humanized antibodies. For example, Cγ1, Cγ2, Cγ3, Cγ4, Cμ, Cδ, Cα1, Cα2, and Cε can be used for the H-chain C-regions, and Cκ and Cλ can be used for the L-chain C-regions. Their sequences are known. Furthermore, the human antibody C regions can be modified to improve the stability of the antibodies or their production.

The binding activity of the antibodies of the present invention to the antigens (Aβ oligomers) can be measured using, for example, an absorbance measurement method, an enzyme-linked immunosorbent assay (ELISA) method, an enzyme immunoassay (EIA) method, a radioimmunoassay (RIA) method, and/or a fluoroimmunoassay method. In ELISA, an antibody is immobilized on a plate, and an antigen for the antibody is added to the plate, then a sample containing the desired antibody, such as the culture supernatant of antibody-producing cells or a purified antibody is added. Next, a secondary antibody which recognizes the primary antibody and is tagged with an enzyme such as alkaline phosphatase is added to the plate, and this is preincubated. After washing, an enzyme substrate such as p-nitrophenyl phosphate is added to the plate, and the absorbance is measured to evaluate the antigen-binding ability of the sample of interest. The evaluation can be performed using BIAcore (Pharmacia).

Furthermore, the present invention provides compositions comprising the above-mentioned antibody of the present invention and a pharmaceutically acceptable carrier.

As described below, the present invention strongly suggests that monoclonal 1A9 and 2C3 antibody are promising candidates for therapeutic antibodies for preventing Alzheimer-like phenotypes. Memory deterioration has been shown to be related to synaptic dysfunction caused by soluble Aβ oligomers (Klein W L, 2001, Trends Neurosci; and Selkoe D J, 2002, Science). Excessive accumulation and deposition of Aβ oligomers may trigger the complicated downstream cascades that cause Alzheimer's disease. If this is the case, therapeutic intervention using a composition comprising an antibody of the present invention and a pharmaceutically acceptable carrier could be effective for blocking the pathologic cascades, and thus this could enable the treatment of Alzheimer's disease.

The "treatment" of the present invention does not necessarily have complete therapeutic or preventive effects against organs or tissues exhibiting symptoms of disorders or diseases, but may have partial effects.

"Treatment of Alzheimer's disease" in the present invention means amelioration of at least one symptom that may be caused by Alzheimer's disease, and examples include amelioration or suppression of cognitive impairment, amelioration or suppression of senile plaque formation, amelioration or suppression of synaptic dysfunction, and reduction or suppression of Aβ accumulation in brain tissues, blood, or such. Herein, "cognitive impairment" includes, for example, memory impairment including long term/short term memory impairment, object recognition memory impairment, spatial memory impairment, and associative and emotional memory impairment.

The present invention provides pharmaceutical compositions or pharmaceutical agents which comprise as an active ingredient the above-described composition comprising an antibody of the present invention and a pharmaceutically acceptable carrier.

In the present invention, the phrase "comprising as an active ingredient the above-described composition comprising an antibody of the present invention and a pharmaceutically acceptable carrier" means comprising the above-described composition comprising an antibody of the present invention and a pharmaceutically acceptable carrier as a major ingredient, but does not limit its content rate.

Examples of the above-mentioned pharmaceutical compositions include agents against cognitive impairment, Alzheimer's disease agents, agents for suppressing the progression of Alzheimer's disease, agents for suppressing senile plaque formation, agents for suppressing Aβ accumulation, antineurotoxic agents (agents for neutralizing neurotoxicity), agents for inhibiting Aβ amyloid fibril formation, and anti-synaptic toxicity agents (agents for neutralizing synaptic toxicity).

The above-mentioned pharmaceutical composition of the present invention can be expressed, for example, as "methods for suppressing Alzheimer's disease" which comprise the step of administering to a subject (individual) the above-described composition comprising an antibody of the present invention and a pharmaceutically acceptable carrier. In other embodiments, examples include methods for suppressing cognitive impairment, methods for suppressing the progression of Alzheimer's disease, methods for suppressing senile plaque formation, methods for suppressing Aβ accumulation, methods for neutralizing (suppressing) neurotoxic activity, methods for inhibiting Aβ amyloid fibril formation, and methods for neutralizing (suppressing) synaptic toxicity. In further embodiments, examples include methods for preventing and/or treating cognitive impairment, and methods for preventing and/or treating Alzheimer's disease.

The present invention also provides use of a composition comprising the above-described antibody of the present invention and a pharmaceutically acceptable carrier in the production of the above-mentioned pharmaceutical composition.

Furthermore, the present invention relates to the following compositions.

A composition comprising the above-described antibody of the present invention and a pharmaceutically acceptable carrier for use in preventing and/or treating cognitive impairment.

A composition comprising the above-described antibody of the present invention and a pharmaceutically acceptable carrier for use in preventing and/or treating Alzheimer's disease.

A composition comprising the above-described antibody of the present invention and a pharmaceutically acceptable carrier for use in suppressing the progression of Alzheimer's disease.

A composition comprising the above-described antibody of the present invention and a pharmaceutically acceptable carrier for use in suppressing senile plaque formation.

A composition comprising the above-described antibody of the present invention and a pharmaceutically acceptable carrier for use in suppressing Aβ accumulation.

A composition comprising the above-described antibody of the present invention and a pharmaceutically acceptable carrier for use in neutralizing (suppressing) neurotoxic activity.

A composition comprising the above-described antibody of the present invention and a pharmaceutically acceptable carrier for use in inhibiting Aβ amyloid fibril formation.

A composition comprising the above-described antibody of the present invention and a pharmaceutically acceptable carrier for use in neutralizing (suppressing) synaptic toxicity.

The above-mentioned pharmaceutical agents of the present invention can be administered to humans or other animals. In the present invention, non-human animals to which the pharmaceutical agents are administered include mice, rats, guinea pigs, rabbits, chickens, cats, dogs, sheep, pigs, cattle, monkeys, baboons, and chimpanzees. These animals preferably exhibit at least one symptom selected from, for example, cognitive impairment, senile plaque formation, synaptic dysfunction, Aβ accumulation in brain tissues or blood, etc.

Antibodies contained in the pharmaceutical compositions of the present invention are not particularly limited as long as they are included in the above-mentioned antibodies of the present invention, and examples include the antibodies described herein.

When using the above-mentioned antibodies of the present invention for pharmaceutical compositions, they may be formulated by methods known to those skilled in the art. For example, as necessary, they can be prepared in the form of injectable sterile solutions or suspensions using water or another pharmaceutically acceptable liquid, and can be administered parenterally. For example, the antibodies to be included in the pharmaceutical compositions can be combined with acceptable carriers or media, specifically, sterile water, physiological saline, vegetable oils, emulsifiers, suspensions, surfactants, stabilizers, flavoring agents, excipients, solvents, preservatives, binders, or such, and mixed into a unit dose form required for generally accepted pharmaceutical practice. The phrase "pharmaceutically acceptable" indicates that the substance is inactive, and contains conventional substances used as diluents or vehicles for pharmaceuticals. Suitable excipients and their formulations are described, for example, in Remington's Pharmaceutical Sciences, 16$^{th}$ ed. (1980) Mack Publishing Co., ed. Oslo et al.

Physiological saline and other isotonic solutions containing glucose or adjuvants (for example, D-sorbitol, D-mannose, D-mannitol, and sodium chloride) can be used as aqueous solutions for injection. They can be used together with appropriate solubilizers such as alcohols, more specifically, ethanol and polyalcohols (propylene glycol, polyethylene glycol, and such), and non-ionic surfactants (Polysorbate 80™, HCO-50, and such).

Sesame oil or soybean oil can be used as an oleaginous liquid, and benzyl benzoate or benzyl alcohol can be used in combination as a solubilizer. Buffers (for example, phosphate buffer and sodium acetate buffer), soothing agents (for example, procaine hydrochloride), stabilizers (for example, benzyl alcohol and phenol), and antioxidants can be used for the formulations. Prepared injection solutions can be filled into appropriate ampules.

The administration is preferably parenteral administration, and specific examples include administration by injection, transnasal administration, transpulmonary administration, and transdermal administration. Examples of administration by injection include systemic and local administration by intravenous injection, intramuscular injection, intraperitoneal injection, subcutaneous injection, and such.

The pharmaceutical compositions contain a pharmaceutically effective amount of the active component (the above-mentioned antibody of the present invention). "Pharmaceutically effective amount (of a compound)" refers to an amount sufficient for treating and/or preventing disorders in which the antigens for the above-mentioned antibodies of the present invention play an important role. For example, "a pharmaceutically acceptable amount" may be an amount required for reducing Aβ accumulation, neutralizing Aβ-induced toxicity, reducing Aβ fibril formation, or such, thereby treating or preventing conditions caused by Alzheimer's disease, when the compound is administered to individuals (patients). The reduction or neutralization may be, for example, a reduction or neutralization of at least approximately 5%, 10%, 20%, 30%, 40%, 50%, 75%, 80%, 90%, 95%, 99%, or 100%.

Assessment for determining such a pharmaceutically effective amount of the above-mentioned antibodies of the present invention may be carried out using a standard clinical protocol including histopathological diagnosis.

A suitable administration method may be selected depending on the age and symptoms of the patient. The dosage of an antibody-containing pharmaceutical composition may be selected, for example, within the range of 0.0001 mg to 1000 mg per kilogram body weight for each administration. Alternatively, for example, the dosage for each patient may be selected within the range of 0.001 to 100,000 mg/body; however, the dosage is not necessarily limited to these ranges. Although the dosage and administration methods vary depending on the patient's body weight, age, symptoms, and such, one skilled in the art can appropriately select them. In the later-described animal experiments, the dosage was selected based on the high-dose intravenous immunoglobulin therapy (400 mg/kg) covered by health insurance for humans.

Furthermore, the present invention provides methods for detecting Aβ oligomers (examples include A40 (Aβ 1-40) and Aβ42 (Aβ 1-42) oligomers) in samples. Examples of "samples" of the present invention include samples collected from subjects. Specifically, the present methods include the step of detecting Aβ oligomers contained in a sample collected from a subject using an antibody of the present invention. Aβ oligomers in a sample can be detected using, for example, sandwich solid-phase enzyme immunoassay methods that use chemiluminescence (chemiluminescence ELISA), immunoprecipitation methods that use the obtained antibodies, immunoblotting, flow cytometry, mass spectrometry, and immunohistochemical analysis.

When Aβ oligomers are detected in a sample collected from a subject by the above-mentioned measurement methods, the subject may be an Alzheimer's disease patient. For example, when the amount of Aβ oligomers in a sample collected from a subject is compared with that from a healthy individual, and if the amount of Aβ oligomers is greater in the subject than in the healthy individual, the subject is determined to suffer from or be at a risk of developing Alzheimer's disease. Whether or not a subject suffers from or is at a risk of developing Alzheimer's disease is diagnosed usually by physicians (including individuals under instructions from physicians; same herein below). Data on the amount of Aβ oligomers in samples collected from a subject and a healthy individual, which are obtained by the present methods of diagnosis, will be useful for diagnosis by physicians. Therefore, the present methods of diagnosis can be expressed as methods of collecting and presenting data useful for diagnosis by physicians.

Specifically, the present invention provides methods for diagnosing whether or not a subject suffers from or is at a risk of developing Alzheimer's disease, wherein the methods comprise detecting Aβ oligomers in a sample collected from the subject using an antibody of the present invention.

Furthermore, the present invention provides methods of diagnosing whether or not a subject suffers from or is at a risk of developing Alzheimer's disease, which comprise the steps of:

(a) contacting a sample collected from a subject with an antibody of the present invention and an antibody that binds to an Aβ monomer; and (b) measuring the ratio of Aβ oligomer to Aβ monomer in the sample, wherein the subject is determined to suffer from or be at a risk of developing Alzheimer's disease, if the ratio measured in step (b) is higher than that of a healthy individual.

First, in the present methods, a sample collected from a subject is contacted with an antibody of the present invention and an antibody that binds to an Aβ monomer. Herein, "contact" may be carried out, for example, by adding each of the above-mentioned antibodies to a sample collected from a subject, which is placed in a test tube. In this case, the antibody is added suitably in the form of a solution, a solid obtained by freeze-drying, or such. When adding the antibody as an aqueous solution, the solution may purely contain the antibody alone, or may contain, for example, surfactants, excipients, coloring agents, flavors, preservatives, stabilizers, buffers, suspending agents, tonicity agents, binding agents, disintegrants, lubricants, fluidity promoters, or corrigents. The concentration at which the antibody is added is not particularly limited. For example, as with human immunoglobulin formulations, 500-mg, 1000-mg, and 2500-mg freeze-dried formulations and such may be suitably used.

Next, the ratio of Aβ oligomer to Aβ monomer (herein, this is also referred to as "O/M index") in the aforementioned sample is measured. To measure this ratio, the following method is suitably used. For example, as described below in the Examples, the measurement can be carried out using a method of comparing the oligomer and monomer ELISA values obtained from the same sample.

Then, this ratio is compared with the ratio for a healthy individual. When the ratio is higher in the subject than in the healthy individual, the subject is determined to suffer from or be at a risk of developing Alzheimer's disease.

The methods of diagnosis of the present invention can be performed both in vitro and in vivo, but they are preferably performed in vitro.

Preferably, the "sample" of the present invention is not particularly limited as long as it is a tissue derived from a subject. Examples include the brain (brain parenchyma, and such), organs, and body fluids (blood, cerebrospinal fluid, and such) of a subject. In the present invention, the sample is preferably blood (more preferably, plasma) or cerebrospinal fluid.

Furthermore, the present invention provides pharmaceutical agents for use in the above-mentioned methods of measuring Aβ oligomers in a sample, or methods of diagnosing whether or not a subject suffers from or is at a risk of developing Alzheimer's disease.

In the present invention, the pharmaceutical compositions comprising an antibody may be included in products and kits containing materials useful for treating pathological conditions of a subject. The products may comprise any labeled container for a compound. Suitable containers include bottles, vials, and test tubes. The containers may be formed from a variety of materials such as glass and plastic. The label on the container surface should indicate that the composition is used to treat or prevent one or more conditions of the disease. The label may also indicate descriptions for administration, and such.

In addition to the above-mentioned container, a kit containing a pharmaceutical composition comprising an antibody may optionally include a second container that stores a pharmaceutically acceptable diluent. The kit may further include other materials desirable from a commercial and user's standpoint, including other buffers, diluents, filters, needles, syringes, and package inserts with descriptions for use.

If necessary, the pharmaceutical compositions may be provided in a pack or dispenser device that may contain one or more unit dosage forms comprising an active ingredient. The pack may comprise metal or plastic foil, and, for example, it is a blister pack. The pack or dispenser device may be accompanied by instructions for administration.

In the above-mentioned pharmaceutical agents and kits, besides the antibody of the present invention that is an active ingredient, sterile water, physiological saline, vegetable oils, surfactants, lipids, solubilizing agents, buffers, protein stabilizers (BSA, gelatin, etc.), preservatives, blocking solutions, reaction solutions, reaction quenching solutions, reagents for treating samples, and such, may be mixed as necessary.

The present inventors showed that the antibodies of the present invention are effective for preventing Alzheimer's disease. That is, the present invention provides methods for suppressing the progression of Alzheimer's disease, wherein the methods comprise the step of administering to an individual affected with Alzheimer's disease, a composition comprising the above-mentioned antibody of the present invention and a pharmaceutically acceptable carrier.

The antibodies provided by the present invention are expected to greatly contribute to the establishment of preventive/therapeutic methods selective to molecules responsible for evoking pathological conditions of Alzheimer's disease, and the establishment of early diagnostic markers for Alzheimer's disease. The present inventors obtained evidence showing that, even in antibody therapy targeting pathological conditions in the brain, peripheral intravenous administration is sufficient and there is no need to consider brain transfer. Thus, the present invention is expected to rapidly accelerate the progress of antibody drugs for Alzheimer's disease.

All prior art references cited herein are incorporated by reference into this description.

EXAMPLES

Hereinbelow, the present invention is specifically described with reference to the Examples, but it is not to be construed as being limited thereto.
Methods
Preparation of Antigens (1A9 and 2C3)

Synthetic Aβ 1-42 (Peptide Institute, Inc., Osaka) was dissolved in distilled water or 10 mM phosphate buffer, and incubated at 37° C. for 18 hours. Then, the peptides were separated by SDS-PAGE (4-12% NuPAGE Tris-Glycine gel), and after visualization by CBB staining, just the Aβ 1-42 tetramer was excised without contamination of the Aβ 1-42 monomer.
Preparation of Antigens (4F7, 4H5, 5A5, 5A9, 6E4 and 6H4)

A fluorescent dye, 6-carboxytetramethylrhodamine (6-TAMRA) (SIGMA) was chemically linked to the N terminus of a synthetic Aβ 1-40 peptide (Peptide Institute, Inc.) to produce a modified Aβ. An oligomer-rich sample (Aβ 1-40 oligomer) was prepared by copolymerizing the modified Aβ and synthetic Aβ 1-40 peptide. It is preferable to adjust the conditions so that the fluorescence intensity determined by ThT assay, which is described below, is one-fourth or less the fluorescence intensity in the absence of modified Aβ. More specifically, it is preferred that 100 μM each of the modified Aβ and synthetic Aβ 1-40 peptide are mixed, and polymerized for 20 hours.
Preparation of Antibody-Producing Hybridomas Balb/c mice were immunized by injecting the antigen prepared by the method described above into their foot pads. Then, booster immunization was carried out six times. Hybridomas were prepared from inguinal lymph nodes by fusion with Sp2/O-Ag14 cells using Polyethylene Glycol 1500.
Antibody Isotyping Isotyping of purified immunoglobulins was carried out using a Serotec (Oxford, UK) mouse monoclonal antibody isotyping kit.
Dot Blot Analysis (Primary Screening)

The initial screening was carried out by dot blot analysis using a nitrocellulose membrane onto which 2.5 μl of Aβ 1-42 (2.5 μg/dot) pre-incubated for 18 hours was immobilized. Non-specific binding sites on the membrane were blocked with a phosphate buffer containing 5% low-fat milk, 1% BSA, and 0.05% Tween-20, and then the membrane was incubated with a culture supernatant. Aβ oligomer-binding antibodies in the culture supernatant were detected by horseradish peroxidase-labeled goat anti-mouse F(ab')$_2$ (1:3000; Amersham), and visualized using an enhanced chemiluminescence (ECL) kit and LAS3000 mini (Fujitsu, Tokyo, Japan). Among 400 clones, 16 clones positive in the dot blotting, including 1A9 and 2C3, were subjected to the secondary screening described below.
Immunoprecipitation and Immunoblot Analysis (Secondary Screening)

Immunoprecipitation experiments (Ghiso J, et al., Biochem J, 1993) were conducted using an Aβ oligomer-rich amyloid fraction (Matsubara E, et al., Neurobiol Aging, 2004) for the secondary screening to assess whether the 16 clones selected in the primary screening can capture Aβ oligomers in AD brain. A buffer-insoluble, formic acid-soluble fraction prepared from AD brain was incubated with a culture supernatant and Protein G-Sepharose. The immunoprecipitated Aβ oligomers were separated using an NuPAGE 4-12% Bis-Tris-Glycine gel, and transferred onto a nitrocellulose membrane or Immobilon P (Millipore) using 10 mM 3-cyclohexylamino-1-propane sulfonic acid (pH 11) containing 10% methanol at 400 mA for one hour. Non-specific binding sites on the membrane were blocked with a phosphate buffer containing 5% low-fat milk, 1% BSA, and 0.05% Tween-20 at room temperature for three hours. The immunoprecipitated Aβ oligomers were detected by immunoblotting using the 4G8 (1:1000) or 6E10 (1:1000) monoclonal antibody as described above. Two clones, 1A9 and 2C3, were selected from the 16 clones as candidates for therapeutic antibodies for Alzheimer's disease.

Antibodies

The 6E10 and 4G8 monoclonal antibodies (Covance Immuno-Technologies, Dedham, Mass.) recognize the epitopes at amino acid positions 1-16 and 17-24 of the human Aβ sequence, respectively. Polyclonal A11 which specifically recognizes Aβ oligomers was purchased from Biosource (Camarillo, Calif.). Alex Fluor(AF)488- or 594-conjugated goat anti-mouse IgG and Alex Fluor(AF)488-conjugated goat anti-rat IgG were purchased from Molecular Probes (Eugene, Oreg.). Anti-mouse IgG2b was purchased from Sigma (St. Louis, Mo.). An anti-synaptophysin antibody was purchased from Santa Cruz (Santa Cruz, Calif.), and an anti-drebrin antibody was purchased from MBL (Nagoya, Japan).

Size Exclusion Chromatography (SEC)

SEC was carried out to assess 1A9 and 2C3 for their size specificity. As previously reported (Matsubara E., et al., Neurobiol Aging, 25: 833-841, 2004), this method can selectively separate Aβ monomers and Aβ oligomers, or lipoprotein-bound Aβ and lipoprotein-free Aβ. The present inventors concentrated the culture supernatant from APP/PS1-overexpessing HEK293 cells about ten-fold using a Microcon 3 kDa molecular weight cut-off filter (Millipore Corp.). Then, this concentrate was fractionated into 28 one-milliliter fractions using a Superose 12 size exclusion column (1 cm×30 cm; Pharmacia Biotech., Uppsala, Sweden; flow rate of 0.5 ml/min) pre-equilibrated with a phosphate buffer. Half of each fraction was subjected to immunoprecipitation using 1A9 or 2C3. Aβ contained in the resulting immunoprecipitates was detected by immunoblotting using 4G8.

Cerebrospinal fluid (CSF) pooled from ten cases of Alzheimer's disease patients or age-matched healthy individuals, and lipoprotein-depleted CSF from the pools were also fractionated under the same conditions as described above. Aβ in the collected fractions was detected by ELISA analysis. To detect the lipid, the total cholesterol was enzymatically quantified using a standard kit (Wako, Osaka, Japan). Under the experimental conditions of the present inventors, the CSF lipoproteins were eluted at fractions 7 to 14, while fractions 15 to 28 contained cholesterol-free proteins.

Preparation of Seed-Free Aβ Solution

Synthetic Aβ 1-42 was dissolved at 250 μM in 0.02% ammonia water. Then, in order to prepare a seed-free Aβ solution, insoluble peptides, which may function as a seed, were precipitated by ultracentrifugation using an Optima TL ultracentrifuge (Beckman, USA) at 540,000×g for three hours. The resulting supernatant was collected, aliquoted, and stored at −80° C. until use. Samples were prepared by thawing the Aβ stock solutions immediately before use, and diluting them ten-fold with Tris-buffered saline (TBS; 150 mM NaCl and 10 mM Tris-HCl (pH 7.4)). The resulting 25 μM solutions were used in the experiments described below. Synthetic Aβ 1-40 (HCL form; Peptide Institute, Inc., Osaka) was prepared at 50 μM.

Aβ Incubation and ThT Assay (Yamamoto N, et al. J Biol Chem, 282: 2646-2655, 2007)

An Aβ solution (25 μM) was incubated in the presence of a predetermined concentration of an antibody at 37° C. for two or 24 hours. The ThT fluorescence intensity of the incubation mixture was determined using a fluorescence spectrophotometer (RF-5300PC; Shimadzu Co., Kyoto, Japan). The optimal fluorescence intensity was determined for Aβ amyloid fibrils at excitation and emission wavelengths of 446 and 490 nm, respectively, using 1.0 ml of a reaction mixture containing 5 μM ThT and 50 mM glycine-NaOH (pH 8.5). The fluorescence intensity was determined immediately after preparation of the mixture.

Furthermore, the activity of the 4F7, 4H5, 5A5, 5A9, 6E4, and 6H4 antibodies to suppress Aβ amyloid fibril formation was assessed by the following procedure. An Aβ 1-42 solution diluted to 12.5 μM with cell culture medium was incubated in the presence or absence of each antibody at 37° C. for 24 hours. The amount of formed amyloid fibrils was determined by the above-described ThT fluorescence intensity assay method.

Aβ-Induced Neurotoxicity Assay (Yamamoto N, et al. J Biol Chem, 282: 2646-2655, 2007)

Rat pheochromocytoma PC12 cells were cultured in Dulbecco's Modified Eagle Medium (DMEM) (Invitrogen, Carlsbad, Calif.) containing 10% heat-inactivated horse serum (Invitrogen) and 5% fetal bovine serum (FBS) (Invitrogen). In order to induce the differentiation into nerve cells, PC12 cells were plated at a density of 20,000 cells/cm$^2$ in culture dishes coated with poly-L-lysine (10 mg/ml), and cultured for six days in DMEM supplemented with 100 ng/ml nerve growth factor (NGF; Alornone Labs, Jerusalem, Israel) (PC12N). PC12N was exposed to 25 μM seed-free Aβ 1-42 or pre-incubated Aβ 1-42 in the presence or absence of antibody at 4° C. for 48 hours. The neurotoxicity induced by Aβ 1-42 was assessed by Live/Dead dual-color fluorescence assay according to the supplier's instructions (Molecular Probes, Eugene, Oreg.).

Furthermore, the activity of the 4F7, 4H5, 5A5, 5A9, 6E4, and 6H4 antibodies to neutralize Aβ-induced neurotoxicity was assessed by the method described below. First, human neuroblastoma cells (SH-SY5Y) were cultured for 24 hours in DMEM containing 10% FBS, at a density of 150,000 cells/well in 24-well plates. Then, the medium was replaced with serum-free culture medium containing Aβ 1-42 (12.5 μM) in the presence or absence of antibody, and the cells were cultured for another 24 hours. To determine the cytotoxicity induced by Aβ 1-42, the level of dead cell-derived LDH released into the medium was measured by a CytoTox96 kit (Promega).

Ultrafiltration and Molecular Sieve

In order to determine the size-dependent characteristics of neurotoxic Aβ oligomers, the four types of filtrates (<3 kDa, 3 to 10 kDa, 10 to 30 kDa, 30 to 100 kDa) and the retention solution (>100 kDa) were prepared from a 25 μM Aβ oligomer solution by sequential ultrafiltration using Microcon 3 kDa, 10 kDa, 30 kDa, and 100 kDa cut-off membranes. Each of the fractions was subjected to the A-induced neurotoxicity assay described above. PC12N was exposed to each fraction to identify the toxic fraction as described above. The distribution of the three-dimensional structures recognized by A11, 1A9, 2C3, and 4G8 was also identified by the dot blot analysis described above. The morphological characterization of the neurotoxic oligomers was performed by examining each fraction using an atomic force microscope.

Electron Microscopy (EM) and Atomic Force Microscopy (AFM)

Samples were diluted with distilled water and sprayed over carbon-coated grids to conduct electron microscopy. The grids were negatively-stained with 1% phosphotungstic acid and observed under a Hitachi H-7000 electron microscope (Tokyo, Japan) with an acceleration voltage of 77 kV. AFM assessment was carried out as recently reported. Drops of the samples were placed onto freshly cleaved mica. The mica was allowed to stand for 30 minutes and then washed with water, and the liquid samples were analyzed using Nanoscope IIIa (Digital Instruments, Santa Barbara, Calif., USA) set to the tapping mode (Tero, R, et al., Langmuir 20, 7526-7531, 2004). The cantilever used was OMCL-TR400PSA (Olympus, Japan).

Subject Tissues and Extraction

The present study was conducted based on autopsy cases (n=50; 26 male and 24 female cases) from the Tokyo Metropolitan Brain Bank for Aging Research of the Tokyo Metropolitan Institute of Gerontology (Itabashi, Tokyo, Japan). This research project was approved by the institutional ethical committees of the Faculty of Medicine, the University of Tokyo; the Tokyo Metropolitan Geriatric Hospital of the Tokyo Metropolitan Institute of Gerontology; and the National Center of Geriatrics and Gerontology. Details of subjects and sample collection have been reported (Katsuno T, Neurology, 64: 687-692, 2005). However, that study analyzed insoluble brain fractions, whereas in this research project (Katsuno T, Neurology, 64: 687-692, 2005), the present inventors analyzed soluble brain fractions, which remain uncharacterized in previous studies. Frozen tissue samples (the anterior portion of entorhinal cortex) were homogenized in nine volumes of Tris-buffered saline (TS) containing a protease inhibitor cocktail. The homogenates were ultracentrifuged at 265,000×g for 20 minutes. One-third aliquots (0.5 ml) of the resulting supernatants were subjected to immunoblot analysis.

Immunohistochemistry

The left brain hemispheres of Tg2576 mice were sliced into 30-µm-thick sagittal sections using a cryotome (RM 2145; Leica, Wetzlar, Germany), and stained with thioflavin S as previously described (Wyss-Coray et al., 2001). The formation of swollen dystrophic neurites was observed using an anti-synaptophysin antibody (Chemicon, Temecula, Calif.). The number of thioflavin S-positive plaques and synaptophysin-positive swollen dystrophic neurites was counted by observing four or five sections from the left brain hemisphere of each mouse at 40-fold magnification. To observe Aβ deposition, serial sections briefly pre-treated with formic acid or Protease K were stained using an Aβ immunostaining kit (Sigma, St. Louis, Mo.), and immuno-positive signals were visualized using an ABC elite kit (Vector Laboratories). Images of the cerebral cortex and hippocampus were recorded using a digital camera connected with a microscope, and analyzed using a simple PCI software (Compix Imaging System, Lake Oswego, Oreg.). The brain translocation of antibodies was observed using a confocal laser microscope (Carl Zeiss LSM510). The number of thioflavin S-positive plaques and synaptophysin-positive swollen dystrophic neurites was determined in a double blind manner.

Passive Immunotherapy and Behavioral Analysis

Three-month-old female non-transgenic (non-Tg) mice, and Tg2576 mice having and overexpressing the Swedish-type mutant human APP gene with dual mutations (K670N and M671L) derived from familial AD were purchased from Taconics (Germantown, N.Y., USA). These mice were reared until 13 months old in the animal facility of the present inventors. To determine whether the Alzheimer-like phenotype is prevented by passive immunotherapy, 1A9 or 2C3 (0.4 mg/kg/week), or PBS was administered into the caudal vein of four-month-old Tg2576, and the administration was continued until 13 months. The memory function was assessed at month 13 as previously described (Mouri A, FASEB J, 21: 2135-2148, 2007), based on the following four behavioral paradigms:

(1) Y-maze test for short-term memory;
(2) novel object recognition test;
(3) Morris water maze test; and
(4) contextual fear conditioning test.

Three days after the behavioral tests, the mice were sacrificed for biochemical and histological assessments. The experimental results were analyzed by one-way ANOVA and two-way ANOVA. Post-hoc analysis was carried out using Fisher test.

Separation and Removal of Lipoprotein

CSF was collected from 12 AD patients and 13 NC individuals. Then, lipoproteins were removed from 600 µl each of the CSF by preparative continuous density gradient ultracentrifugation according to a protocol reported previously (Matsubara E, et al., Ann Neurol, 45: 537-541, 1999). The density of CSF was adjusted to 1.25 g/ml with KBr. The CSF was ultracentrifuged at 100,000 rpm and 16° C. for eight hours using a Hitachi RP100AT centrifuge. Lipoproteins floating at a density of 1.25 g/ml and lipoprotein-depleted CSF (LPD-CSF) were subjected to ultrafiltration using a 3 kDa cut-off membrane (Microcon 3; Arnicon, Inc), and then frozen and stored, or stored at 4° C., until use.

Lipoproteins were also removed by affinity chromatography using PHML-LIPOSORB (Calbiochem, La Jolla, Calif.). Each sample (plasma or brain) and PHML-LIPOSORB (Calbiochem, La Jolla, Calif.) were combined at a ratio of 1.5:1, and mixed for 60 seconds. Then, the mixture was centrifuged at 3,000 rpm for ten minutes. The resulting supernatants (lipoprotein-free samples) were subjected to ELISA using 6E10 for the oligomers. The lipoprotein-bound samples were eluted from PHML-LIPOSORB using 20 mM sodium deoxycholate. The removal of specific lipoproteins was confirmed by agarose electrophoresis using 1% gel (Beckmann), followed by staining with FAST-RED 7B (Wako, Osaka, Japan).

Quantification of Human Aβ

Whole plasma and LPDP Aβ species were specifically quantified by sandwich ELISA as previously described (Matsubara E, et al., Ann Neurol, 537-541, 1999; Matsubara E, et al., Neurobiol Aging, 25: 833-841, 2004). To analyze brain Aβ species, soluble Aβ species in 100 µl of buffer were directly subjected to ELISA, while insoluble Aβ samples extracted with 70% formic acid were neutralized with 1 M Tris-HCl (pH 8.0) and diluted 1,000-fold prior to ELISA. The values obtained by the assay were normalized using the brain wet weight, and ultimately presented in pmol/g. Normalization among plates was done by including the three standard plasma samples in all three plates.

Aβ Oligomer-Specific ELISA

Chemiluminescence-based sandwich solid-phase enzyme immunoassay (chemiluminescent ELISA) was used to specifically detect oligomeric Aβ but not monomeric Aβ. Microplates were coated with monoclonal 1A9 (IgG2b isotype) or 2C3 (IgG2b isotype), or a mixture of 1A9 and 2C3. 100 µl of a sample (brain or cerebrospinal fluid) was added and incubated continuously for 24 hours at 4° C. Then, horseradish peroxidase-conjugated BA27 Fab' fragment (anti-Aβ 1-40 specific to Aβ 40; Wako pure chemical, Osaka, Japan) or horseradish peroxidase-conjugated BCO5 Fab' fragment (anti-Aβ 35-43 specific to Aβ 42; Wako pure chemical, Osaka, Japan) was added and incubated at 4° C. for 24 hours. The chemiluminescence generated using SuperSignal ELISA Pico Chemiluminescent Substrate (Pierce, Rockford, Ill., USA) was quantified by a Veritas Microplate Luminometer (Promega).

To assess the in vivo efficacy of the peripheral administration of monoclonal 1A9 and 2C3, plasma and organ samples were collected from administered mice and analyzed for Aβ oligomers by ELISA using HRP-labeled 6E10 (Senetek PLC, Napa, Calif., USA) specific to the human oligomers. High-sensitivity detection was achieved by using the above-described chemiluminescent system. To avoid interference by lipoprotein-bound Aβ monomers, the present inventors pre-treated plasma and organ samples using PHML-LIPOSORB in the same way as described above. The resulting lipoprotein-depleted samples were used for the assay.

Inhibition ELISA

Aβ oligomers used in this assay were prepared by diluting synthetic Aβ 1-40 (HCl form) to a concentration of 0.1 mg/ml with PBS and incubating this at 37° C. for one hour. Meanwhile, Aβ monomers were prepared by diluting synthetic Aβ 1-40 (TFA form) to a concentration of 0.1 mg/ml with PBS. Aβ oligomers were immobilized onto 96-well immunoplates at 400 ng/well, and then the plates were blocked with BSA. Next, the Aβ monomers or oligomers stepwise-diluted in the range of 100 pg/ml to 100 μg/ml were reacted with the 4F7, 4H5, 5A5, 5A9, 6E4, or 6H4 antibodies, or the control anti-Aβ antibodies (4G8 and 6E10). After incubation for two hours, the mixtures were added to the above-described 96-well immunoplates, and incubated at room temperature for ten minutes. The binding of immobilized Aβ oligomers to each of the antibodies was detected by measuring the absorbance at 450 nm in the color development reaction using an HRP-labeled anti-mouse IgG antibody and a TMB solution.

Example 1

Preparation of Aβ Oligomer-Specific Monoclonal Antibodies (1A9 and 2C3)

Figure 1:
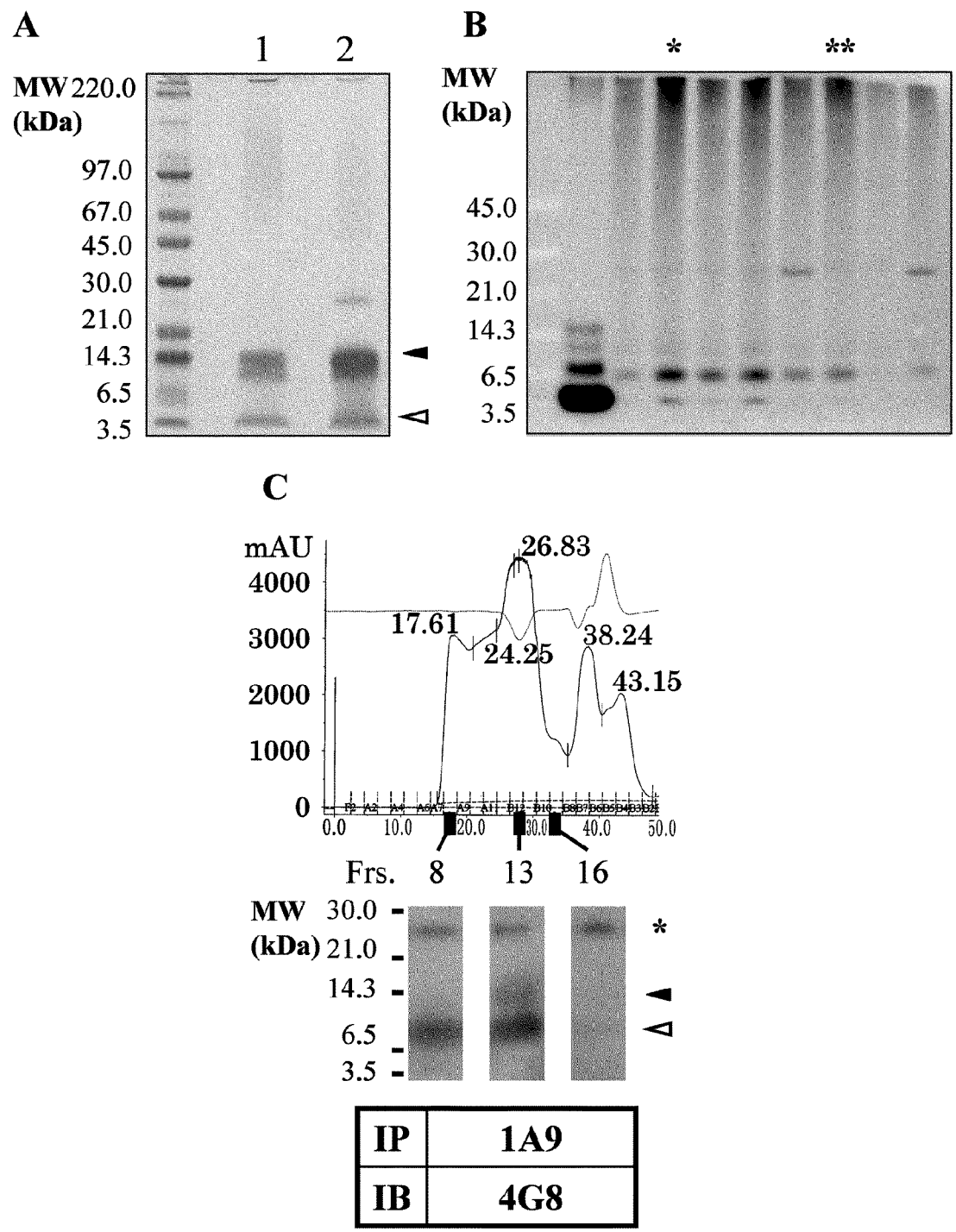
FIG. 1 presents photographs and a graph showing the results of production and characteristic determination of oligomer-specific antibodies. A: Electrophoresis of immunogens. The Aβ 1-42 tetramer (black arrowhead) which is free of contamination of the Aβ 1-42 monomer (outlined arrowhead) was isolated using SDS-PAGE. Lane 1: Aβ 1-42 dissolved in 10 mM phosphate buffer; and Lane 2: Aβ 1-42 dissolved in distilled deionized water. B: Aβ amyloid, which is insoluble in a buffer but can be extracted using formic acid from the brain of Alzheimer's disease patients, was immunoprecipitated using the supernatant of a positive hybridoma cell culture, and the immune complex was selectively separated using protein-G agarose (Amersham). Nine clones were tested; lane 2 (asterisk) is 1A9 and lane 6 (double asterisk) is 2C3. C: Elution profile of SEC of a conditioned medium. Among the 24 SEC-collected fractions, fractions 8, 13, and 16 were subjected to 1A9 immunoprecipitation. Aβ immunoreactivity was detected using 4G8. The black arrowhead indicates the trimer and the outlined arrowhead indicates the dimer. Asterisk (*) indicates the anti-mouse IgG light chain.

Aβ oligomers and monomers co-exist in a solution. Thus, it is essential to remove Aβ monomers for preparation of antigens to produce Aβ oligomer-specific antibodies. As shown in FIG. 1A, the present inventors succeeded in isolating SDS-stable Aβ tetramers without contamination of Aβ monomers by SDS-PAGE. After in vivo immunization with the isolated Aβ tetramers, positive hybridoma clones were selected by two-step screening using dot blot analysis followed by immunoprecipitation. Among 400 clones subjected to dot blot analysis, 16 clones were determined to be positive (positivity rate=4%). To assess the specificity of the isolated positive clones to the oligomers, a phosphate buffer-insoluble and formic acid (FA)-soluble amyloid fraction derived from AD brain (Matsubara E et al., Neurobiol Aging, 25: 833-841, 2004) was analyzed by immunoprecipitation using the cell culture supernatants of the positive hybridomas (FIG. 1B). The Aβ dimer, a smaller amount of the trimer, and a high-molecular-weight smear characteristic to aggregated Aβ molecular species were detected by immunoblot analysis using anti-Aβ monoclonal 4G8. A very small amount of Aβ monomers dissociated in the presence of SDS was also detected. To further confirm the existence of three-dimensional structures recognized by native 1A9 and 2C3 (i.e., oligomers), the present inventors detected the oligomers in conditioned medium (CM) of human embryonic kidney (HEK) 293 cells transfected with mutant PS1 cDNA (Nakaya Y et al., J Biol Chem, 280: 19070-19077, 2005). The present inventors fractionated HEK293 CM by SEC, and then identified the oligomers. As reported previously (Matsubara E et al., Neurobiol Aging, 25: 833-841, 2004; Yamamoto N, et al., J Biol Chem, 282: 2646-2655, 2007), this method can effectively separate the oligomers (fractions 8 to 13) from monomers (fractions 14 to 20). When immunoprecipitated with monoclonal 1A9, SDS-stable Aβ dimers secreted into CM were precipitated in fraction 8 (>680 kDa); SDS-stable Aβ dimers and trimers were precipitated in fraction 13 (17 to 44 kDa); and a very small amount of the dimers was precipitated in fraction 16 (FIG. 1C). Similar results were obtained when immunoprecipitation was carried out using 2C3 (data not shown). These data demonstrate that monoclonal 1A9 and 2C3 are exactly specific to Aβ oligomers but do not recognize Aβ monomers.

Example 2

The Anti-Neurotoxic Activity of Monoclonal 1A9 and 2C3

Figure 2:
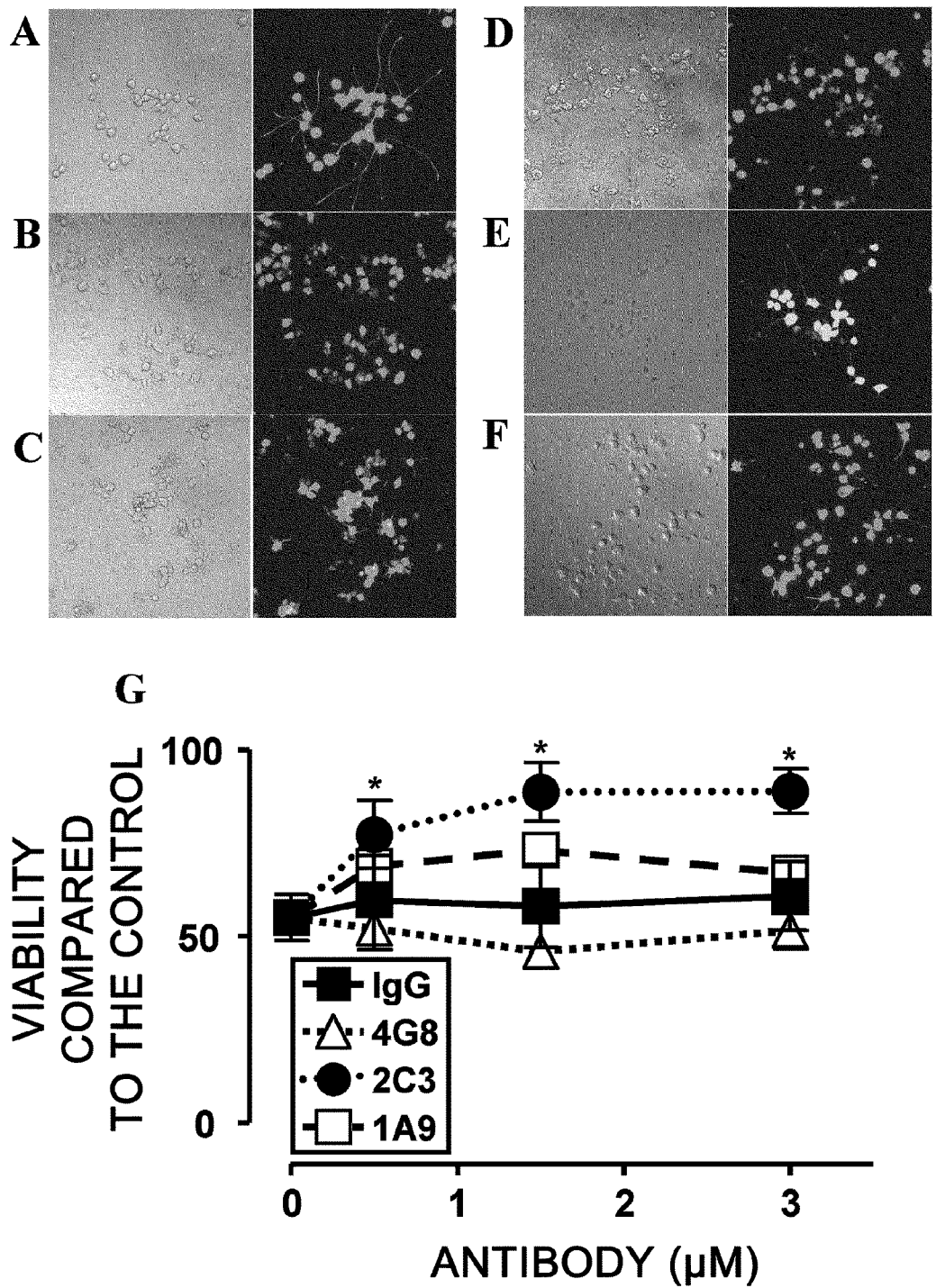
FIG. 2 presents photographs and a graph showing the antitoxic activity of 1A9 and 2C3. A to F: Representative images of NGF-treated PC12 (PC12N) cells, which were exposed to seed-free Aβ 1-42 at 37° C. for 48 hours in the presence or absence of the antibodies (left half of each panel). Representative calcein AM/PI staining where live cells were stained green and dead cells were stained red (right half of each panel). G: The viability of cells exposed to seed-free Aβ 1-42 (25 μM) with the following antibodies: non-specific IgG2b (filled square); 4G8 (open triangle); 1A9 (open square); and 2C3 (filled circle).

To assess whether monoclonal 1A9 and 2C3 can prevent Aβ-induced neurotoxicity, NGF-differentiated PC12 cells (PC12N) were incubated with 25 μM seed-free Aβ 1-42 (ThT-negative 540,000×g supernatant) in the presence or absence of the monoclonal antibodies (mAbs) at 37° C. for 48 hours. The viability of nerve cells was determined by LIVE/DEAD assay (FIG. 2). Nerve cell death was detected at a significantly high level (50%) in the presence of Aβ 1-42 (FIGS. 2B and 2G), as compared to the control assay (FIG. 2A). Non-specific IgG2b (FIGS. 2C and 2G) could not inhibit the Aβ 1-42-induced neurotoxicity under the same conditions. The commercially available Aβ-specific monoclonal antibody 4G8 (IgG2b isotype; FIGS. 2D and 2G) had a tendency to enhance the toxicity. Monoclonal 2C3 (IgG2b isotype; FIGS. 2F and 2G) neutralized the neurotoxicity of Aβ 1-42 almost completely in a concentration-dependent manner. Thus, the de novo-formed neurotoxic three-dimensional structure recognized by 2C3 was speculated to take an oligomer form. Meanwhile, the anti-neurotoxic activity of 1A9 (IgG2b isotype; FIGS. 2E and 2G) falls between the anti-neurotoxic activity of 2C3 and non-specific IgG2b. This suggests that the three-dimensional structure recognized by 1A9 is structurally different from the 2C3-recognized oligomers.

Example 3

Figure 3:
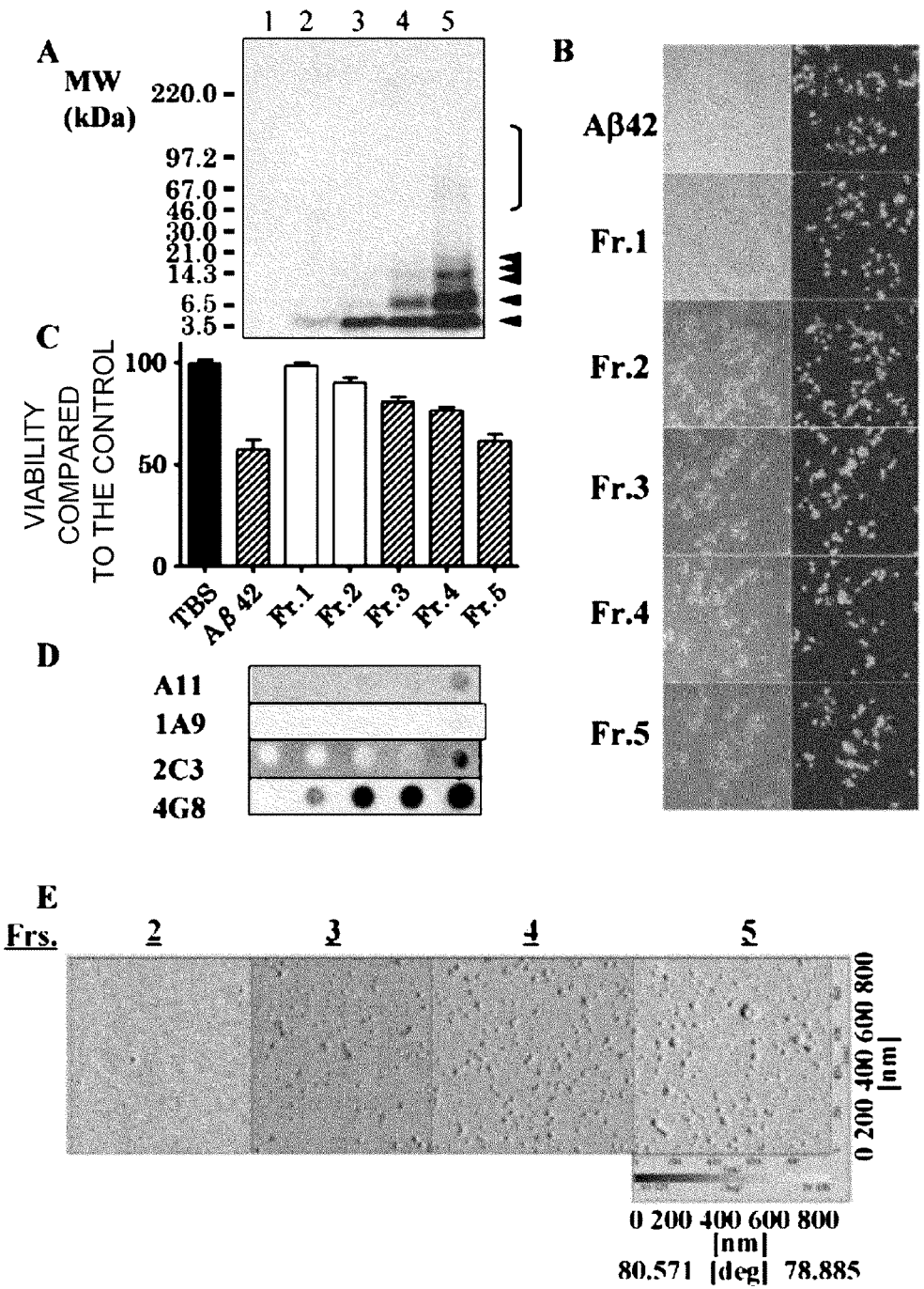
FIG. 3 presents photographs and a graph showing the size and morphological characteristics of the toxic Aβ assemblies targeted by 1A9 and 2C3. A: The 540,000×g supernatant of Aβ 1-42 (25 μM) was subjected to a continuous molecular sieving process using ultrafiltration membranes having a molecular weight cutoff value of 3, 10, 30, and 100 kDa (Microcon). The four types of filtrates thus fractioned were named as follows: fraction 1 (<3 kDa), fraction 2 (3 to 10 kDa), fraction 3 (10 to 30 kDa), fraction 4 (30 to 100 kDa); and fraction 5 (>100 kDa) which was finally retained. The presence of Aβ 1-42 in each of the above-mentioned fractions was detected by 4G8 immunoblotting. B: Representative images of NGF-treated PC12 (PC12N) cells treated with the five fractions at 37° C. for 48 hours. The toxicity of each fraction was evaluated as described above for FIG. 2. C: The viability of cells treated with the 540,000×g supernatant of Aβ 1-42 and the five fractions (fractions 1 to 5). Similar results were obtained from two independent experiments. The values are presented in percentage (mean±SD) with respect to the control. D: Dot blot analysis of the five fractions (fractions 1 to 5). The blots were reacted with A11, A9, 2C3, and 4G8. E: AFM images of the five fractions. In fraction 5 (Fr. 5) that had the strongest toxicity, ring-shaped and bead-shaped structures were observed in addition to granular molecules.

Currently, the determination of the precise size and conformation of neurotoxic Aβ 1-42 oligomers is one of the most urgent issues and which is subjected to intense competition. The present inventors succeeded in isolating soluble neurotoxic Aβ 1-42 molecular species and fractionating the species into the following five fractions by ultrafiltration and molecular sieving (UC/MS) (FIG. 3A):
fraction 1, filtrate of <3 kDa (lane 1);
fraction 2, filtrate of 3 to 10 kDa (lane 2);
fraction 3, filtrate of 10 to 30 kDa (lane 3);
fraction 4, filtrate of 30 to 100 kDa (lane 4); and
fraction 5, retention solution of >100 kDa (lane 5).

The immunoblot analysis using monoclonal 4G8 (FIG. 3A) revealed that:
fraction 1 does not contain Aβ (lane 1);
fraction 2 contains Aβ monomers (lane 2);

fraction 3 contains Aβ monomers and a small amount of Aβ dimers (lane 3);

fraction 4 contains Aβ monomers to pentamers (lane 4); and fraction 5 contains Aβ monomers to pentamers, and molecules of 45 to 160 kDa (lane 5).

These data suggest that 2% SDS depolymerizes high-molecular-weight (HMW) Aβ oligomers into Aβ monomers and low-molecular-weight (LMW) Aβ oligomers. To assess the size distribution of toxic Aβ 1-42, the present inventors measured the biological activity of each fraction incubated with PC12N at 37° C. for 48 hours. As shown in FIGS. 3B and 3C, it was demonstrated that: fraction 1 was non-toxic, and fraction 2 had a very weak toxicity, suggesting that Aβ monomers and dimers are unlikely to be toxic. Fractions 3 to 5 were significantly toxic (one-way ANOVA; $p<0.0001$), suggesting that the size of neurotoxic oligomers theoretically corresponds to the size of trimers or higher-molecular-weight polymers. The dot blot analysis using the oligomer-specific A11 antibody demonstrated that the above-mentioned three neurotoxic fractions (3 to 5) were positive for A11, supporting the evidence that the neurotoxic molecules are oligomeric (FIG. 3D). The 2C3-recognized oligomers were detected in fractions 4 and 5 (FIG. 3D). Thus, 2C3 was demonstrated to actually react with neurotoxic Aβ oligomers (>30 kDa). Furthermore, the majority of the 2C3-recognized oligomers was detected in fraction 5 (>100 kDa) that was the most toxic, and thus the 2C3-recognized oligomers having a molecular weight over 100 kDa were considered to show a strong neurotoxicity (FIG. 3D). Meanwhile, only an extremely small amount of the 1A9-recognized oligomers was distributed in fraction 5 that was the most toxic. This is consistent with the result that the neutralization of neurotoxicity by 1A9 was insufficient (FIGS. 2E and 2G). By contrast, monoclonal 4G8 having no anti-neurotoxic activity detected the Aβ species distributed in all of the fractions (FIG. 3D). This suggests the possibility that non-toxic and toxic oligomers of the same size co-exist.

To further assess the toxicity-structure correlation, each fraction was subjected to atomic force microscopy (AFM). The presence of globular particle morphology consistent with the fraction size was detected in the three neurotoxic fractions. FIG. 3E shows the atomic force microscopic images of non-toxic fraction 2 (Fr. 2), toxic fractions 3 (Fr. 3) and 4 (Fr. 4), and the most toxic fraction 5 (Fr. 5). The formation of many granular polymer molecules was clearly observed in the toxic fractions. In particular, fraction 5 was revealed to contain heterogeneous toxic molecules including bead-shaped and ring-shaped molecules in addition to various large and small granular molecules.

Example 4

The Activity of 1A9 and 2C3 to Suppress Aβ Amyloid Fibril Formation

Figure 4:
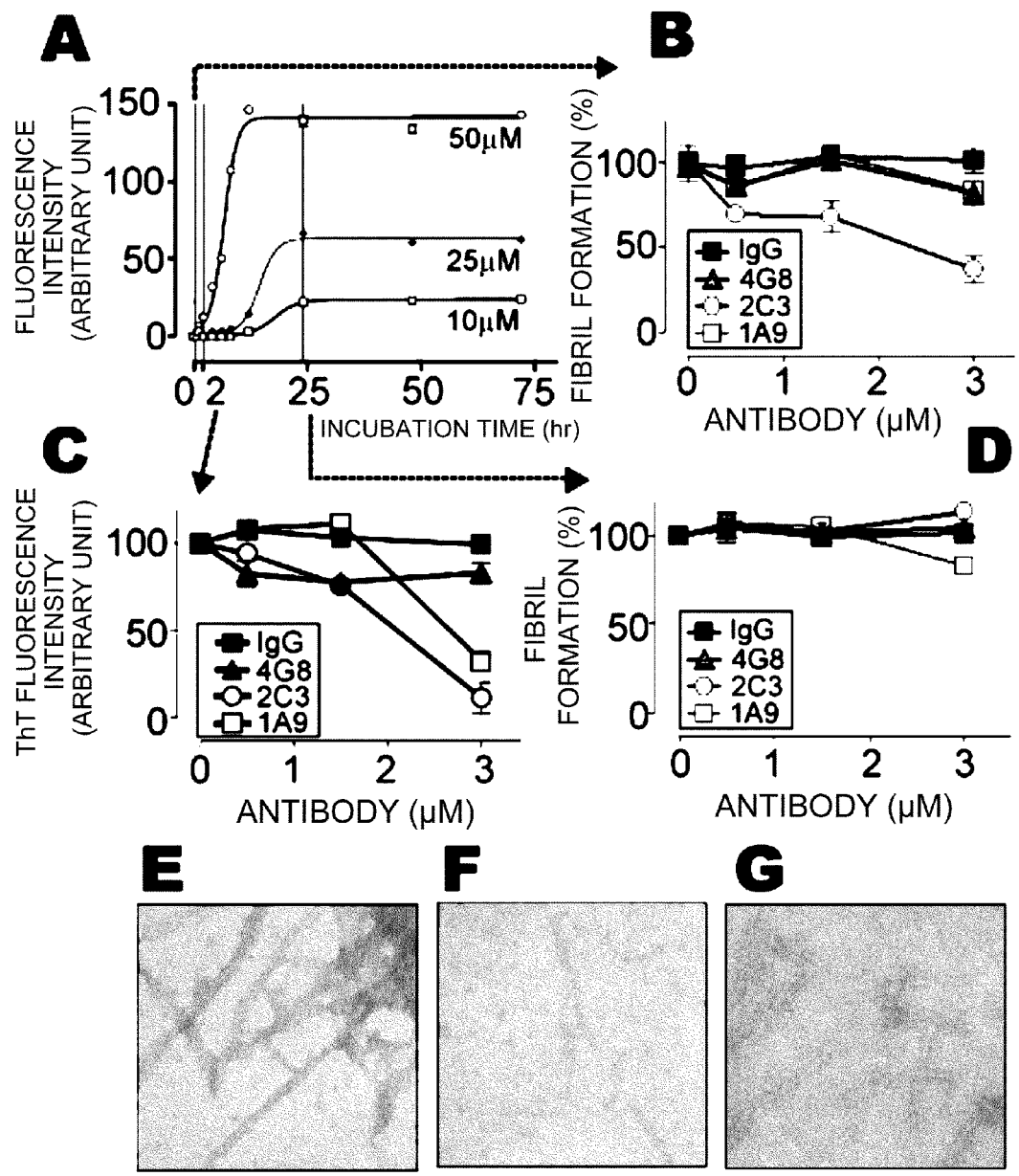
FIG. 4 presents photographs and graphs showing the activity of 1A9 and 2C3 to suppress Aβ amyloid fibril formation. A: Amyloid fibril formation of Aβ 1-42 at various concentrations (10 μM (open square), 25 μM (filled diamond), and 50 μM (open circle)) was monitored by ThT assay at 37° C. for up to 72 hours. B: Coexisting antibody dose-dependent inhibition of amyloid fibril formation of Aβ 1-42 was observed for 2C3 (open circle). In contrast, the 1A9 (open square), 4G8 (filled triangle), and non-specific IgG (filled square) antibodies did not inhibit fibril-forming assembly of seed-free Aβ 1-42 (ThT-negative 540,000×g supernatant). C: Coexisting antibody dose-dependent inhibition of fibril-forming assembly of Aβ 1-42 was observed for 2C3 (open circle), and nearly complete inhibition was observed also for 1A9 (open square) at 3 μM. D: None of the test antibodies added after a 24-hour pre-incubation for Aβ 1-42 amyloid fibril formation could dissolve nor disassemble the Aβ 1-42 amyloid fibrils. E to G: EM images of Aβ 1-42 in the absence (Panel E) and presence of 2C3 (Panel F) and 1A9 (Panel G).

Next, the present inventors assessed the activity of 1A9 and 2C3 to suppress Aβ amyloid fibril formation. The formation of Aβ 1-42 amyloid fibrils (at 0, 10, 25, and 50 μM) was assessed by measuring the ThT fluorescence for 72 hours at 37° C. Under the conditions used by the present inventors, seed-free Aβ 1-42 (ThT-negative supernatant fraction obtained by ultracentrifugation at 540,000×g) was polymerized into amyloid fibrils by nucleation-dependent polymerization (FIG. 4A). To assess the activity of 1A9 and 2C3 to suppress Aβ amyloid fibril formation, the present inventors incubated 25 μM seed-free Aβ 1-42 in the presence or absence of the antibodies at 37° C. for 48 hours. As shown in FIG. 4B, the ThT fluorescence intensity was altered in a 2C3 concentration-dependent manner, while none of monoclonal 1A9 and 4G8 and non-specific IgG2b altered the florescence intensity. Meanwhile, when Aβ was polymerized by incubation for two hours, 1A9, as well as 2C3, showed the activity to almost completely suppress the fibril formation (FIG. 4C). Since the activity to suppress Aβ amyloid fibril formation was detected even when the molar ratio of 2C3 to Aβ was low, 2C3 was inferred to have the activity to inhibit the polymerization nucleus formed de novo or the seed function at an early stage of Aβ 1-42 amyloid fibril formation. Similar results were obtained by morphological observation. As shown in FIG. 4E (Aβ 42 alone) and FIG. 4F (Aβ 42+2C3, 25:3), electron microscopy (EM) demonstrated that the formation of Aβ amyloid fibrils was partially inhibited in the presence of monoclonal 2C3, while only a weak inhibitory effect was produced in the presence of 1A9 (FIG. 4G). Meanwhile, none of the test antibodies exhibited the effect of lysing or depolymerizing Aβ 1-42 amyloid fibrils that were formed by incubation for 24 hours (FIG. 4D).

Example 5

Toxicity-Related Oligomers Targeted by 1A9 and 2C3

Figure 5:
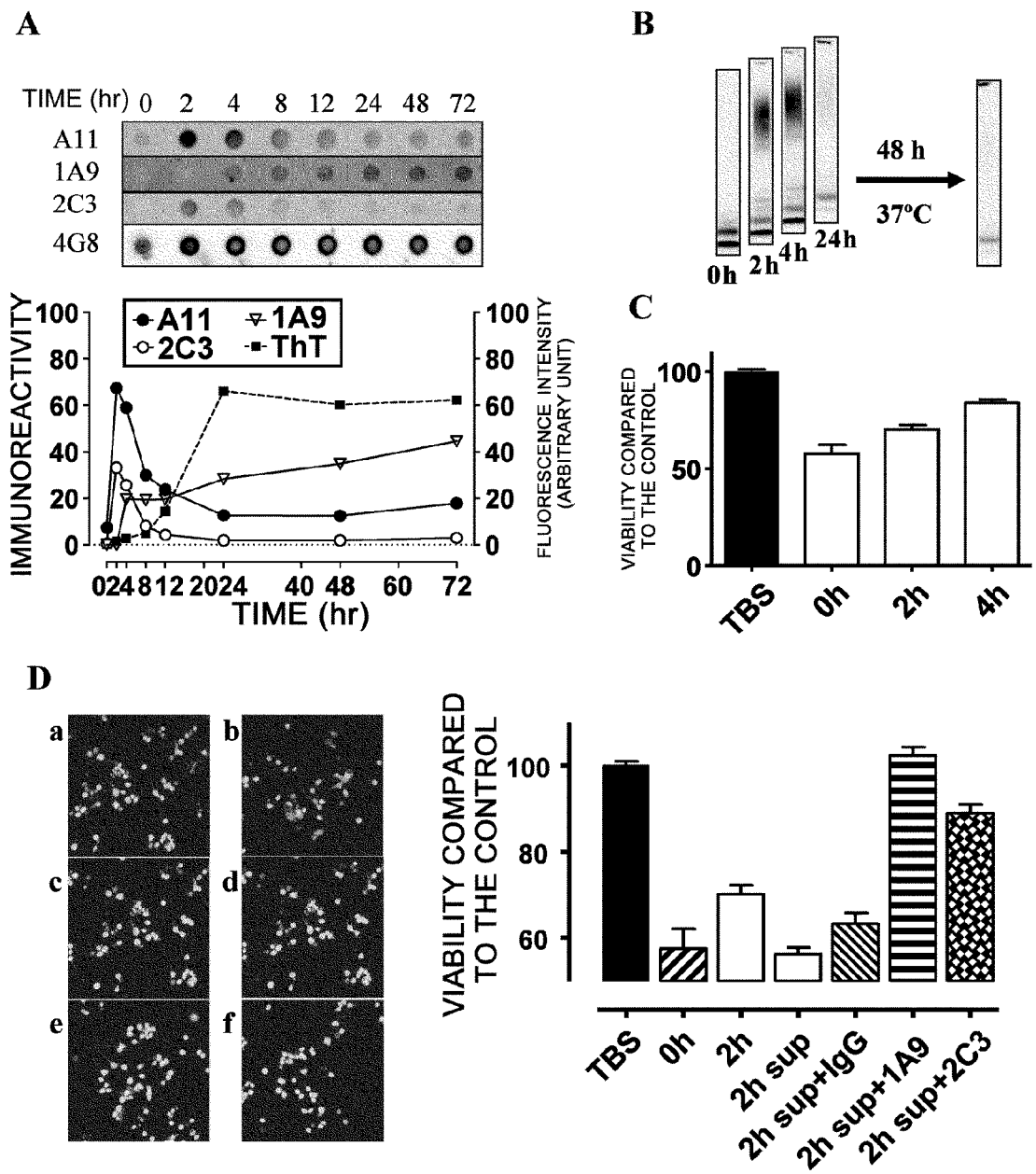
FIG. 5 presents photographs and graphs on toxicity-related Aβ 1-42 oligomers. A: Dot blot assay (upper half of Panel A): Aβ 1-42 monomers (25 μM) were incubated for a specified time (0 to 72 hours) at 37° C., and immobilized onto a nitrocellulose membrane, and subjected to dot blot assay that uses A11, 1A9, 2C3, or 4G8. The emergence of immunoreactivity-positive structures for each antibody was tested. Immunoreactivity intensity analysis (lower half of Panel A): The results of dot blot assay were analyzed semiquantitatively using the Multi Gauge v 3.0 software (Fuji Film, Tokyo). To correlate the oligomer formation and amyloid fibril formation, the ThT fluorescence value (the right Y axis) was overlaid on the same time axis. B: The Aβ 1-42 assembly after 0-, 2-, 4-, and 24-hour incubation at 37° C., and the change in Aβ 1-42 assembly after further 48-hour incubation. The Aβ 1-42 assembly was detected by 4G8 immunoblotting. C: The toxic activity of the above-mentioned various Aβ 1-42 assemblies. The viability of nerve cells was determined by the LIVE/DEAD assay as described for FIG. 2. D: The anti-neurotoxic activity of 1A9 and 2C3 was evaluated using various Aβ assemblies (the Aβ 1-42 assemblies formed at 37° C. for 0 and 2 hours ("0 h" and "2 h"); and the ThT-positive supernatant collected after ultracentrifugation at 540,000×g for two hours ("2 h sup")). Representative images of PC12N cells exposed to various Aβ 1-42 assemblies in the absence or presence of the antibodies are shown in the left half of Panel D (a: "0 h"; b: "2 h"; c: "2 h sup"; d: "2 h sup"+IgG2b; e: "2 h sup"+1A9; f: "2 h sup"+2C3). The viability of cells exposed to various Aβ 1-42 assemblies in the absence or presence of the antibodies is presented in percentage (mean±SD) with respect to the control, and this is shown in the right half of Panel D. Compared to the "0 h" Aβ 1-42 assembly, the "2 h" Aβ 1-42 assembly lowered the neurotoxicity. "2 h sup" recovered the neurotoxicity to a degree similar to that of the "0 h" Aβ 1-42 assembly. Non-specific IgG2b could not block the neurotoxicity induction of the "2 h sup" Aβ 1-42 assembly. Monoclonal 1A9 completely inhibited the "2 h sup"-induced neurotoxicity, while the ability of 2C3 to inhibit the toxicity was slightly inferior. In the experiments using the two monoclonal antibodies (mAbs), the antitoxic activity of the mAbs was observed at a mAb:Aβ mole ratio of 1:<25 to 50. This suggests that structurally different 1A9- and 2C3-recognized oligomeric assemblies exist at a relatively low concentration.

To elucidate the structural and kinetic connection between the Aβ 1-42 oligomerization and amyloid fibril formation, the polymerization time course was analyzed by dot blotting using A11, 1A9, 2C3, and 4G8. As shown in FIG. 5A, the majority of A11 antibody-reactive oligomers was formed during the lag time phase of polymerization (0 to 8 hours), and the ThT fluorescence intensity was relatively weak. During the next fibril extension phase (8 to 24 hours), the level of A11-immunoreactive oligomers reached a plateau, and then was constant (about 20% of the peak level) until 72 hours (plateau phase). It has been demonstrated that, since the anti-oligomer A11 antibody does not recognize amyloid fibrils, the Aβ oligomer formation can be specifically observed using the antibody (Kayed R, et al., Science 300, 486-489, 2003). Hence, the present results suggest that the Aβ oligomer formation precedes amyloid fibril formation, and there is an oligomerization state that does not directly enter the amyloid fibril formation pathway. The 2C3-recognized oligomers were kinetically similar to the A11-recognized oligomers, but not the 1A9-recognized oligomers. The 1A9-recognized oligomers were detected only after four hours, and then the immunoreactivity to 1A9 increased twofold over time. This suggests that the 1A9-recognized oligomers are slowly formed. Meanwhile, it was revealed that the 2C3-recognized oligomers are transiently increased during the lag time phase (0 to 8 hours), and then exist at a very low level (less than 5%) in a oligomerized state from 8 to 72 hours. The above-described data obtained by the present inventors suggest the possibility that the A11-, 1A9-, and 2C3-recognized oligomers have structurally and immunologically different conformations or stability, and the 2C3-recognized oligomers are relatively unstable as compared to the 1A9-recognized oligomers.

To characterize the de novo toxic polymerization state, PC12N were exposed at 37° C. for 48 hours to seed-free Aβ 1-42 (0 hour), or Aβ 1-42 pre-incubated for two, four, or 24 hours (FIG. 5B), and the neurotoxic activity was assayed. As shown in FIG. 5B, the immunoblotting analysis using 4G8 revealed that the monomers, dimers, and timers exist even at the 0 hour time point. The pre-incubation of two or four hours resulted in a high-molecular-weight (HMW) smear pattern of 45 to 160 kDa, in addition to the monomers to pentamers. At the time point of 24 hours, the HMW smear was dramatically reduced, and there were two types of major components: a high-molecular-weight species that could not enter the gel and thus remained in the well, and a small amount of the monomers. The HMW smear disappeared after further incubation at 37° C. for 48 hours. As shown in FIGS. 3A and 5C, the molecular sieve experiment revealed that seed-free Aβ 1-42 is converted into molecular species of 100 kDa or more, and exhibits the strongest toxicity. By SDS-PAGE, it was demonstrated that the toxic molecules include molecular species showing a high-molecular-weight (HMW) smear pattern of 45 to 160 kDa, in addition to the monomer to pentamer species, and the toxic polymers can be easily depolymerized into low-molecular-weight species in the presence of SDS. However, when seed-free Aβ 1-42 was pre-incubated for two and four hours, the neurotoxic activity of de novo-formed Aβ oligomers was reduced by about 12.5% and 26%, respectively (FIG. 5C). This result suggests that the level of de novo-formed Aβ oligomers in the early period of Aβ polymerization is a determining factor for neurotoxicity, and that the formation reaches a peak in the period of zero to two hours, and then the level of formed Aβ oligomers reduces over time. Alternatively, there is a possibility that nuclei for the de novo polymerization of Aβ amyloid fibrils, or amyloid fibrils themselves have the neurotoxicity-neutralizing activity. The present inventors incubated Aβ 1-42 for two hours, and then removed insoluble Aβ polymerization nuclei and amyloid fibrils by ultracentrifugation for three hours at 540,000×g. The supernatant and pellet obtained by ultracentrifugation at 540,000×g exhibited similar levels of thioflavin T signals, suggesting that the 540,000×g supernatant contains soluble ThT-positive Aβ polymers (The ThT binding indicates structural changes to form a P sheet-rich structure, but not fibril formation). The neurotoxicity was restored and enhanced when PC12N was exposed to the soluble polymers (FIG. 5D). This suggests that insoluble Aβ 1-42 itself has the anti-toxic activity. Under the conditions described above, monoclonal 1A9 completely neutralized the neurotoxicity induced by soluble Aβ oligomers enriched in β sheet structures, and this neutralizing activity was greater than that of 2C3. Meanwhile, non-specific IgG2b has no effect on the viability of cultured PC12N. Accordingly, it is speculated that neurotoxic 1A9-recognized polymers are basically soluble toxic oligomers that have been slightly stabilized due to some structural change, while neurotoxic 2C3-recognized polymers are basically short-lived oligomeric intermediates that are very unstable due to drastic structural changes during the early stage of polymerization process.

Example 6

Monoclonal 1A9 and 2C3 Recognize Aβ Oligomers in the Brain Parenchyma

The present inventors demonstrated the specificity and biological activity of 1A9 and 2C3. Furthermore, the inventors detected 1A9 and 2C3 polymers in the brain by immunohistochemistry. The present inventors performed conventional immunohistochemistry methods to enhance immune reaction by formaldehyde fixation, and formic acid, SDS, or microwave treatment of brain sections. The two antibodies exhibited no immunoreactivity to AD brain by any one of the enhancement methods. Thus, the present inventors pre-treated the sections with Protease K, which is known to improve immunostaining (Wrzolek M A, et al., Am J Pathol, 141: 343-355, 1992). As a result, many senile plaques were stained with 1A9 (FIG. 6A), 2C3 (FIG. 6B), and A11 (FIG. 6C). Together with the finding from the in vitro experiments by the present inventors that Aβ amyloid fibrils neutralize the Aβ oligomer-induced neurotoxicity, the result described above suggests that a senile plaque serves as a defensive reservoir to isolate and store Aβ oligomers, and thus the interior of the reservoir is hardly accessible for antibodies. Indeed, immunoprecipitation using 1A9 and 2C3 demonstrated that amyloid fractions composed of senile plaques contain Aβ oligomers recognized by the two antibodies. Thus, the hypothesis of the present inventors was proven to be consistent with the in vivo finding (see FIG. 1B).

Figure 6:
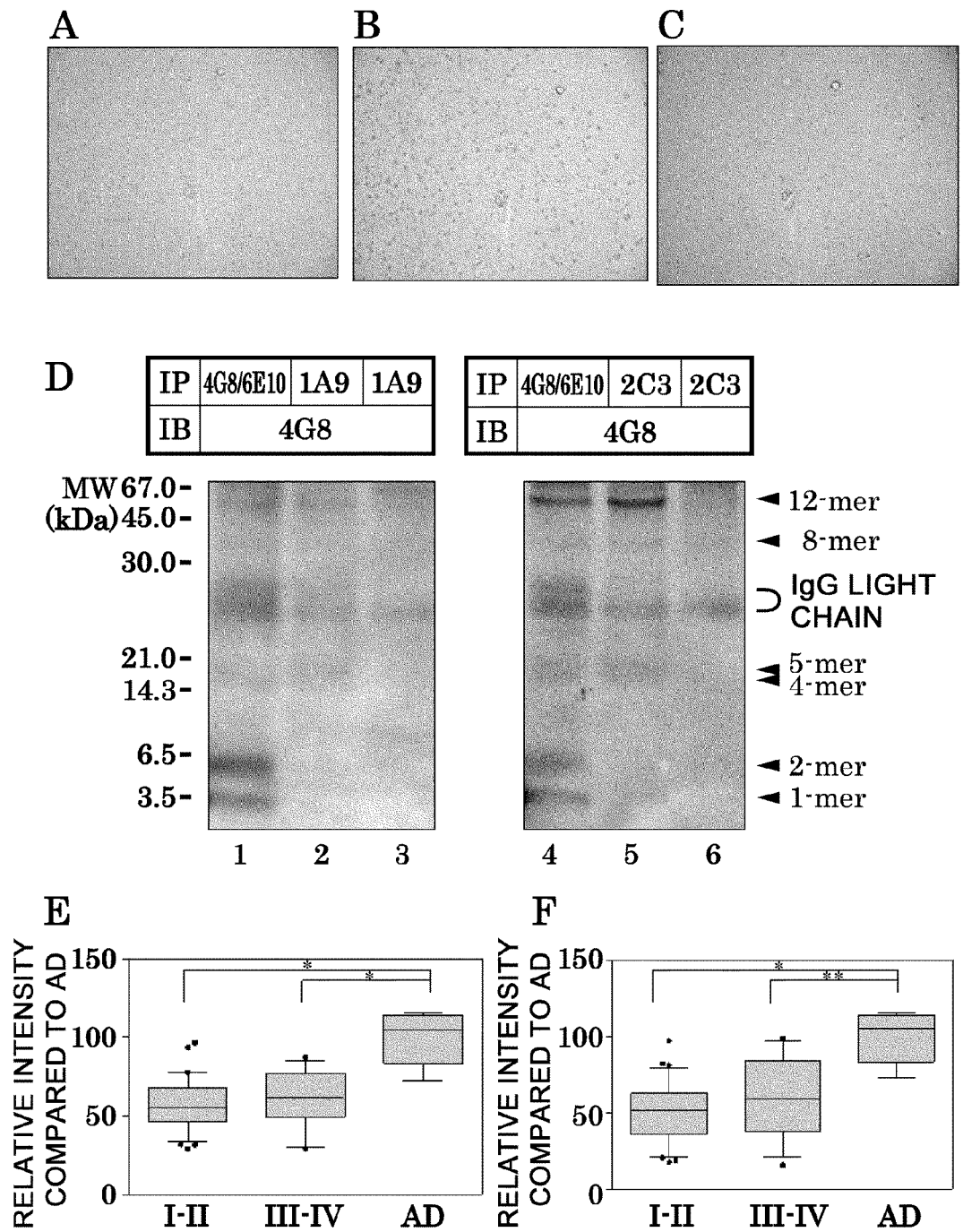
FIG. 6 presents photographs and graphs showing that soluble 1A9- and 2C3-recognized oligomers exist in the human brain. Antibodies against Aβ oligomers can detect senile plaques and vascular amyloids in AD brain only after pretreatment with Protease K. A: 1A9 staining; B: 2C3 staining; and C: A11 staining. D: 4G8 immunoblotting of 1A9- or 2C3-immunoprecipitated Aβ in buffer-soluble AD brain (lanes 1, 2, 4, and 5) and healthy control brain (lanes 3 and 6). Representative results for 1A9 and 2C3 are shown in the left and right half of the panel, respectively. E and F: Semiquantitative analysis (with actin control) of soluble 1A9-immunoreactive 12-mer (Panel E) and soluble 2C3-immunoreactive 12-mer (Panel F) in the human entorhinal cortex obtained from 50 autopsy cases of a healthy elderly population (Braak NFT Stage I or II: n=35; Braak NFT Stage III or IV: n=13; and Braak NFT Stage>IV, AD cases: n=2).

To further assess the existence of "soluble" 1A9- and 2C3-recognized polymers in the brain, the present inventors carried out immunoprecipitation experiments using the two antibodies. Brain homogenates were prepared using Tris-buffered saline (TBS) to avoid chemical modification during the extraction of soluble oligomers. The oligomers having a molecular weight of 4mer, 5mer, 8mer, and 12mer were immunoprecipitated with 1A9 from TBS samples of the cerebral cortex from AD brain (FIG. 6D, lane 2), while the level of the oligomers in the control healthy brain was below the detection limit (lane 3). While the intensity of 4mer, 5mer, and 8mer was comparable between 1A9 (lane 2) and the monoclonal 4G8/6E10 mixture (lane 1), 1A9 appeared to recover a larger amount of 12mer than 4G8/6E10. The immunoprecipitation with 2C3 showed a comparable result (FIG. 6, lanes 4 to 6). Next, the present inventors identified the molecules responsible for the in vivo neurotoxicity in the human entorhinal cortex. It is well known that neurofibrillary tangle (NFT) and nerve cell loss precede the formation of senile plaques in lesions in general elderly populations. The present inventors hypothesized that the lack of functional reservoirs such as senile plaques for 1A9- and 2C3-recognized polymers is harmful for entorhinal cortex neurons, and is a possible cause of memory disturbance. The level of 12mer in the buffer-soluble fractions of previously reported 50 autopsy cases was determined by immunoblotting using monoclonal 1A9 and 2C3. The 50 cases include two AD cases, 35 cases at Braak NFT stages I to II, and 13 cases at NFT stages III to IV (Katsuno et al., Neurology, 64: 687-692, 2005). As shown in FIGS. 6E (1A9) and 6F (2C3), the immunological activity of 1A9- or 2C3-immunoreactive 12mer relative to actin was significantly higher in AD patients as compared to the healthy control group (Braak NFT stages I to II) and mild cognitive impairment group (Braak stages III to IV). Interestingly, the 12mer was accumulated in the entorhinal cortex of the healthy control group (Braak NFT stages I to II) and mild cognitive impairment group (Braak stages III to IV) at a level of about 40% and 60% (the level of AD cases is 100%), respectively (FIGS. 6E and 6F). This result indicates that the accumulation of 12mer precedes the onset of cognitive impairment, and is increased as the Braak NFT stage advances, suggesting that the 1A9- and 2C3-immunoreactive 12mer are polymers responsible for the in vivo neurotoxicity.

Example 7

Monoclonal 1A9 and 2C3 Recognize Aβ Oligomers in the Cerebrospinal Fluid

The Aβ polymers (soluble 1A9- and 2C3-immunoreactive 12mer) responsible for the in vivo neurotoxicity were found in the brain parenchyma. Thus, the present inventors speculated that CSF also contains the polymers. To verify this, the present inventors fractionated pooled CSFs from ten AD patients and ten age-matched healthy individuals as a control by SEC, and assayed the fractions by Aβ oligomer-specific sandwich ELISA using monoclonal BC05 or BA27 in the capturing and detection systems. The BC05/BC05 oligomer ELISA detected soluble Aβ 1-42 in fraction 13, while the BA27/BA27 ELISA detected soluble Aβ 1-40 in fractions 7 to 14 (data not shown). However, in each ELISA, the absorbance (O.D. at 450 nm) was low for sensitive detection of a small amount of Aβ oligomers in CSF. The detection of Aβ monomers in the same fractions by BNT77 ELISA showed that lipoprotein-bound Aβ monomers (fractions 7 to 14) and lipoprotein-free Aβ monomers (fractions 15 to 17) coexist with Aβ oligomers in the fractions (FIGS. 7-1A and 7-1B) (Matsubara E, et al., Neurobiol Aging, 25: 833-841, 2004). The level of lipoprotein-bound Aβ monomer in AD was comparable to that of the healthy control, while the level of lipoprotein-free Aβ40 monomer (FIG. 7-1A) and Aβ42 monomer (FIG. 7-1B) in AD was lower as compared to the age-matched healthy control. The present inventors also found that lipoprotein-bound Aβ monomers, in addition to the oligomers, can be detected when ELISA is designed to use HRP-labeled BC05 or BA27 as a capture antibody. This problem remained unnoticed in the prior art document (Lee E B, et al., J Biol Chem, 281: 4292-4299, 2006), which describes assay methods (for example, 6E10/6E10 ELISA) that are similar to the methods described herein. Since the oligomers and lipoprotein-bound Aβ monomers are eluted at a comparable retention time in SEC, it is impossible to distinguish them by oligomer ELISA using the same antibody in capturing and detection. Thus, it was revealed that CSF containing lipoproteins is unsuitable for a test sample when Aβ oligomers are analyzed using Aβ oligomer-nonselective antibodies.

Figures 1, 7:
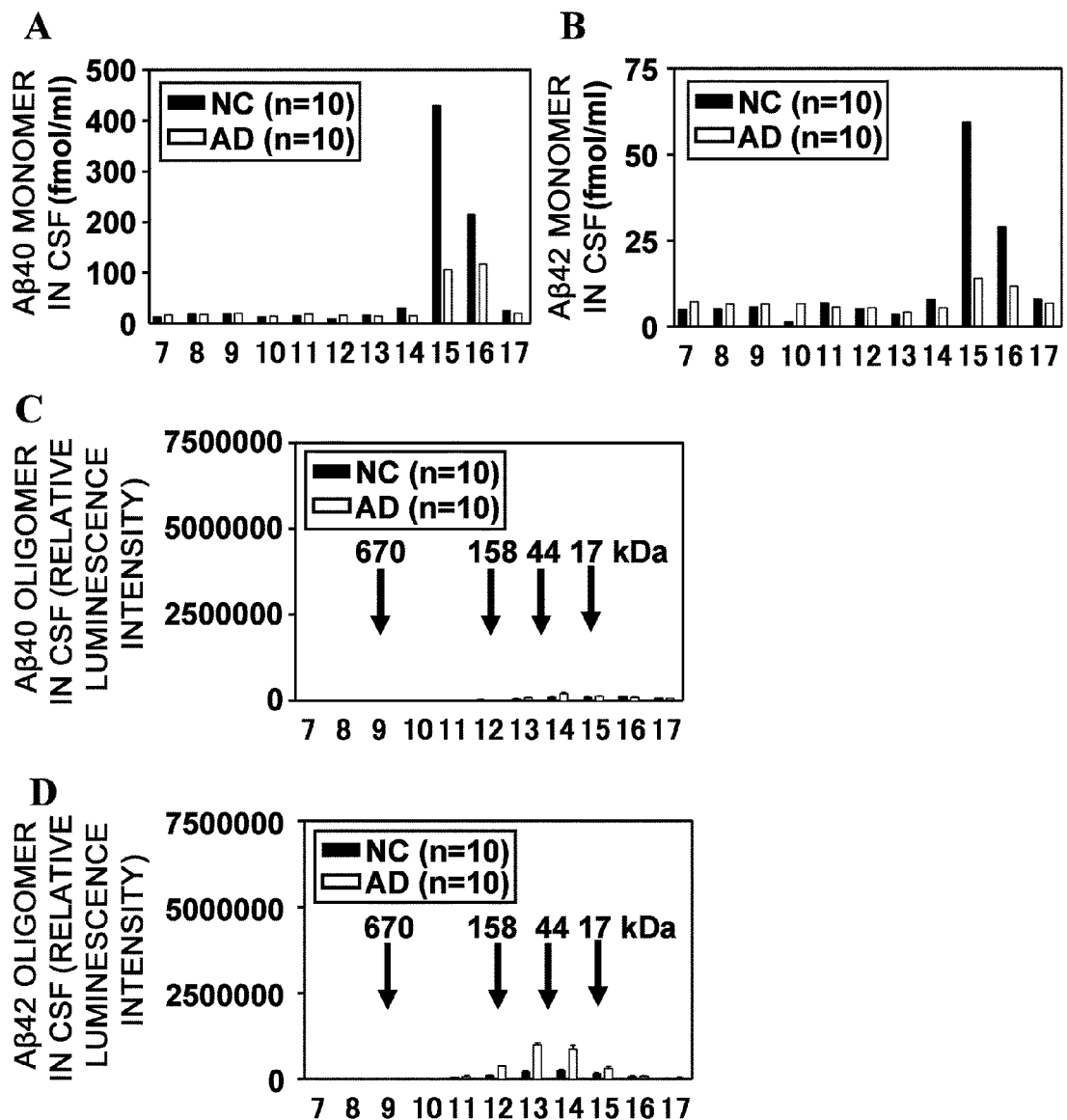
Figures 2, 7:
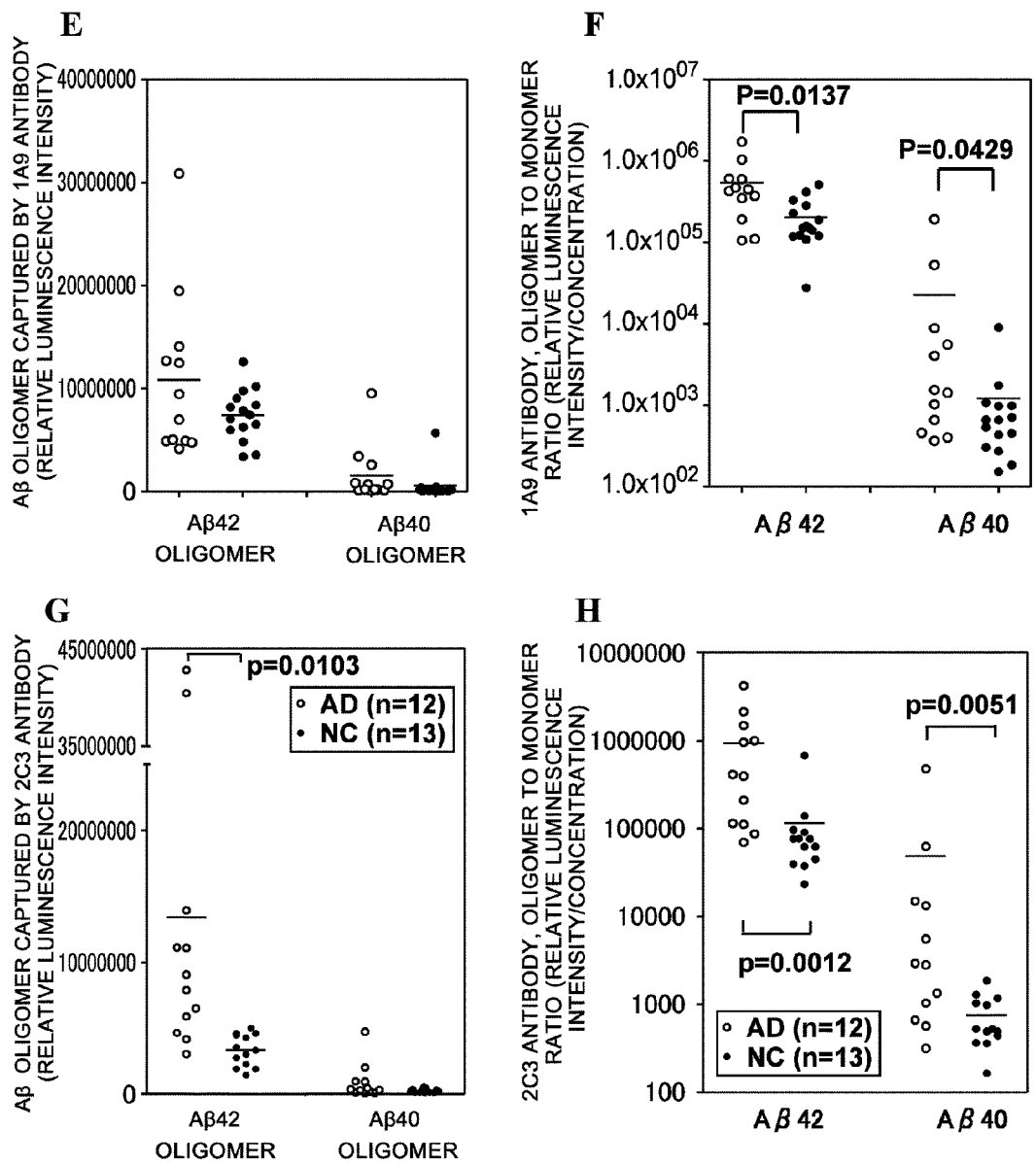

To overcome the weaknesses of the prior art methods, the present inventors improved the detection antibodies and samples used in ELISA. Lipoproteins were pre-depleted from CSF, and the resulting lipoprotein-depleted CSF (LPD-CSF) was used as an assay sample. Aβ oligomer-specific 1A9 and 2C3 were used as detection antibodies for ELISA. Furthermore, chemiluminescence ELISA was developed to enhance the sensitivity. Pooled LPD-CSF (FIGS. 7-1C to D) was fractionated by SEC, and each fraction was analyzed for Aβ oligomer distribution by luminescence ELISA using 1A9 or 2C3 as a detection antibody. As shown in FIGS. 7-1C to D, Aβ oligomers were detected in SEC fractions 12 to 15 (relatively large Aβ with a molecular weight ranging within 18 to 108 kDa, which corresponds to the size of 4mer to 24mer). The level of 1A9- and 2C3-recognized oligomers was elevated in all of the AD patient-derived fractions in which the oligomers were detectable. To assess the usefulness of the Aβ oligomers as therapeutic markers, the level of Aβ oligomers in LPD-CSF from AD patients was compared to that from the age-matched healthy control, although a limited number of cases were analyzed. As shown in FIG. 7-2G, 2C3-recognized oligomers composed of Aβ x-42 were significantly increased in the AD patient group as compared to the normal control group (nonparametric analysis; p=0.0103). By contrast, for 2C3-recognized oligomers composed of Aβ x-42, there was no significant difference between the two groups. Meanwhile, the level of 1A9-recognized oligomers composed of Aβ x-42 was higher in AD than in the control, although the difference was not statistically significant. For 1A9-recognized oligomers composed of Aβ x-40, there was no significant difference between the two groups (FIG. 7-2E). The structural change from Aβ monomer to oligomer occurs in the earliest period of the process of Aβ polymerization. The ratio between Aβ oligomer and monomer (O/M index) can be used as a clinical indicator reflecting the pathological conditions of AD. As shown in FIGS. 7-2F and 7-2H, the O/M indices for Aβ42 and Aβ40 were significantly increased in the AD patient group as compared to the healthy control group (1A9, P=0.0137 for Aβ42 and P=0.0429 for Aβ40; 2C3, P=0.0012 for A42 and P=0.0051 for A40). The results described above show that the 1A9- and 2C3-positive three-dimensional structures are present as Aβ oligomers in LPD-CSF, and increased in AD patients. In addition, the results obtained by the present inventors demonstrated that the structural conversion of lipoprotein-free soluble Aβ to the oligomeric intermediates occurs in CSF of AD patients, and the oligomers can be detected as useful biological markers for diagnosis of sporadic AD.

Example 8

Passive Immunotherapy Using Monoclonal 1A9 and 2C3 Prevents the Onset of Memory Disturbance in T22576

Figure 8:
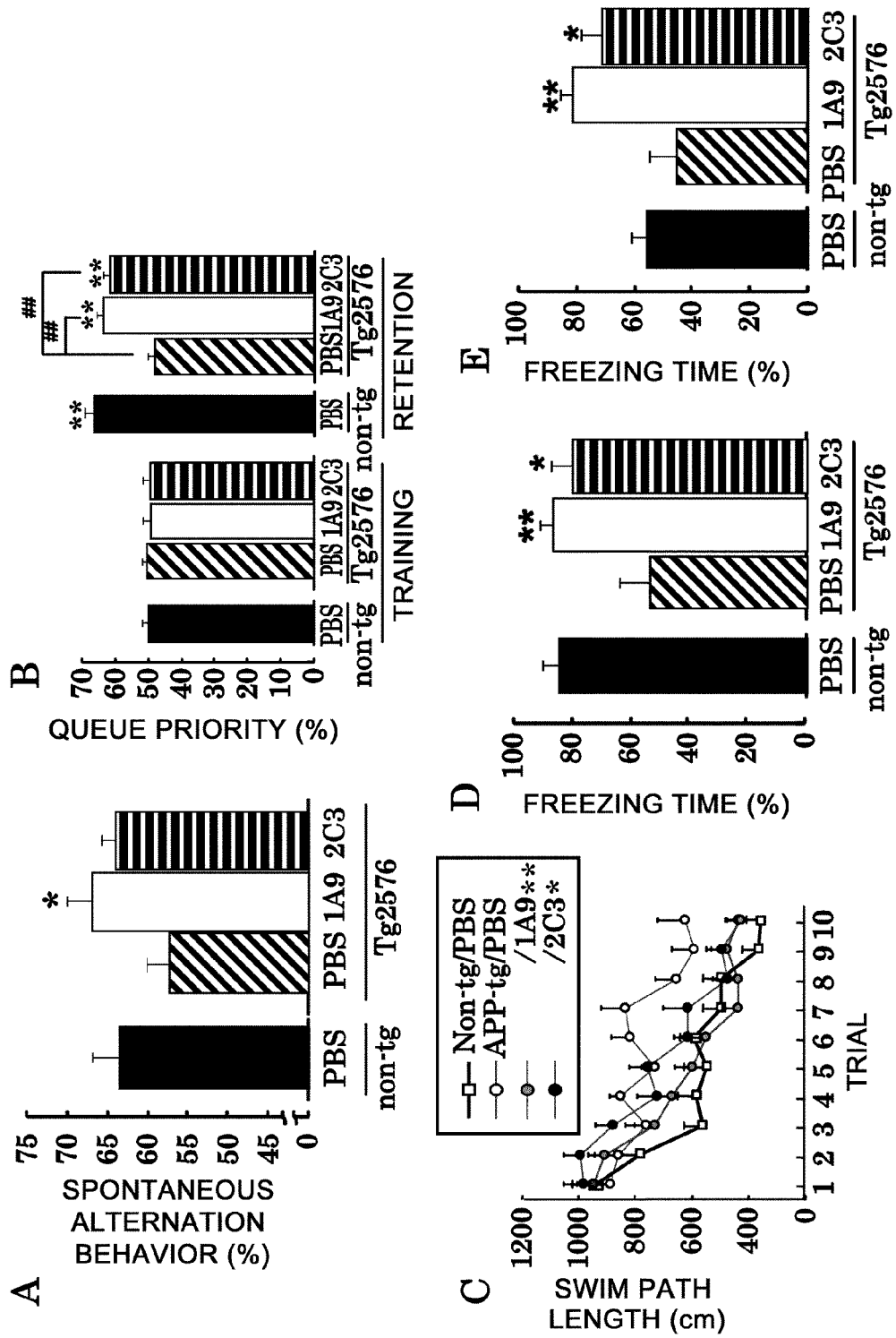
FIG. 8 presents graphs showing that the onset of memory impairment in Tg2576 mice can be prevented by passive immunization treatment. 13-month-old Tg2576 mice were divided into the following three groups to perform learning/behavior tests: PBS-administered group: n=10; 1A9-administered group: n=13; and 2C3-administered group: n=11. All of the measured values were indicated as mean±SE. (A) Y-maze test. Spontaneous alteration behavior was monitored in each group during an eight-minute session of the Y-maze task. The results of one-way ANOVA were as follows: $F(1, 52)=3.09$, $p<0.05$; $*p<0.05$ in the comparison with PBS-administered Tg2576 mice. (B) Novel object recognition test. The retention session was performed 24 hours after training. The exploratory preference in a ten-minute session in the novel object recognition test was determined in each group. The results of two-way ANOVA were as follows: training/retention, $F(1, 64)=31.53$, $p<0.01$; animal group, $F(2, 64)=7.49$, $p<0.01$; repeated training/retention by the animal group, $F(2, 64)=10.12$, $p<0.01$; $p<0.01$ in the comparison with the corresponding untrained mice, $\#\#p<0.01$ in the comparison with PBS-administered Tg2576 mice. (C) The swimming path length during a 60-second session of water maze test was measured for each group. The results of two-way ANOVA were as follows: trial, $F(9, 320)=20.46$, $p<0.01$; animal group, $F(2, 320)=12.59$, $p<0.01$; repeated trial by the animal group, $F(18, 320)=1.78$, $p<0.05$; $p<0.05$, $p<0.01$ in the comparison with PBS-administered Tg2576 mice. Fear-conditioned learning test: Context-dependent (D) and clue-dependent freezing times (E) were determined. The results of two-way ANOVA were as follows: context-dependent test, $F(2, 32)=5.94$, $p<0.01$; clue-dependent test, $F(2, 32)=7.33$, $p<0.01$; $*p<0.05$ and $**p<0.01$ in the comparison with PBS-administered Tg2576 mice.

To assess the in vivo preventive/therapeutic effect of passive immunotherapy based on the administration of 1A9 (n=13) or 2C3 (n=11), the present inventors administered 1A9 or 2C3 (0.4 mg/kg/week), or PBS to Tg2576 mice via the caudal vein during the 4 to 13 month period. The memory function was assessed at 13 months old in terms of the following four types of learning/behavioral paradigms:
(1) short-term memory in Y-maze test (FIG. 8A);
(2) object recognition memory in novel object recognition test (FIG. 8B);
(3) spacial memory in water maze test (FIG. 8C); and
(4) associative emotional memory in contextual fear conditioning test (FIG. 8D).

As compared to 1A9- and 2C3-administered Tg2576 mice, PBS-administered Tg2576 mice showed significant learning and behavioral impairments (FIG. 8A to 8D). Unlike the memory function of PBS-administered Tg2576 mice (n=10), the memory function of 1A9 and 2C3-administered Tg2576 mice was indistinguishable from that of age-matched non-administered wild type cohort mice, which was previously determined. Therefore, 1A9 and 2C3-administered Tg2576 mice were shown to retain both short- and long-term memory, which were impaired in the PBS administration group. That is, the present inventors obtained evidence supporting the view that the onset of memory disturbance, in particular AD, can be prevented by conducting passive immunotherapy targeting Aβ oligomers before the onset. Furthermore, the result described above presents the first in vivo evidence that directly indicates that Aβ oligomers are responsible for the onset of memory disturbance.

Example 9

Monoclonal 1A9 Prevents Aβ Accumulation in the Brain of Tg2576

Figure 9:
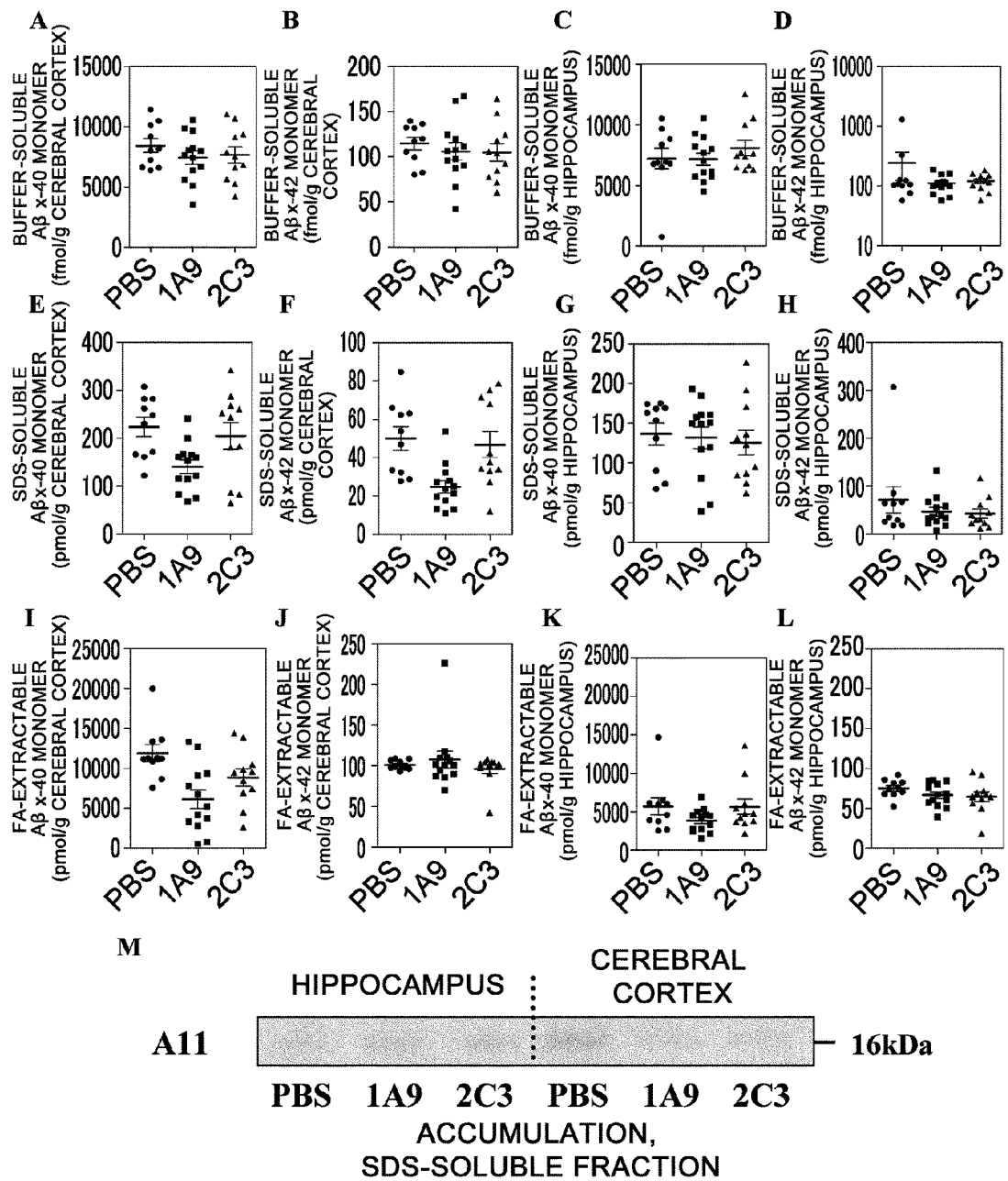
FIG. 9 presents graphs and a photograph showing that the brain Aβ accumulation in Tg2576 can be prevented by passive immunotherapy. The hippocampus and cerebral cortex of three groups of 13-month-old Tg2576 mice (PBS-administered group, n=10; 1A9-administered group, n=13; and 2C3-administered group, n=11) were extracted in three continuous steps to prepare the buffer-soluble, SDS-soluble, and formic acid (FA)-extractable fractions. Each of the fractions was subjected to Aβ-specific ELISAs (WAKO kit: BNT77-BA27 for Aβ x-40; BNT77-BC05 for Aβ x-42). The accumulation of Aβ 40 (SDS and FA) and Aβ 42 (SDS) was found to be significantly suppressed only in the 1A9-treated group. The accumulation-suppressing effect for the A11-positive oligomer (4-mer) was confirmed in the SDS-soluble cerebral cortex fractions from the two antibody-treated groups.

Tg2576 mice administered with PBS (n=10) and Tg2576 mice treated with passive immunotherapy during the 4 to 13 month period (1A9 administration group, n=13; 2C3 administration group, n=11) were dissected after the learning/behavioral experiments. The amount of Aβ accumulated in the brain (cerebral cortex vs. hippocampus) was determined in the following three fractions (150 mg/extract) prepared by serial extraction: soluble fraction in Tris buffer containing protease inhibitors; 2% SDS-soluble amyloid fraction; and 2% SDS-insoluble and 70% formic acid-soluble amyloid fraction. It is considered that non-accumulative, physiological Aβ molecules are contained in the Tris buffer fraction, while 2% SDS-soluble Aβ includes Aβ in diffuse senile plaques before amyloid fibril formation, immunocytochemically undetectable Aβ, and conformationally altered, accumulative soluble oligomeric Aβ. Aβ was selectively quantified by Aβ40 and Aβ42 end-specific ELISA (BNT77/BA27 specific for Aβ40, BNT77/BC05 specific for Aβ42, WAKO kit). There was no marked difference among the three groups in the Aβ concentration in the Tris buffer fraction where the major components were non-accumulative, physiological Aβ molecules (FIGS. 9A and 9C, Aβ x-40; FIGS. 9B and 9D, Aβ x-42). Regarding soluble Aβ accumulated in the brain (SDS fraction), a significant suppressive effect on the accumulation of Aβ x-40 and Aβ x-42 in the cerebral cortex was observed only in the 1A9 administration group (FIG. 9E, Aβ x-40; FIG. 9F, Aβ x-42). No accumulation-suppressive effect was observed in the hippocampus (FIG. 9G, Aβ x-40; FIG. 9H, Aβ x-42). Meanwhile, regarding insoluble Aβ accumulated in the brain (FA fraction), a significant suppressive effect on the accumulation of Aβ x-40 in the cerebral cortex was observed only in the 1A9 administration group (FIG. 9I, Aβ x-40; FIG. 9J, Aβ x-42). No accumulation-suppressive effect was observed in the hippocampus (FIG. 9K, Aβ x-40; FIG. 9L, Aβ x-42). The A11 immunoblot analysis of the SDS-soluble fractions showed a suppressive effect on the accumulation of A11-positive oligomer (4mer) in the cerebral cortex in the two antibody treatment groups (FIG. 9M).

Example 10

Plasma Aβ Oligomers are Increased by Passive Immunotherapy with 1A9 and 2C3

Figure 10:
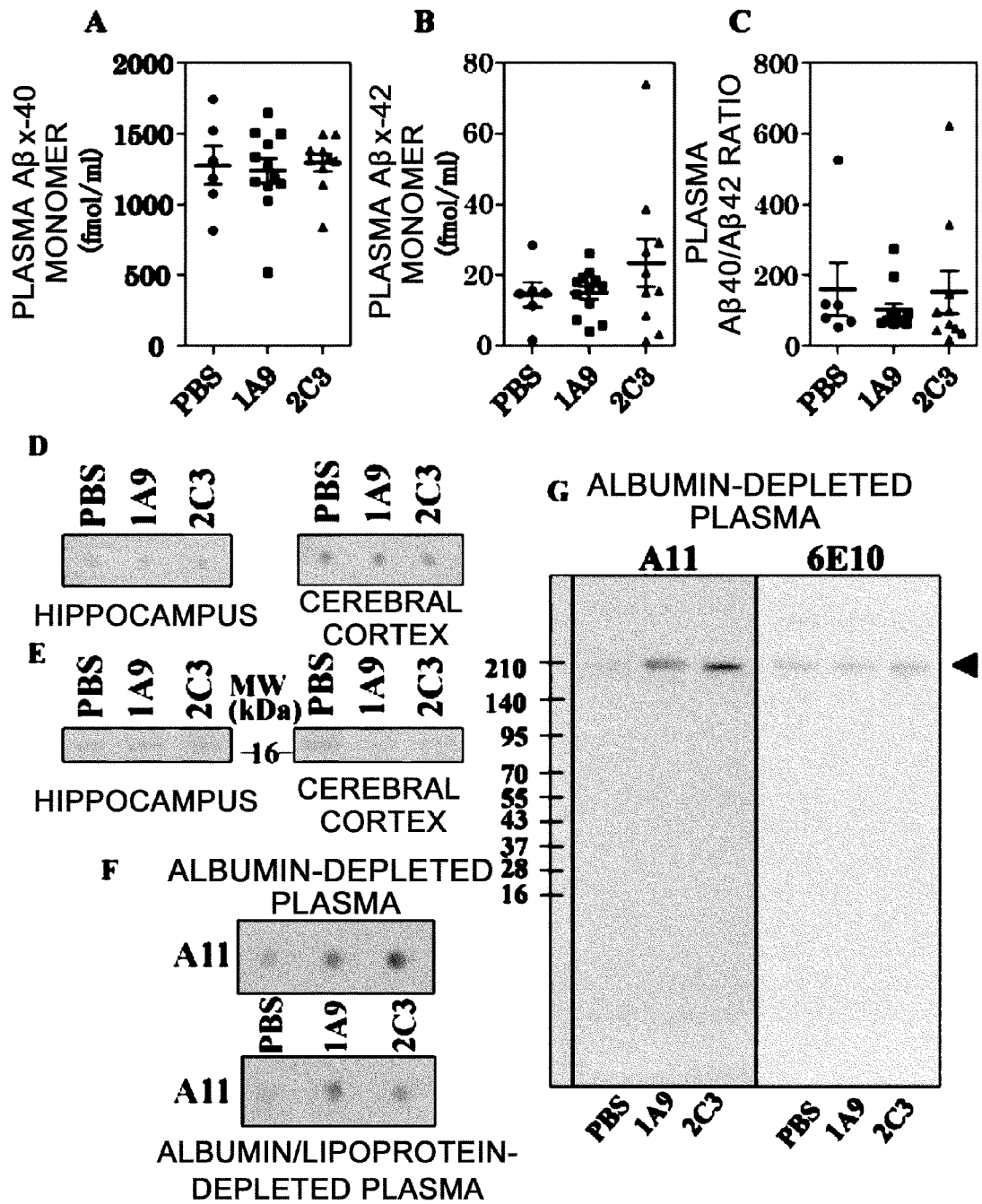
FIG. 10 presents photographs and graphs on Aβ oligomers in the plasma and brain of Tg2576. A and B: As a result of ELISA analysis, no significant difference in the amount of Aβ x-40 and Aβ x-42 in the plasma was observed between the PBS-administered group and the immunotherapy group. C: Similarly, no difference in the Aβ 40/Aβ 42 ratio was observed among the three groups tested. D: As a result of dot blot analysis using pooled brain homogenates, no difference in the amount of physiological saline-soluble A11-positive oligomer was observed among the three groups tested. Hippocampus (left panel) and cerebral cortex (right panel). PBS-administered group, n=10; 1A9-administered group, n=13; and 2C3-administered group, n=11 E: According to immunoblot analysis using the anti-oligomer A11 antibody, the immunoreactivity of the Aβ tetramer in the SDS-extracted cerebral cortex fraction (right panel) was decreased in the 1A9- and 2C3-administered groups compared to the PBS-administered group. On the other hand, this was not observed in the hippocampus (left panel). F: Blood (albumin-depleted plasma, upper part of Panel F; albumin/lipoprotein-depleted plasma, lower part of Panel F) was pooled from each of the groups, and subjected to A11 dot blot analysis. As a result, the A11 immunoreactivity was found to be increased in the 1A9- and 2C3-administered groups compared to the PBS-administered group (Panel F). The proportion of the lipoprotein-bound form of 2C3-recognized oligomers was higher than that of 1A9-recognized oligomers (lower part of Panel F). Furthermore, the A11 immunoblotting also showed positive signals at approximately 200 kDa, and the immunoreactivity was clearly increased in the 1A9- and 2C3-administered groups compared to the PBS-administered group (Panel G). From these results, it is conceivable that the therapeutic effect selective only to target Aβ oligomer molecules was obtained in the antibody-administered groups without affecting physiological molecules.

There was no significant difference in the plasma Aβ concentration among the following three groups: Tg2576 mice administered with PBS (n=10), and Tg2576 mice treated with passive immunotherapy during the 4 to 13 month period (1A9 administration group, n=13; 2C3 administration group, n=11) (FIG. 10A, Aβ x-40; FIG. 10B, Aβ x-42). There was also no significant difference in the Aβ40/42 ratio (FIG. 10C).

In order to elucidate the mechanism underlying the preventive effect of passive immunotherapy with 1A9 and 2C3 (IVIg) against the AD-like phenotype in Tg2576 mice, the present inventors assessed the level of physiological saline-soluble and -insoluble Aβ oligomers in pooled brain homogenates, and the level of Aβ oligomers in the peripheral blood and plasma. There was no difference in the amount of physiological saline-soluble Aβ oligomers in the pooled brain homogenates among the treatment groups (FIG. 10D). Meanwhile, the amount of insoluble Aβ oligomers was shown to be reduced in the 1A9 and 2C3 treatment groups (FIG. 10E). Furthermore, pooled plasma from each group (albumin-depleted plasma, upper part of Panel F; albumin/lipoprotein-depleted plasma, lower part of Panel F) was assayed for Aβ oligomers by A11 dot blotting. The result shows that the oligomers were present in the plasma from PBS-administered Tg2576 mice (FIG. 10F). A11-positive oligomers in plasma were clearly increased in the passive immunotherapy groups as compared to the PBS administration group (FIG. 10F). The proportion of 2C3-recognized oligomers in a lipoprotein-bound form was greater than that of 1A9-recognized oligomers (lower part of Panel F). Furthermore, plasma Aβ oligomers were detected by A11 immunoprecipitation. The result shows that the oligomers of about 200 kDa were increased in Tg2576 mice treated with passive immunotherapy as compared to the PBS administration group (FIG. 10G). The increase in plasma Aβ oligomers in the passive immunotherapy groups can be considered to directly reflect enhanced cerebral clearance. Thus, the present inventors obtained evidence that direct target molecules for intravenous passive immunotherapy are also present in blood in addition to brain, and that oligomer-selective cerebral clearance can be enhanced through peripheral sites of action. That is, the present inventors showed the clinical usefulness of the intravenous passive immunotherapy.

Example 11

Formation of Senile Amyloid Plaques and Swollen Dystrophic Neurites can be Suppressed by Passive Immunotherapy Using 1A9 and 2C3

Figure 11:
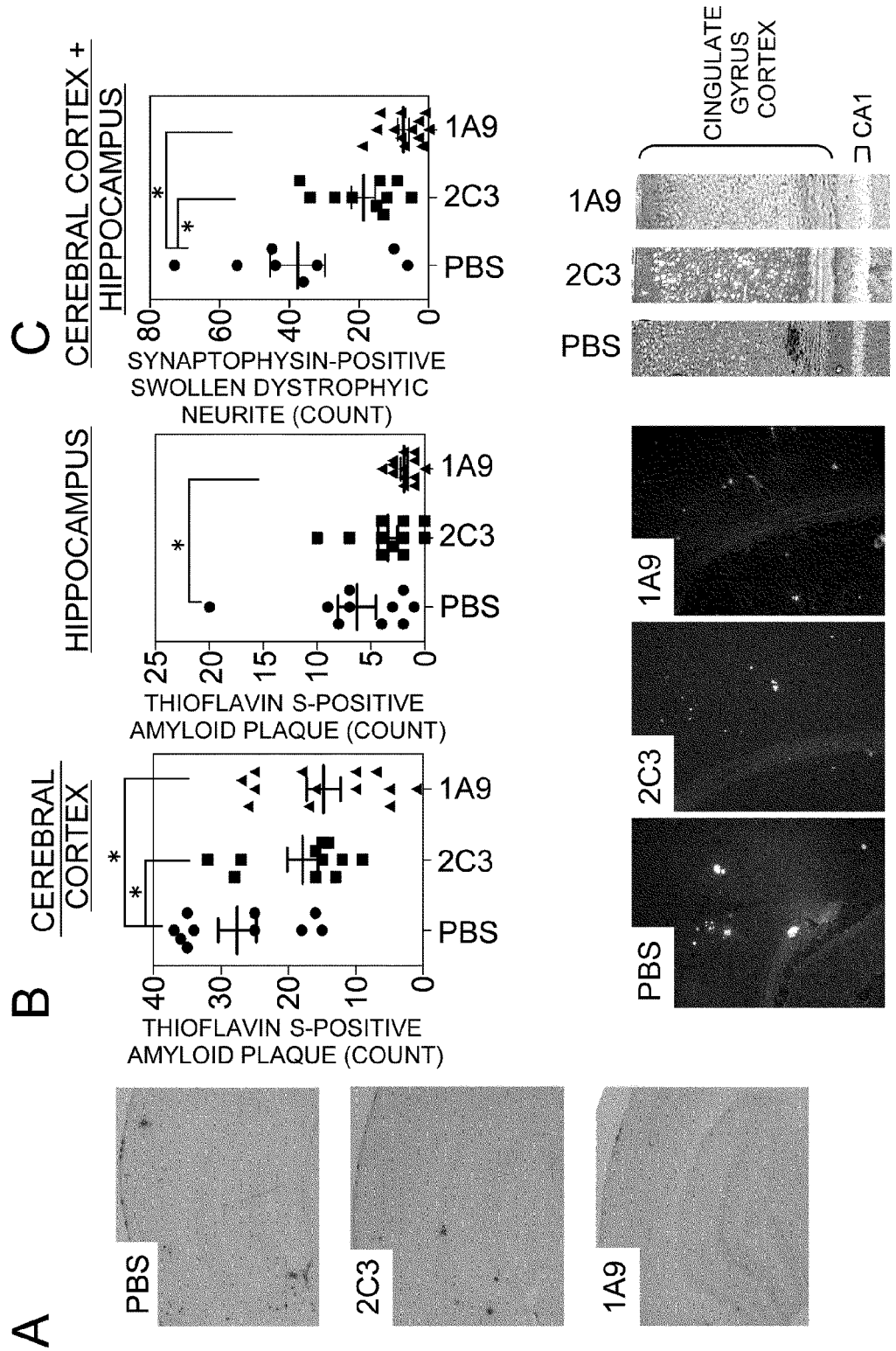
FIG. 11 presents photographs and graphs showing that senile plaque amyloid formation (A: Aβ-specific antibody staining; and B: thioflavin-5-positive analysis) and swollen dystrophic neurite formation (C: synaptophysin-positive analysis) were suppressed in the Tg2576 mouse brain by passive immunization treatment.

Immunohistochemical Aβ deposition was suppressed in the passive immunotherapy groups (FIG. 11A). The formation of thioflavin S-positive senile amyloid plaques was significantly suppressed in both the cerebral cortex and hippocampus (FIG. 11B, upper part), and the reduction was also clearly demonstrated by histochemistry (FIG. 11B, lower part). The formation of synaptophysin-positive swollen dystrophic neurites was also significantly suppressed in the passive immunotherapy groups (FIG. 11C).

Example 12

Immunostaining Analysis Using Anti-Synaptophysin and Anti-Drebrin Antibodies

Figure 12:
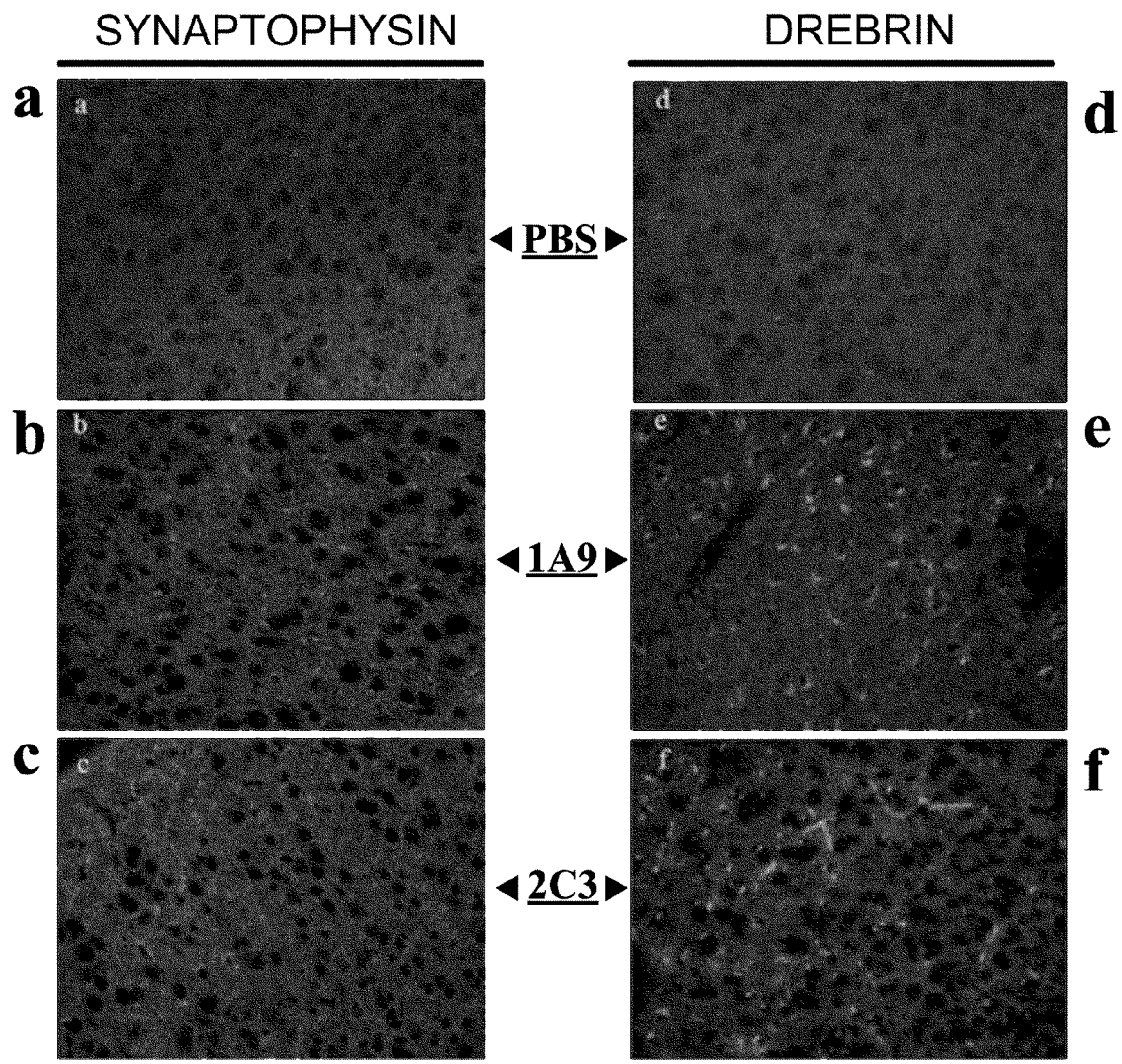
FIG. 12 presents photographs showing the suppression of synaptic degeneration by passive immunization treatment with 1A9 and 2CJ. Immunostaining of synaptophysin (left panels) and drebrin (right panels) in presynaptic and postsynaptic dot-like peripheral cells. Top: PBS administration; middle: 1A9 administration; and bottom: 2C3 administration.

1A9 and 2C3 suppressed the presynaptic and postsynaptic degeneration in the cerebral neocortex (FIG. 12).

Example 13

The Antibodies Translocate to the Brain

Figure 13:
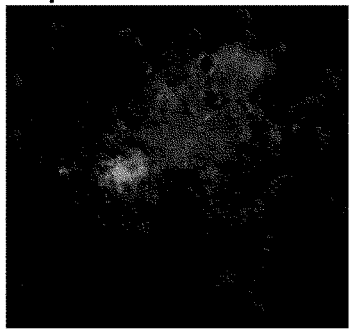
FIG. 13 presents photographs showing the brain transfer of the antibodies by passive immunization treatment. The distribution of administered antibodies in the Tg2576 mouse brain is shown. Staining with anti-Aβ antibodies (left panels) and IgG (center panels). 1A9 administration (A), 2C3 administration (B), and PBS administration (C).
Figure 13:
Figure 13:
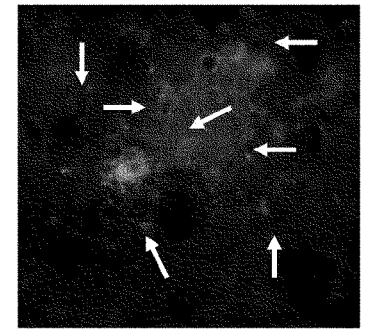
Figure 13:
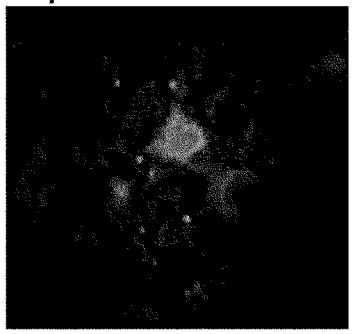
Figure 13:
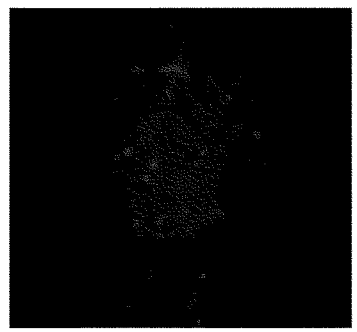
Figure 13:
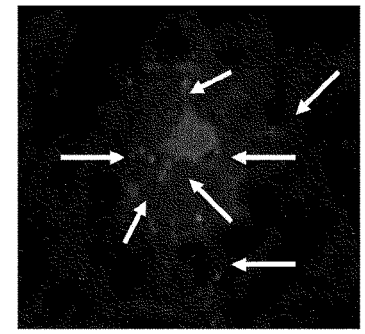
Figure 13:
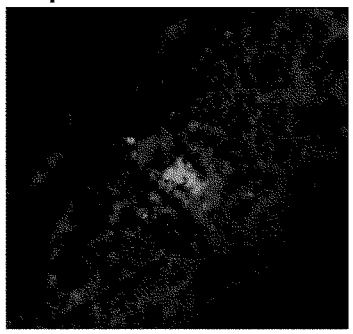
Figure 13:
Figure 13:
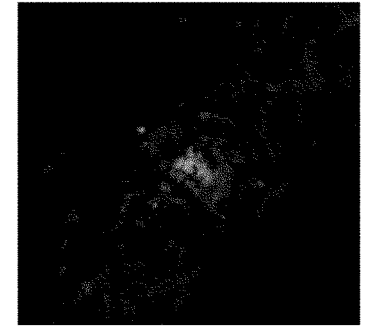

The existence/localization of deposited Aβ and cerebral mouse IgG was assessed using a confocal laser microscope. The result shows that mouse IgG is localized almost independently of deposited Aβ within the areas containing diffuse senile plaques. Mouse IgG was observed only in the passive immunotherapy groups (1A9, FIG. 13A; 2C3, FIG. 13B), but not in the PBS administration group (FIG. 13C). Thus, a fraction of the antibodies administered into the blood was considered to translocate to the brain. This result shows that the preventive effect on memory disturbance was produced not only through the direct neutralization of the toxicity of soluble Aβ polymers by the antibodies translocated to the brain, but also through the clearance of soluble Aβ polymers in the form of a complex with the antibodies into the blood. Thus, the therapeutic effect was considered to be based on multiple action mechanisms.

Example 14

Figure 14:
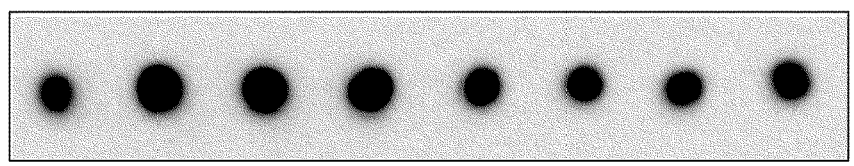
FIG. 14 presents photographs showing, by dot blot analysis, that the monoclonal antibodies 5A5, 5A9, 4F7, 4H5, 6E4, and 6H4 are specific to Aβ oligomers (3 to 96 hours), but do not recognize Aβ monomers (0 hour).
Figure 14:
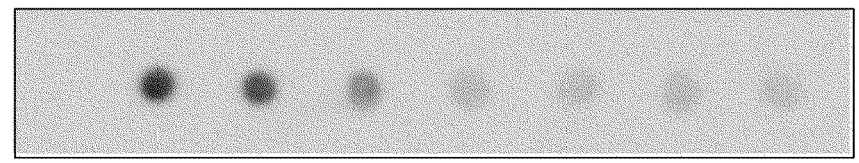
Figure 14:
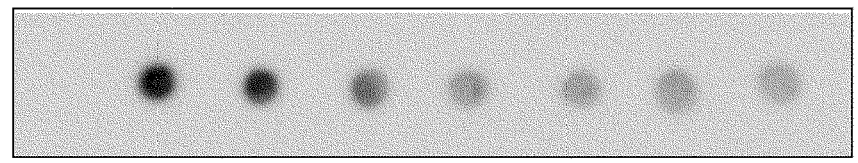
Figure 14:
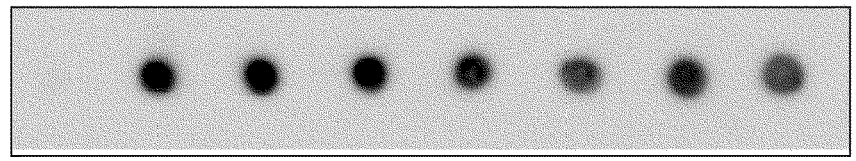
Figure 14:
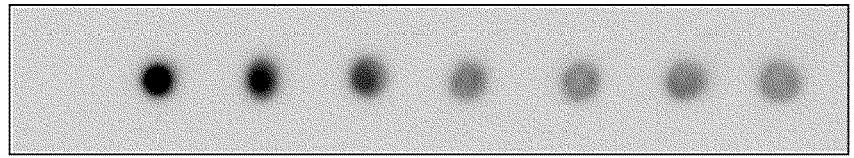
Figure 14:
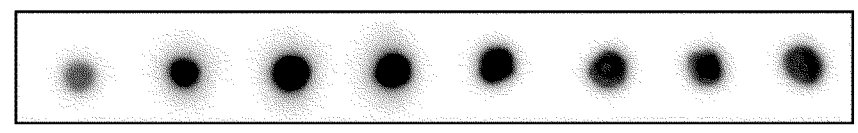
Figure 14:
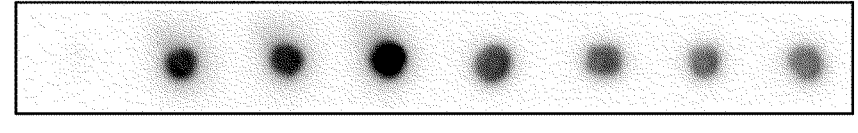
Figure 14:
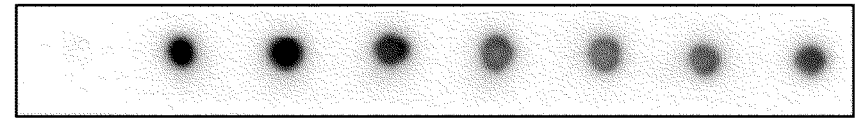

Preparation of Aβ Oligomer-Specific Monoclonal Antibodies (5A5, 5A9, 4F7, 4H5, 6E4, and 6H4) and Dot Blot Analysis 33 clones prepared by the above-described method that uses the Aβ 1-40 oligomer as an antigen were assessed by dot blot analysis. The result showed that the six types of monoclonal antibodies specifically recognize Aβ oligomers. As shown below, the isotype of the six types of antibodies (4F7, 4H5, 5A5, 5A9, 6E4, and 6H4) was determined:
4F7: κ for the L chain, and IgG2a for the H chain;
4H5: κ for the L chain, and IgG2a for the H chain;

5A5: κ for the L chain, and IgG2b for the H chain;
5A9: κ for the L chain, and IgG2b for the H chain;
6E4: κ for the L chain, and IgG1 for the H chain; and
6H4: κ for the L chain, and IgG2b for the H chain.
Furthermore, the immuno-dot blot analysis showed that, as with 2C3 described above, the 4F7, 4H5, 5A5, 5A9, 6E4, and 6H4 antibodies specifically bind to Aβ oligomers but do not recognize Aβ monomers (see FIG. 14).

Example 15

Inhibition ELISA

Figure 15:
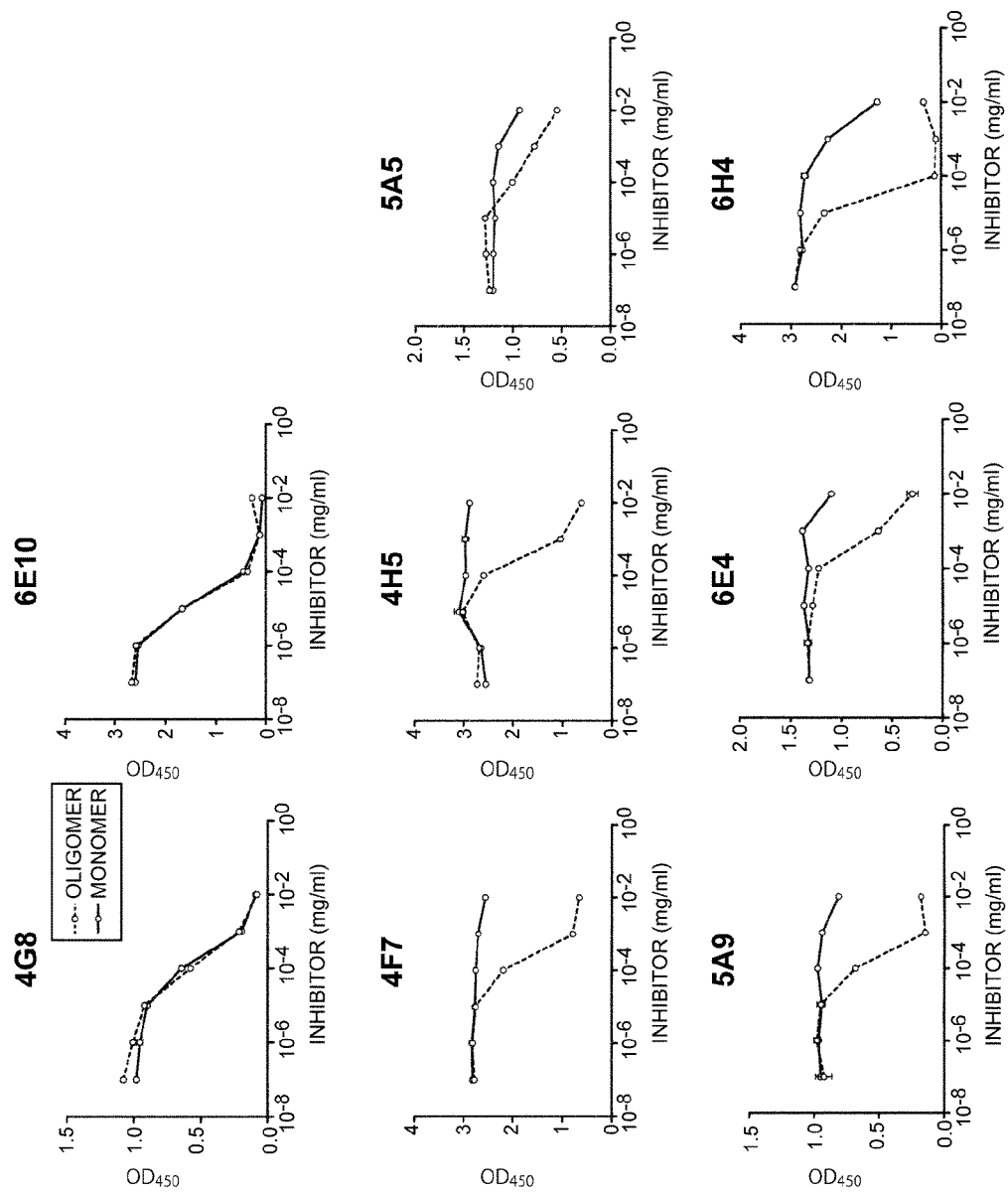
FIG. 15 presents graphs showing the Aβ oligomer-selective binding ability of the six types of antibodies (4F7, 4H5, 5A5, 5A9, 6E4, and 6H4). The vertical axis indicates the absorbance at a wavelength of 450 nm, and the horizontal axis indicates the concentration of Aβ oligomer or Aβ monomer used as an inhibitor. In each graph, the dashed line indicates the antibody-binding activity when the Aβ oligomer was used as the inhibitor, and the solid line indicates the antibody-binding activity when the Aβ monomer was used as the inhibitor.

To assess the Aβ oligomer-selective binding activity of the six types of antibodies (4F7, 4H5, 5A5, 5A9, 6E4, and 6H4), each antibody was mixed with stepwise-diluted Aβ oligomers or monomers ("inhibitors"), and the pre-mixed solutions were added to Aβ oligomer-immobilized 96-well immunoplates, and then incubated (see the "Methods" section). The commercially available 4G8 and 6E10 antibodies were used as control antibodies that nonselectively bind to Aβ oligomers and monomers. When an antibody selectively binds to Aβ oligomers, the antibody pre-mixed with Aβ monomers does not bind to the Aβ monomers in the solution, and therefore can bind to immobilized Aβ oligomers. On the other hand, the antibody pre-mixed with Aβ oligomers binds to the Aβ oligomers in the solution, and therefore the amount of antibody bound to immobilized Aβ oligomers is reduced with the increase in inhibitor concentration. The results for the six types of antibodies (4F7, 4H5, 5A5, 5A9, 6E4, and 6H4) showed concentration-dependent reduction in the amount of bound antibody when Aβ oligomers were used. In contrast, no such strong reduction in binding was detected when Aβ monomers were used (see FIG. 15). Meanwhile, for 4G8 and 6E10, the concentration-dependent reduction in the amount of bound antibody was observed when Aβ monomers and oligomers were used (see FIG. 15). These results suggest that the six types of antibodies (4F7, 4H5, 5A5, 5A9, 6E4, and 6H4) selectively bind to Aβ oligomers.

Example 16

Figure 16:
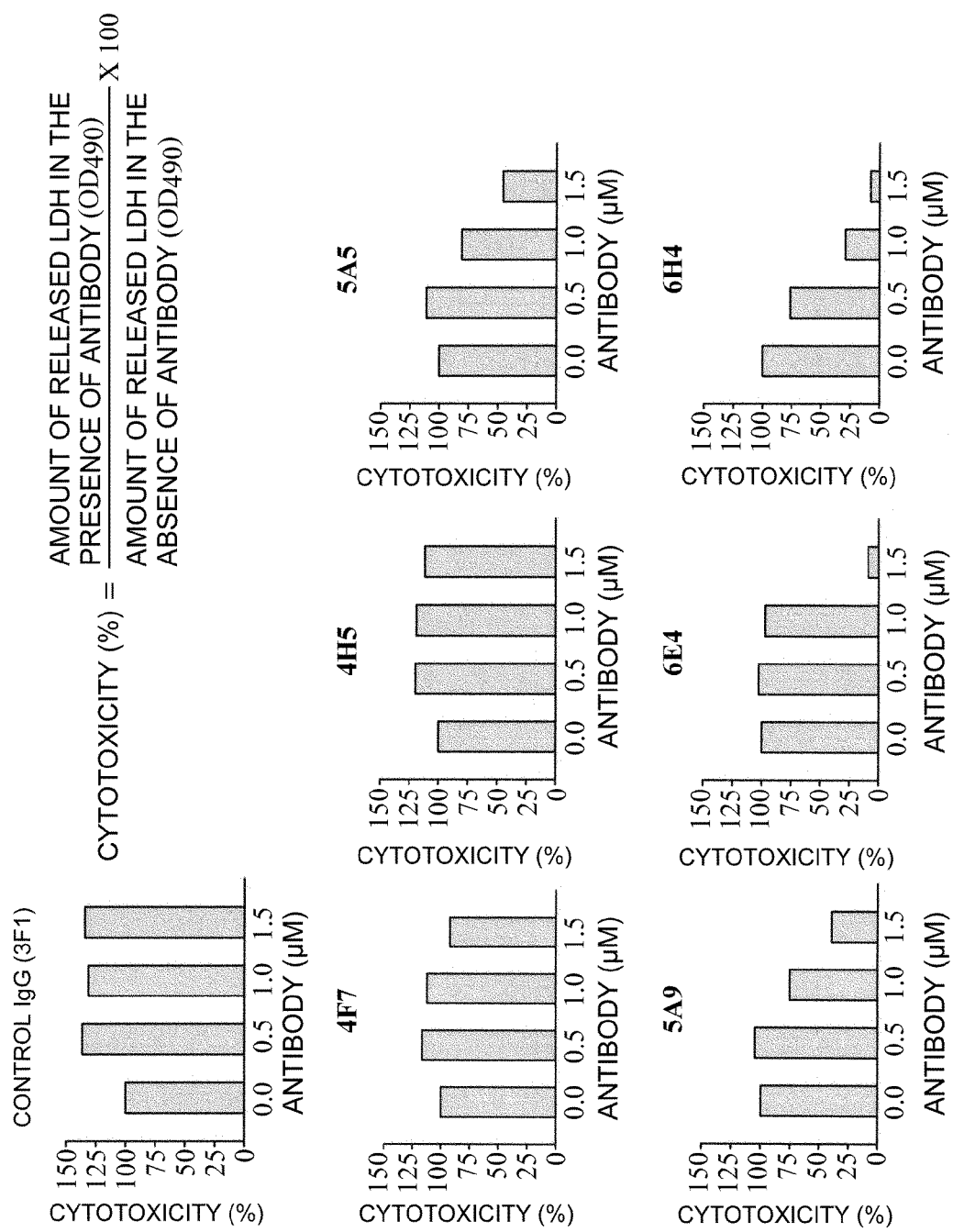
FIG. 16 presents graphs showing the neutralizing activity of the six types of antibodies (4F7, 4H5, 5A5, 5A9, 6E4, and 6H4) against Aβ-induced neurotoxicity. The horizontal axis indicates the amount of antibody added, and the vertical axis shows the cytotoxicity relative to that under the antibody-free condition as the standard (see the equation in the figure).

The Activity of the Six Types of Antibodies (4F7, 4H5, 5A5, 5A9, 6E4 and 6H4) to Neutralize Aβ-Induced Neurotoxicity To assess whether the six types of antibodies (4F7, 4H5, 5A5, 5A9, 6E4, and 6H4) have an activity of neutralizing Aβ-induced neurotoxicity, human neuroblastoma cells (SH-SY5Y) were cultured in a medium containing Aβ 1-42 (12.5 μM) in the presence or absence of the antibodies for 24 hours, and the change in Aβ 1-42-induced cytotoxicity was monitored. As a result, the cytotoxicity was enhanced by addition of control IgG (3F1). Although the cytotoxicity was also increased by addition of the 4F7 and 4H5 antibodies, the increase was smaller than that observed for 3F1 (see FIG. 16). The remaining four types of antibodies (5A5, 5A9, 6E4, and 6H4) were found to markedly reduce the cytotoxicity (see FIG. 16). The results described above demonstrate that the four types of antibodies (5A5, 5A9, 6E4, and 6H4) have a strong activity of neutralizing Aβ-induced neurotoxicity. Since 4F7 and 4H5 lowered the cytotoxicity as compared to control IgG, these antibodies are also inferred to have an activity of neutralizing Aβ-induced neurotoxicity.

Example 17

The Activity of the Six Types of Antibodies (4F7, 4H5, 5A5, 5A9, 6E4 and 6H4) to Suppress Aβ Amyloid Fibril Formation To assess whether the six types of antibodies (4F7, 4H5, 5A5, 5A9, 6E4, and 6H4) have an activity of suppressing Aβ amyloid fibril formation, the formation of Aβ amyloid fibrils was detected by the ThT fluorescence intensity assay method in a solution (medium) whose composition was the same as that used in the experiment for Aβ-induced neurotoxicity (see the "Methods" section). 6E4 and 6H4 were found to suppress the fibril formation in an antibody concentration-dependent manner (see FIG. 17). The other four antibodies (4F7, 4H5, 5A5, and 5A9) were also inferred to have an activity of suppressing the fibril formation, since the antibodies exhibited the tendency of suppressing the fibril formation as compared to control IgG Discussion The data obtained by the present inventors show that monoclonal 1A9 and 2C3 specifically recognize the "neurotoxic epitope" and "polymerization epitope" of soluble Aβ polymers that are responsible for the toxic activity and neurofibril formation activity. Since monoclonal 1A9 and 2C3 do not react with soluble Aβ monomers, which are physiological molecules, it can be concluded that a three-dimensional structure having the epitope that is recognized by 1A9 or 2C3 is specific to soluble oligomeric polymers. The experiments using ultrafiltration and molecular sieve revealed that the size of 1A9- and 2C3-immunoreactive oligomers is greater than 100 kDa (>20mer). The result of morphological observation by AFM demonstrated that the toxic polymers are morphologically heterogeneous (granular, bead-shaped, and ring-shaped).

To demonstrate that the toxic polymers are actually bioactive molecules that exhibit in vivo synaptic toxicity, the present inventors commenced treatment of young Tg2576 mice before the onset of memory disturbance with anti-Aβ oligomer passive immunotherapy targeting 1A9- and 2C3-recognized toxic polymers. For the first time, the present inventors presented evidence supporting that age-dependent memory deterioration that naturally develops in Tg2576 mice can be prevented by passive immunotherapy using anti-Aβ oligomer-specific antibodies (1A9 and 2C3). Herein, short-term memory disturbance assessed by the Y-maze test is similar to the Aβ accumulation-associated memory disturbance observed in mild cognitive impairment (MCI) and early AD. The Y-maze test showed excellent and almost normal results in Tg2576 mice administered with 1A9 and 2C3, respectively. When assessed by the novel object recognition task, Morris water maze, and contextual fear conditioning task, the long-term memory was maintained nearly normal by the anti-Aβ oligomer antibodies.

A selective increase in A11-positive oligomers in blood was observed in the antibody-treated mouse groups as compared to the PBS treatment group, which is consistent with the ability of the antibodies to prevent the onset of memory disturbance (the memory maintenance ability). The 1A9 antibody treatment also exhibited the effect of suppressing cerebral Aβ accumulation. The 2C3 antibody treatment demonstrated a higher blood level of A11-positive oligomers as compared to the 1A9 antibody treatment. However, the cerebral Aβ accumulation-suppressing effect of the 2C3 antibody treatment was unclear. Accordingly, 1A9-recognized oligomers were considered to have greater contribution to the cerebral Aβ accumulation than 2C3-recognized oligomers.

The involvement of the polymers in cerebral Aβ accumulation can be explained based on the following assumption: neurotoxic 1A9 polymers are soluble toxic oligomers that are somewhat conformationally, while neurotoxic 2C3 polymers are very unstable, short-lived oligomeric intermediates that appear at an early stage of the polymerization process, the conformation of which is easily changed.

The present inventors disclose herein the in vivo preventive effect of anti-oligomer antibodies on Alzheimer's disease, and this is the first evidence that directly demonstrates that toxic Aβ oligomers formed in vivo can inhibit the functions of nerve cells, thereby inducing the symptoms of Alzheimer's disease.

The data obtained by the present inventors is also the first evidence supporting the view that Aβ exhibits in vivo neurotoxicity in the human brain. It is well known that the human entorhinal cortex is an area that is easily affected with AD. In this area, NFT formation and nerve cell loss precede the formation of senile plaques. Thus, the entorhinal cortex is an exceptional area to which the commonly accepted amyloid cascade hypothesis cannot be applied. However, this inconsistency has been neglected and remained unstudied for a long time.

The present inventors proposed and examined the hypothesis that previously unidentifiable, invisible Aβ oligomers are harmful for nerve cells in the entorhinal cortex and cause memory disturbance. To examine this hypothesis, the present inventors performed semi-quantitative analysis of 1A9- and 2C3-immunoreactive 12mer in the entorhinal cortex of elderly individuals who were mostly at Braak NFT stages I to III. The 1A9- and 2C3-immunoreactive 12mer were already present in the entorhinal cortex of healthy individuals at Braak NFT stages I to II, and increased with the advancement of Braak NFT stage. The 12mer was found to be significantly increased in AD. Thus, the appearance of 1A9- and 2C3-immunoreactive 12mer was demonstrated to precede the onset of cognitive impairment in the human brain. On the other hand, by biochemical and immunohistochemical techniques, it was demonstrated that senile plaques contain 1A9- and 2C3-immunoreactive Aβ oligomers. In addition, insolubilized amyloid fibrils themselves were revealed to have an activity of neutralizing the neurotoxicity. These findings suggest that, under conditions where Aβ oligomers are present without senile plaque formation, Aβ oligomers exert in vivo toxicity and thus can be a cause of memory disturbance.

As described above, the data of the present inventors show for the first time evidence that directly demonstrates in vivo the memory disturbance resulting from synaptic dysfunction caused by endogenous Aβ oligomers. Although active immunotherapy (Janus D, 2000, Nature; Morgan D, 2000, Nature) and passive immunotherapy (Bard F, 2222, Nat med; DeMattos R B, PNAS, 2001) have been used previously, the mechanism by which learning disability and memory disturbance can be prevented has remained a matter of conjecture. One widely proposed possibility is that the antibodies reach the brain through the blood-brain barrier and directly neutralize in vivo soluble Aβ oligomers that cause memory impairment. The second possibility, the "sink theory", is that the antibodies act peripherally to deplete the peripheral blood Aβ pool and thus activate Aβ clearance from the brain. DeMattos et al. have reported that a peripherally administered anti-Aβ antibody rapidly transports not only cerebral Aβ monomers but also Aβ dimers into plasma, and also cerebral Aβ into CSF (DeMattos R B et al., PNAS, 98; 8850-8855, 2001). The present inventors also revealed that Aβ oligomers are present in human CSF and increased in AD patients. Thus, the present inventors demonstrated that the Aβ oligomers can be used as diagnostic markers for AD. Furthermore, the present inventors presented the first evidence supporting the view that Aβ oligomers are present in the plasma of Tg2576 mice, and, in passive immunotherapy by which Aβ oligomers are specifically captured and neutralized through intravenous injection, intracerebral antibody delivery is not required and the clearance of Aβ oligomers from the brain to blood can be enhanced at the peripheral sites of action, i.e., blood vessels. In addition, the present inventors presented the first evidence that passive immunotherapy can suppress senile amyloid plaque formation, and indirectly suppress nerve cell damage (swollen dystrophic neurite formation) through senile amyloid plaque suppression. These results confirm that the Aβ oligomer is the molecular basis for the onset of Alzheimer's disease, and selective control using oligomer-specific antibodies enables the control of Alzheimer's disease from a prophylactic viewpoint, in addition to a therapeutic viewpoint. Furthermore, a fraction of the administered antibodies was proven to translocate into the brain. This suggests that the effect of suppressing memory disturbance is exerted by a combination of multiple actions such as direct neutralization of soluble Aβ oligomers in the brain, transport of antibody-Aβ oligomer immune complexes into blood by the neonatal Fc receptor (Deane R, 2005, J Neurosci), and the "sink" action described above.

The establishment of accurate pre-onset diagnosis to identify cases at a high risk of developing AD is essential to design preventive/therapeutic strategies. The significant increase in the CSF O/M ratio in AD, which is reported herein, is expected to be one of the leading candidates for pre-onset diagnostic markers.

INDUSTRIAL APPLICABILITY

The antibodies provided by the present invention can be used, for example, in intravenous injection-based preventive passive immunotherapy for Alzheimer's disease, and as biological markers for pre-onset diagnosis, disease monitoring, drug efficacy monitoring/assessment for the disease, and such.

Furthermore, the antibodies of the present invention are expected to greatly contribute to the establishment of preventive/therapeutic methods for Alzheimer's disease that are selective to molecules responsible for evoking the pathological conditions of the disease, and the establishment of early diagnostic markers. The present inventors obtained evidence supporting that antibody therapies, even when they target intracerebral pathological conditions, can be satisfactorily achieved by peripheral intravenous administration, without the need to consider intracerebral transfer of the antibodies. In addition, the present inventors obtained evidence demonstrating that a fraction of administered antibodies translocates to the brain and produces a direct effect even in peripheral intravenous administration therapy, again without the need to consider intracerebral transfer of the antibodies. Thus, the present invention is expected to rapidly accelerate the progress of antibody therapeutics for Alzheimer's disease.

The invention claimed is:

1. An isolated antibody that binds to an Aβ oligomer and which comprises an H chain having the amino acid sequence of SEQ ID NO: 81, an L chain having the amino acid sequence of SEQ ID NO: 83, or both.

2. An isolated antibody that binds to an Aβ oligomer, and which is selected from the group consisting of:
   (1) an antibody that comprises (i) an H chain having the amino acid sequence of SEQ ID NO: 89 as CDR1, the amino acid sequence of SEQ ID NO: 91 as CDR2, and the amino acid sequence of SEQ ID NO: 93 as CDR3; and (ii) an L chain having the amino acid sequence of SEQ ID NO: 95 as CDR1, the amino acid sequence of SEQ ID NO: 97 as CDR2, and the amino acid sequence of SEQ ID NO: 99 as CDR3;
   (2) an antibody that comprises an H chain having the amino acid sequence of SEQ ID NO: 85 as VH; and
   (3) an antibody that comprises (i) an H chain having the amino acid sequence of SEQ ID NO: 85 as VH and (ii) an L chain having the amino acid sequence of SEQ ID NO: 87 as VL.

3. The antibody of claim 2, wherein the antibody is a chimeric antibody or a humanized antibody.

4. A composition comprising the antibody of claim 1 or 2 and a pharmaceutically acceptable carrier.

* * * * *

SEQUENCE LISTING

<160> NUMBER OF SEQ ID NOS: 120

<210> SEQ ID NO 1
<211> LENGTH: 452
<212> TYPE: PRT
<213> ORGANISM: Mus musculus

<400> SEQUENCE: 1

```
Asp Val Gln Leu Val Glu Ser Gly Gly Gly Leu Val Gln Pro Gly Gly
 1               5                  10                  15

Ser Arg Lys Leu Ser Cys Ala Thr Ser Gly Phe Thr Phe Ser Ser Phe
            20                  25                  30

Gly Met His Trp Val Arg Gln Ala Pro Glu Lys Gly Leu Glu Trp Val
        35                  40                  45

Ala Tyr Ile Ser Ser Gly Ser Ser Ala Ile Tyr Tyr Ala Asp Thr Val
    50                  55                  60

Lys Gly Arg Phe Thr Ile Ser Arg Asp Asn Pro Lys Asn Thr Leu Phe
65                  70                  75                  80

Leu Gln Met Thr Ser Leu Arg Ser Glu Asp Thr Ala Met Tyr Tyr Cys
                85                  90                  95

Ala Arg Ser Gly Asp Thr Met Asp Tyr Trp Gly Gln Gly Thr Ser Val
            100                 105                 110

Thr Val Ser Ser Ala Lys Thr Thr Pro Pro Ser Val Tyr Pro Leu Ala
        115                 120                 125

Pro Gly Cys Gly Asp Thr Gly Ser Ser Val Thr Leu Gly Cys Leu
    130                 135                 140

Val Lys Gly Tyr Phe Pro Glu Ser Val Thr Val Thr Trp Asn Ser Gly
145                 150                 155                 160

Ser Leu Ser Ser Ser Val His Thr Phe Pro Ala Leu Leu Gln Ser Gly
                165                 170                 175

Leu Tyr Thr Met Ser Ser Ser Val Thr Val Pro Ser Ser Thr Trp Pro
            180                 185                 190

Ser Gln Thr Val Thr Cys Ser Val Ala His Pro Ala Ser Ser Thr Thr
        195                 200                 205

Val Asp Lys Lys Leu Glu Pro Ser Gly Pro Ile Ser Thr Ile Asn Pro
    210                 215                 220

Cys Pro Pro Cys Lys Glu Cys His Lys Cys Pro Ala Pro Asn Leu Glu
225                 230                 235                 240

Gly Gly Pro Ser Val Phe Ile Phe Pro Pro Asn Ile Lys Asp Val Leu
                245                 250                 255

Met Ile Ser Leu Thr Pro Lys Val Thr Cys Val Val Val Asp Val Ser
            260                 265                 270

Glu Asp Asp Pro Asp Val Gln Ile Ser Trp Phe Val Asn Asn Val Glu
        275                 280                 285

Val His Thr Ala Gln Thr Gln Thr His Arg Glu Asp Tyr Asn Ser Thr
    290                 295                 300

Ile Arg Val Val Ser Thr Leu Pro Ile Gln His Gln Asp Trp Met Ser
305                 310                 315                 320

Gly Lys Glu Phe Lys Cys Lys Val Asn Asn Lys Asp Leu Pro Ser Pro
                325                 330                 335

Ile Glu Arg Thr Ile Ser Lys Ile Lys Gly Leu Val Arg Ala Pro Gln
            340                 345                 350

Val Tyr Ile Leu Pro Pro Ala Glu Gln Leu Ser Arg Lys Asp Val
        355                 360                 365
```

```
Ser Leu Thr Cys Leu Val Val Gly Phe Asn Pro Gly Asp Ile Ser Val
    370                 375                 380
Glu Trp Thr Ser Asn Gly His Thr Glu Glu Asn Tyr Lys Asp Thr Ala
385                 390                 395                 400
Pro Val Leu Asp Ser Asp Gly Ser Tyr Phe Ile Tyr Ser Lys Leu Asn
                405                 410                 415
Met Lys Thr Ser Lys Trp Glu Lys Thr Asp Ser Phe Ser Cys Asn Val
            420                 425                 430
Arg His Glu Gly Leu Lys Asn Tyr Tyr Leu Lys Thr Ile Ser Arg
        435                 440                 445
Ser Pro Gly Lys
    450

<210> SEQ ID NO 2
<211> LENGTH: 1359
<212> TYPE: DNA
<213> ORGANISM: Mus musculus

<400> SEQUENCE: 2
```

| | |
|---|---:|
| gatgtgcagc tggtggagtc tgggggaggc ttagtgcagc ctggagggtc ccggaaactc | 60 |
| tcctgtgcaa cctctggatt cactttcagt agctttggaa tgcactgggt tcgtcaggct | 120 |
| ccagagaagg gactggagtg gtcgcatac attagtagtg gcagtagtgc catctactat | 180 |
| gcagacacag tgaagggccg attcaccatc tccagagaca atcccaagaa caccctgttc | 240 |
| ctgcaaatga ccagtctaag gtctgaggac acggccatgt attactgtgc aagatctggg | 300 |
| gatactatgg actactgggg tcaaggaacc tcagtcaccg tctcctcagc caaaacaaca | 360 |
| cccccatcag tctatccact ggcccctggg tgtggagata caactggttc ctccgtgact | 420 |
| ctgggatgcc tggtcaaggg ctacttccct gagtcagtga ctgtgacttg aactctgga | 480 |
| tccctgtcca gcagtgtgca caccttccca gctctcctgc agtctggact ctacactatg | 540 |
| agcagctcag tgactgtccc ctccagcacc tggccaagtc agaccgtcac ctgcagcgtt | 600 |
| gctcacccag ccagcagcac cacggtggac aaaaaacttg agcccagcgg gcccatttca | 660 |
| acaatcaacc cctgtcctcc atgcaaggag tgtcacaaat gcccagctcc taacctcgag | 720 |
| ggtggaccat ccgtcttcat cttccctcca aatatcaagg atgtactcat gatctccctg | 780 |
| acacccaagg tcacgtgtgt ggtggtggat gtgagcgagg atgacccaga cgtccagatc | 840 |
| agctggtttg tgaacaacgt ggaagtacac acagctcaga cacaaaccca tagagaggat | 900 |
| tacaacagta ctatccgggt ggtcagcacc ctccccatcc agcaccagga ctggatgagt | 960 |
| ggcaaggagt tcaaatgcaa ggtcaacaac aaagacctcc catcacccat cgagagaacc | 1020 |
| atctcaaaaa ttaaagggct agtcagagct ccacaagtat acatcttgcc gccaccagca | 1080 |
| gagcagttgt ccaggaaaga tgtcagtctc acttgcctgg tcgtgggctt caaccctgga | 1140 |
| gacatcagtg tggagtggac cagcaatggg catacagagg agaactacaa ggacaccgca | 1200 |
| ccagtcctgg actctgacgg ttcttacttc atatatagca agctcaatat gaaaacaagc | 1260 |
| aagtgggaga aacagattc cttctcatgc aacgtgagac acgagggtct gaaaaattac | 1320 |
| tacctgaaga agaccatctc ccggtctccg ggtaaatga | 1359 |

```
<210> SEQ ID NO 3
<211> LENGTH: 219
<212> TYPE: PRT
<213> ORGANISM: Mus musculus

<400> SEQUENCE: 3
```

Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Asn Ile Val His Ser
            20                  25                  30

Asn Gly Asn Thr Tyr Leu Glu Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65              70                  75                  80

Ser Ser Val Glu Ala Glu Asp Leu Gly Val Tyr Tyr Cys Phe Gln Val
                85                  90                  95

Ser His Val Pro Pro Thr Phe Gly Gly Gly Thr Lys Leu Glu Ile Lys
            100                 105                 110

Arg Ala Asp Ala Ala Pro Thr Val Ser Ile Phe Pro Pro Ser Ser Glu
        115                 120                 125

Gln Leu Thr Ser Gly Gly Ala Ser Val Val Cys Phe Leu Asn Asn Phe
    130                 135                 140

Tyr Pro Lys Asp Ile Asn Val Lys Trp Lys Ile Asp Gly Ser Glu Arg
145                 150                 155                 160

Gln Asn Gly Val Leu Asn Ser Trp Thr Asp Gln Asp Ser Lys Asp Ser
                165                 170                 175

Thr Tyr Ser Met Ser Ser Thr Leu Thr Leu Thr Lys Asp Glu Tyr Glu
            180                 185                 190

Arg His Asn Ser Tyr Thr Cys Glu Ala Thr His Lys Thr Ser Thr Ser
        195                 200                 205

Pro Ile Val Lys Ser Phe Asn Arg Asn Glu Cys
    210                 215

<210> SEQ ID NO 4
<211> LENGTH: 660
<212> TYPE: DNA
<213> ORGANISM: Mus musculus

<400> SEQUENCE: 4
gatgttttga tgacccaaac tccactctcc ctgcctgtca gtcttggaga tcaagcctcc      60
atctcttgca gatctagtca gaacattgta catagtaatg gaaacaccta tttagaatgg     120
tacctgcaga aaccaggcca gtctccaaag ctcctgatct acaaagtttc caaccgattt     180
tctggggtcc cagacaggtt cagtggcagt ggatcaggga cagatttcac actcaagatc     240
agcagcgtgg aggctgagga tctgggagtt tattactgct ttcaagtttc acatgttcct     300
ccgacgttcg gtggaggcac caagctggaa atcaaacggg ctgatgctgc accaactgta     360
tccatcttcc caccatccag tgagcagtta acatctggag gtgcctcagt cgtgtgcttc     420
ttgaacaact tctaccccaa agacatcaat gtcaagtgga agattgatgg cagtgaacga     480
caaaatggcg tcctgaacag ttggactgat caggacagca agacagcac ctacagcatg     540 agcagtaccc tcacgttgac caaggacgag tatgaacgac ataacagcta cctgtgag     600 gccactcaca agacatcaac ttcacccatt gtcaagagct caacaggaa tgagtgttag      660

<210> SEQ ID NO 5
<211> LENGTH: 116
<212> TYPE: PRT
<213> ORGANISM: Mus musculus

<400> SEQUENCE: 5

Asp Val Gln Leu Val Glu Ser Gly Gly Leu Val Gln Pro Gly Gly
1               5                   10                  15

Ser Arg Lys Leu Ser Cys Ala Thr Ser Gly Phe Thr Phe Ser Ser Phe
            20                  25                  30

Gly Met His Trp Val Arg Gln Ala Pro Glu Lys Gly Leu Glu Trp Val
            35                  40                  45

Ala Tyr Ile Ser Ser Gly Ser Ser Ala Ile Tyr Tyr Ala Asp Thr Val
    50                  55                  60

Lys Gly Arg Phe Thr Ile Ser Arg Asp Asn Pro Lys Asn Thr Leu Phe
65                  70                  75                  80

Leu Gln Met Thr Ser Leu Arg Ser Glu Asp Thr Ala Met Tyr Tyr Cys
                85                  90                  95

Ala Arg Ser Gly Asp Thr Met Asp Tyr Trp Gly Gln Gly Thr Ser Val
            100                 105                 110

Thr Val Ser Ser
        115

<210> SEQ ID NO 6
<211> LENGTH: 348
<212> TYPE: DNA
<213> ORGANISM: Mus musculus

<400> SEQUENCE: 6
gatgtgcagc tggtggagtc tgggggaggc ttagtgcagc ctggagggtc ccggaaactc      60
tcctgtgcaa cctctggatt cactttcagt agctttggaa tgcactgggt tcgtcaggct     120
ccagagaagg gactggagtg ggtcgcatac attagtagtg gcagtagtgc catctactat     180
gcagacacac tgaagggccg attcaccatc tccagagaca atcccaagaa caccctgttc     240
ctgcaaatga ccagtctaag gtctgaggac acggccatgt attactgtgc aagatctggg     300
gatactatgg actactgggg tcaaggaacc tcagtcaccg tctcctca                  348

<210> SEQ ID NO 7
<211> LENGTH: 112
<212> TYPE: PRT
<213> ORGANISM: Mus musculus

<400> SEQUENCE: 7

Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Asn Ile Val His Ser
            20                  25                  30

Asn Gly Asn Thr Tyr Leu Glu Trp Tyr Leu Gln Lys Pro Gly Gln Ser
            35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Ser Val Glu Ala Glu Asp Leu Gly Val Tyr Tyr Cys Phe Gln Val
                85                  90                  95

Ser His Val Pro Pro Thr Phe Gly Gly Gly Thr Lys Leu Glu Ile Lys
            100                 105                 110

<210> SEQ ID NO 8
<211> LENGTH: 336
<212> TYPE: DNA
<213> ORGANISM: Mus musculus -continued

<400> SEQUENCE: 8

```
gatgttttga tgacccaaac tccactctcc ctgcctgtca gtcttggaga tcaagcctcc      60
atctcttgca gatctagtca gaacattgta catagtaatg gaaacaccta tttagaatgg    120
tacctgcaga aaccaggcca gtctccaaag ctcctgatct acaaagtttc caaccgattt    180
tctggggtcc cagacaggtt cagtggcagt ggatcaggga cagatttcac actcaagatc    240
agcagcgtgg aggctgagga tctgggagtt tattactgct ttcaagtttc acatgttcct    300
ccgacgttcg gtggaggcac caagctggaa atcaaa                              336
```

<210> SEQ ID NO 9
<211> LENGTH: 5
<212> TYPE: PRT
<213> ORGANISM: Mus musculus

<400> SEQUENCE: 9

Ser Phe Gly Met His
1               5

<210> SEQ ID NO 10
<211> LENGTH: 15
<212> TYPE: DNA
<213> ORGANISM: Mus musculus

<400> SEQUENCE: 10

```
agctttggaa tgcac                                                       15
```

<210> SEQ ID NO 11
<211> LENGTH: 10
<212> TYPE: PRT
<213> ORGANISM: Mus musculus

<400> SEQUENCE: 11

Tyr Ile Ser Ser Gly Ser Ser Ala Ile Tyr
1               5                   10

<210> SEQ ID NO 12
<211> LENGTH: 30
<212> TYPE: DNA
<213> ORGANISM: Mus musculus

<400> SEQUENCE: 12

```
tacattagta gtggcagtag tgccatctac                                       30
```

<210> SEQ ID NO 13
<211> LENGTH: 7
<212> TYPE: PRT
<213> ORGANISM: Mus musculus

<400> SEQUENCE: 13

Ser Gly Asp Thr Met Asp Tyr
1               5

<210> SEQ ID NO 14
<211> LENGTH: 21
<212> TYPE: DNA
<213> ORGANISM: Mus musculus

<400> SEQUENCE: 14

```
tctggggata ctatggacta c                                                21
```

<210> SEQ ID NO 15
<211> LENGTH: 16

```
<212> TYPE: PRT
<213> ORGANISM: Mus musculus

<400> SEQUENCE: 15

Arg Ser Ser Gln Asn Ile Val His Ser Asn Gly Asn Thr Tyr Leu Glu
1               5                   10                  15

<210> SEQ ID NO 16
<211> LENGTH: 48
<212> TYPE: DNA
<213> ORGANISM: Mus musculus

<400> SEQUENCE: 16
agatctagtc agaacattgt acatagtaat ggaaacacct atttagaa                   48

<210> SEQ ID NO 17
<211> LENGTH: 7
<212> TYPE: PRT
<213> ORGANISM: Mus musculus

<400> SEQUENCE: 17

Lys Val Ser Asn Arg Phe Ser
1               5

<210> SEQ ID NO 18
<211> LENGTH: 21
<212> TYPE: DNA
<213> ORGANISM: Mus musculus

<400> SEQUENCE: 18
aaagtttcca accgattttc t                                                21

<210> SEQ ID NO 19
<211> LENGTH: 9
<212> TYPE: PRT
<213> ORGANISM: Mus musculus

<400> SEQUENCE: 19

Phe Gln Val Ser His Val Pro Pro Thr
1               5

<210> SEQ ID NO 20
<211> LENGTH: 27
<212> TYPE: DNA
<213> ORGANISM: Mus musculus

<400> SEQUENCE: 20
tttcaagttt cacatgttcc tccgacg                                          27

<210> SEQ ID NO 21
<211> LENGTH: 455
<212> TYPE: PRT
<213> ORGANISM: Mus musculus

<400> SEQUENCE: 21

Gln Val Thr Leu Lys Glu Ser Gly Pro Gly Ile Leu Gln Pro Ser Gln
1               5                   10                  15

Thr Leu Ser Leu Thr Cys Ser Phe Ser Gly Phe Ser Leu Thr Thr Ser
            20                  25                  30

Ala Met Gly Val Ser Trp Val Arg Gln Pro Ser Arg Lys Gly Leu Glu
        35                  40                  45

Trp Leu Ala His Ile Tyr Trp Asp Asp Lys Arg Tyr Asn Pro Ser
    50                  55                  60
```

Leu Lys Ser Arg Leu Thr Ile Ser Lys Asp Thr Ser Asn Gln Val
 65                  70                  75                  80

Phe Leu Lys Ile Thr Ser Val Asp Thr Ala Asp Thr Ala Thr Tyr Tyr
             85                  90                  95

Cys Ala Arg Lys Gly Leu Gly Gly Ala Met Asp Tyr Trp Gly Gln Gly
            100                 105                 110

Thr Ser Val Thr Val Ser Ser Ala Lys Thr Thr Pro Pro Ser Val Tyr
        115                 120                 125

Pro Leu Ala Pro Gly Cys Gly Asp Thr Thr Gly Ser Ser Val Thr Leu
    130                 135                 140

Gly Cys Leu Val Lys Gly Tyr Phe Pro Glu Ser Val Thr Val Thr Trp
145                 150                 155                 160

Asn Ser Gly Ser Leu Ser Ser Ser Val His Thr Phe Pro Ala Leu Leu
                165                 170                 175

Gln Ser Gly Leu Tyr Thr Met Ser Ser Ser Val Thr Val Pro Ser Ser
            180                 185                 190

Thr Trp Pro Ser Gln Thr Val Thr Cys Ser Val Ala His Pro Ala Ser
        195                 200                 205

Ser Thr Thr Val Asp Lys Lys Leu Glu Pro Ser Gly Pro Ile Ser Thr
    210                 215                 220

Ile Asn Pro Cys Pro Pro Cys Lys Glu Cys His Lys Cys Pro Ala Pro
225                 230                 235                 240

Asn Leu Glu Gly Gly Pro Ser Val Phe Ile Phe Pro Pro Asn Ile Lys
                245                 250                 255

Asp Val Leu Met Ile Ser Leu Thr Pro Lys Val Thr Cys Val Val Val
            260                 265                 270

Asp Val Ser Glu Asp Asp Pro Asp Val Gln Ile Ser Trp Phe Val Asn
        275                 280                 285

Asn Val Glu Val His Thr Ala Gln Thr Gln Thr His Arg Glu Asp Tyr
    290                 295                 300

Asn Ser Thr Ile Arg Val Val Ser Thr Leu Pro Ile Gln His Gln Asp
305                 310                 315                 320

Trp Met Ser Gly Lys Glu Phe Lys Cys Lys Val Asn Asn Lys Asp Leu
                325                 330                 335

Pro Ser Pro Ile Glu Arg Thr Ile Ser Lys Ile Lys Gly Leu Val Arg
            340                 345                 350

Ala Pro Gln Val Tyr Ile Leu Pro Pro Ala Glu Gln Leu Ser Arg
        355                 360                 365

Lys Asp Val Ser Leu Thr Cys Leu Val Val Gly Phe Asn Pro Gly Asp
    370                 375                 380

Ile Ser Val Glu Trp Thr Ser Asn Gly His Thr Glu Glu Asn Tyr Lys
385                 390                 395                 400

Asp Thr Ala Pro Val Leu Asp Ser Asp Gly Ser Tyr Phe Ile Tyr Ser
                405                 410                 415

Lys Leu Asn Met Lys Thr Ser Lys Trp Glu Lys Thr Asp Ser Phe Ser
            420                 425                 430

Cys Asn Val Arg His Glu Gly Leu Lys Asn Tyr Tyr Leu Lys Lys Thr
        435                 440                 445

Ile Ser Arg Ser Pro Gly Lys
    450                 455

<210> SEQ ID NO 22
<211> LENGTH: 1368
<212> TYPE: DNA
<213> ORGANISM: Mus musculus

<400> SEQUENCE: 22

```
caggttactc tgaaagagtc tggccctggg atattgcagc cctcccagac cctcagtctg      60
acttgttctt tctctggatt ttcactgacc acttctgcta tgggtgtgag ctgggttcgt     120
cagccttcaa gaaagggtct ggagtggctg gcacacattt actgggatga tgacaagcgc     180
tataacccat ccctgaagag ccggctcaca atctccaagg atacctccag caaccaggta     240
ttcctcaaga tcaccagtgt ggacactgca gatactgcca catactactg tgctcgaaag     300
ggactgggag gtgctatgga ctactggggt caaggaacct cagtcaccgt ctcctcagcc     360
aaaacaacac ccccatcagt ctatccactg gcccctgggt gtggagatac aactggttcc     420
tccgtgactc tgggatgcct ggtcaagggc tacttccctg agtcagtgac tgtgacttgg     480
aactctggat ccctgtccag cagtgtgcac accttcccag ctctcctgca gtctggactc     540
tacactatga gcagctcagt gactgtcccc tccagcacct ggccaagtca gaccgtcacc     600
tgcagcgttg ctcacccagc cagcagcacc acggtggaca aaaaacttga gcccagcggg     660
cccatttcaa caatcaaccc ctgtcctcca tgcaaggagt gtcacaaatg cccagctcct     720
aacctcgagg gtggaccatc cgtcttcatc ttccctccaa atatcaagga tgtactcatg     780
atctccctga cacccaaggt cacgtgtgtg gtggtggatg tgagcgagga tgacccagac     840
gtccagatca gctggttttgt gaacaacgtg aagtacacag agctcagac acaaacccat     900
agagaggatt acaacagtac tatccgggtg gtcagcaccc tccccatcca gcaccaggac     960
tggatgagtg gcaaggagtt caatgcaag gtcaacaaca agacctccc atcacccatc    1020
gagagaacca tctcaaaaat taagggcta gtcagagctc acaagtata catcttgccg    1080
ccaccagcag agcagttgtc caggaaagat gtcagtctca cttgcctggt cgtgggcttc    1140
aaccctggag acatcagtgt ggagtggacc agcaatgggc atacagagga gaactacaag    1200
gacaccgcac cagtcctgga ctctgacggt tcttacttca tatatagcaa gctcaatatg    1260
aaaacaagca agtgggagaa acagattcc ttctcatgca cgtgagaca cgagggtctg    1320
aaaaattact acctgaagaa gaccatctcc cggtctccgg gtaaatga              1368
```

<210> SEQ ID NO 23
<211> LENGTH: 219
<212> TYPE: PRT
<213> ORGANISM: Mus musculus

<400> SEQUENCE: 23

```
Asp Val Val Met Thr Gln Thr Pro Leu Ser Leu Pro Val Ser Leu Gly
  1               5                  10                  15

Asp Gln Ala Ser Ile Ser Cys Arg Ser Ser Gln Ser Leu Leu His Ser
             20                  25                  30

Asn Gly Asn Thr Tyr Leu His Trp Tyr Leu Gln Lys Pro Gly Gln Ser
         35                  40                  45

Pro Lys Leu Leu Ile Tyr Lys Val Ser Asn Arg Phe Ser Gly Val Pro
     50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Leu Gly Val Tyr Phe Cys Ser Gln Ser
                 85                  90                  95

Thr His Val Pro Leu Thr Phe Gly Ala Gly Thr Lys Leu Glu Leu Lys
            100                 105                 110

Arg Ala Asp Ala Ala Pro Thr Val Ser Ile Phe Pro Pro Ser Ser Glu
        115                 120                 125
```

Gln Leu Thr Ser Gly Gly Ala Ser Val Val Cys Phe Leu Asn Asn Phe
    130                 135                 140

Tyr Pro Lys Asp Ile Asn Val Lys Trp Lys Ile Asp Gly Ser Glu Arg
145                 150                 155                 160

Gln Asn Gly Val Leu Asn Ser Trp Thr Asp Gln Asp Ser Lys Asp Ser
                165                 170                 175

Thr Tyr Ser Met Ser Ser Thr Leu Thr Leu Thr Lys Asp Glu Tyr Glu
            180                 185                 190

Arg His Asn Ser Tyr Thr Cys Glu Ala Thr His Lys Thr Ser Thr Ser
        195                 200                 205

Pro Ile Val Lys Ser Phe Asn Arg Asn Glu Cys
    210                 215

<210> SEQ ID NO 24
<211> LENGTH: 660
<212> TYPE: DNA
<213> ORGANISM: Mus musculus

<400> SEQUENCE: 24
gatgttgtga tgacccaaac tccgctctcc ctgcctgtca gtcttggaga tcaagcctcc      60
atctcttgca gatctagtca gagccttcta cacagtaatg aaacacccta tttacattgg    120
tacctgcaga agccaggcca gtctccaaag ctcctgatct acaaagtttc caaccgattt    180
tctggggtcc cagacaggtt cagtggcagt ggatcaggga cagatttcac actcaagatc    240
agcagagtgg aggctgagga tctgggagtt tatttctgct ctcaaagtac acatgttccg    300
ctcacgttcg gtgctgggac caagctggag ctgaacgggc tgatgctgca ccaactgta    360 tccatcttcc caccatccag tgagcagtta acatctggag gtgcctcagt cgtgtgcttc    420
ttgaacaact ctacccccaa agacatcaat gtcaagtgga agattgatgg cagtgaacga    480
caaaatggcg tcctgaacag ttggactgat caggacagca agacagcac ctacagcatg    540 agcagtaccc tcacgttgac caaggacgag tatgaacgac ataacagcta cctgtgagg    600 gccactcaca agacatcaac ttcacccatt gtcaagagct caacaggaa tgagtgttag    660

<210> SEQ ID NO 25
<211> LENGTH: 119
<212> TYPE: PRT
<213> ORGANISM: Mus musculus

<400> SEQUENCE: 25

Gln Val Thr Leu Lys Glu Ser Gly Pro Gly Ile Leu Gln Pro Ser Gln
1               5                   10                  15

Thr Leu Ser Leu Thr Cys Ser Phe Ser Gly Phe Ser Leu Thr Thr Ser
            20                  25                  30

Ala Met Gly Val Ser Trp Val Arg Gln Pro Ser Arg Lys Gly Leu Glu
        35                  40                  45

Trp Leu Ala His Ile Tyr Trp Asp Asp Lys Arg Tyr Asn Pro Ser
    50                  55                  60

Leu Lys Ser Arg Leu Thr Ile Ser Lys Asp Thr Ser Ser Asn Gln Val
65                  70                  75                  80

Phe Leu Lys Ile Thr Ser Val Asp Thr Ala Asp Thr Ala Thr Tyr Tyr
                85                  90                  95

Cys Ala Arg Lys Gly Leu Gly Gly Ala Met Asp Tyr Trp Gly Gln Gly
            100                 105                 110

Thr Ser Val Thr Val Ser Ser
        115

-continued

<210> SEQ ID NO 26
<211> LENGTH: 357
<212> TYPE: DNA
<213> ORGANISM: Mus musculus

<400> SEQUENCE: 26

```
caggttactc tgaaagagtc tggccctggg atattgcagc cctcccagac cctcagtctg      60
acttgttctt tctctggatt ttcactgacc acttctgcta tgggtgtgag ctgggttcgt     120
cagccttcaa gaaagggtct ggagtggctg gcacacattt actgggatga tgacaagcgc     180
tataacccat ccctgaagag ccggctcaca atctccaagg atacctccag caaccaggta     240
ttcctcaaga tcaccagtgt ggacactgca gatactgcca catactactg tgctcgaaag     300
ggactgggag gtgctatgga ctactggggt caaggaacct cagtcaccgt ctcctca       357
```

<210> SEQ ID NO 27
<211> LENGTH: 112
<212> TYPE: PRT
<213> ORGANISM: Mus musculus

<400> SEQUENCE: 27

```
Asp Val Val Met Thr Gln Thr Pro Leu Ser Leu Pro Val Ser Leu Gly
1               5                   10                  15
Asp Gln Ala Ser Ile Ser Cys Arg Ser Ser Gln Ser Leu Leu His Ser
            20                  25                  30
Asn Gly Asn Thr Tyr Leu His Trp Tyr Leu Gln Lys Pro Gly Gln Ser
        35                  40                  45
Pro Lys Leu Leu Ile Tyr Lys Val Ser Asn Arg Phe Ser Gly Val Pro
    50                  55                  60
Asp Arg Phe Ser Gly Ser Gly Ser Gly Thr Asp Phe Thr Leu Lys Ile
65                  70                  75                  80
Ser Arg Val Glu Ala Glu Asp Leu Gly Val Tyr Phe Cys Ser Gln Ser
                85                  90                  95
Thr His Val Pro Leu Thr Phe Gly Ala Gly Thr Lys Leu Glu Leu Lys
            100                 105                 110
```

<210> SEQ ID NO 28
<211> LENGTH: 336
<212> TYPE: DNA
<213> ORGANISM: Mus musculus

<400> SEQUENCE: 28

```
gatgttgtga tgacccaaac tccgctctcc ctgcctgtca gtcttggaga tcaagcctcc      60
atctcttgca gatctagtca gagccttcta cacagtaatg gaaacaccta tttacattgg     120
tacctgcaga agccaggcca gtctccaaag ctcctgatct acaaagtttc caaccgattt     180
tctggggtcc cagacaggtt cagtggcagt ggatcaggga cagatttcac actcaagatc     240
agcagagtgg aggctgagga tctgggagtt tatttctgct ctcaaagtac acatgttccg     300
ctcacgttcg gtgctgggac caagctggag ctgaaa                              336
```

<210> SEQ ID NO 29
<211> LENGTH: 7
<212> TYPE: PRT
<213> ORGANISM: Mus musculus

<400> SEQUENCE: 29

```
Thr Ser Ala Met Gly Val Ser
1               5
```

<210> SEQ ID NO 30
<211> LENGTH: 21
<212> TYPE: DNA
<213> ORGANISM: Mus musculus

<400> SEQUENCE: 30
acttctgcta tgggtgtgag c                                              21

<210> SEQ ID NO 31
<211> LENGTH: 9
<212> TYPE: PRT
<213> ORGANISM: Mus musculus

<400> SEQUENCE: 31

His Ile Tyr Trp Asp Asp Asp Lys Arg
1               5

<210> SEQ ID NO 32
<211> LENGTH: 27
<212> TYPE: DNA
<213> ORGANISM: Mus musculus

<400> SEQUENCE: 32
cacatttact gggatgatga caagcgc                                        27

<210> SEQ ID NO 33
<211> LENGTH: 9
<212> TYPE: PRT
<213> ORGANISM: Mus musculus

<400> SEQUENCE: 33

Lys Gly Leu Gly Gly Ala Met Asp Tyr
1               5

<210> SEQ ID NO 34
<211> LENGTH: 27
<212> TYPE: DNA
<213> ORGANISM: Mus musculus

<400> SEQUENCE: 34
aagggactgg gaggtgctat ggactac                                        27

<210> SEQ ID NO 35
<211> LENGTH: 16
<212> TYPE: PRT
<213> ORGANISM: Mus musculus

<400> SEQUENCE: 35

Arg Ser Ser Gln Ser Leu Leu His Ser Asn Gly Asn Thr Tyr Leu His
1               5                   10                  15

<210> SEQ ID NO 36
<211> LENGTH: 48
<212> TYPE: DNA
<213> ORGANISM: Mus musculus

<400> SEQUENCE: 36
agatctagtc agagccttct acacagtaat ggaaacacct atttacat                 48

<210> SEQ ID NO 37
<211> LENGTH: 7
<212> TYPE: PRT
<213> ORGANISM: Mus musculus

<400> SEQUENCE: 37

Lys Val Ser Asn Arg Phe Ser
1               5

<210> SEQ ID NO 38
<211> LENGTH: 21
<212> TYPE: DNA
<213> ORGANISM: Mus musculus

<400> SEQUENCE: 38
aaagtttcca accgattttc t                                              21

<210> SEQ ID NO 39
<211> LENGTH: 9
<212> TYPE: PRT
<213> ORGANISM: Mus musculus

<400> SEQUENCE: 39

Ser Gln Ser Thr His Val Pro Leu Thr
1               5

<210> SEQ ID NO 40
<211> LENGTH: 27
<212> TYPE: DNA
<213> ORGANISM: Mus musculus

<400> SEQUENCE: 40
tctcaaagta cacatgttcc gctcacg                                        27

<210> SEQ ID NO 41
<211> LENGTH: 447
<212> TYPE: PRT
<213> ORGANISM: Mus musculus

<400> SEQUENCE: 41

Gln Val Thr Leu Lys Asp Ser Gly Pro Gly Ile Leu Gln Pro Ser Gln
1               5                   10                  15

Thr Leu Ser Leu Thr Cys Ser Phe Ser Gly Phe Ser Leu Ser Thr Ser
            20                  25                  30

Gly Met Gly Val Ser Trp Ile Arg Gln Pro Ser Gly Lys Gly Leu Glu
        35                  40                  45

Trp Leu Ala His Ile Tyr Trp Asp Asp Lys Arg Tyr Asn Pro Ser
    50                  55                  60

Leu Lys Ser Arg Leu Thr Ile Ser Lys Asp Thr Ser Ser Asn Gln Val
65                  70                  75                  80

Phe Leu Lys Ile Thr Ser Val Asp Thr Ala Asp Ser Ala Thr Tyr Tyr
                85                  90                  95

Cys Ser Thr Met Ile Thr Gly Phe Val Tyr Trp Gly Gln Gly Thr Leu
            100                 105                 110

Val Thr Val Ser Ala Ala Lys Thr Thr Ala Pro Ser Val Tyr Pro Leu
        115                 120                 125

Ala Pro Val Cys Gly Asp Thr Thr Gly Ser Ser Val Ala Leu Gly Cys
    130                 135                 140

Leu Val Lys Gly Tyr Phe Pro Glu Pro Val Thr Leu Thr Trp Asn Ser
145                 150                 155                 160

Gly Ser Leu Ser Ser Gly Val His Thr Phe Pro Ala Val Leu Gln Ser
                165                 170                 175

Asp Leu Tyr Thr Leu Ser Ser Ser Val Thr Val Thr Ser Ser Thr Trp
            180                 185                 190

```
Pro Ser Gln Ser Ile Thr Cys Asn Val Ala His Pro Ala Ser Ser Thr
        195                 200                 205
Lys Val Asp Lys Lys Ile Glu Pro Arg Gly Pro Thr Ile Lys Pro Cys
    210                 215                 220
Pro Pro Cys Lys Cys Pro Ala Pro Asn Leu Leu Gly Gly Pro Ser Val
225                 230                 235                 240
Phe Ile Phe Pro Pro Lys Ile Lys Asp Val Leu Met Ile Ser Leu Ser
                245                 250                 255
Pro Ile Val Thr Cys Val Val Val Asp Val Ser Glu Asp Asp Pro Asp
            260                 265                 270
Val Gln Ile Ser Trp Phe Val Asn Asn Val Glu Val His Thr Ala Gln
        275                 280                 285
Thr Gln Thr His Arg Glu Asp Tyr Asn Ser Thr Leu Arg Val Val Ser
    290                 295                 300
Ala Leu Pro Ile Gln His Gln Asp Trp Met Ser Gly Lys Glu Phe Lys
305                 310                 315                 320
Cys Lys Val Asn Asn Lys Asp Leu Pro Ala Pro Ile Glu Arg Thr Ile
                325                 330                 335
Ser Lys Pro Lys Gly Ser Val Arg Ala Pro Gln Val Tyr Val Leu Pro
            340                 345                 350
Pro Pro Glu Glu Glu Met Thr Lys Lys Gln Val Thr Leu Thr Cys Met
        355                 360                 365
Val Thr Asp Phe Met Pro Glu Asp Ile Tyr Val Glu Trp Thr Asn Asn
    370                 375                 380
Gly Lys Thr Glu Leu Asn Tyr Lys Asn Thr Glu Pro Val Leu Asp Ser
385                 390                 395                 400
Asp Gly Ser Tyr Phe Met Tyr Ser Lys Leu Arg Val Glu Lys Lys Asn
                405                 410                 415
Trp Val Glu Arg Asn Ser Tyr Ser Cys Ser Val Val His Glu Gly Leu
            420                 425                 430
His Asn His His Thr Thr Lys Ser Phe Ser Arg Thr Pro Gly Lys
        435                 440                 445

<210> SEQ ID NO 42
<211> LENGTH: 1344
<212> TYPE: DNA
<213> ORGANISM: Mus musculus

<400> SEQUENCE: 42
caggttactc tgaaagactc tggccctggg atattgcagc cctcccagac cctcagtctg     60
acttgttctt tctctgggtt ttcactgagc acttctggta tgggtgtgag ctggattcgt    120
cagccttcag aaagggtct ggagtggctg gcacacattt actgggatga tgacaagcgc    180
tataacccat ccctgaagag ccggctcaca atctccaagg atacctccag caaccaggta    240
ttcctcaaga tcaccagtgt ggacactgca gattctgcca catactactg ttccactatg    300
attacggggt tgtttactg gggccaaggg actctggtca ctgtctctgc agccaaaaca    360
acagccccat cggtctatcc cctggcccct gtgtgtggag atacaactgg ctcctcggtg    420
gctctaggat gcctggtcaa gggttatttc cctgagccag tgaccttgac ctggaactct    480
ggatccctgt ccagtggtgt gcacaccttc ccagctgtcc tgcagtctga cctctacacc    540
ctcagcagct cagtgactgt aacctcgagc acctggccca gccagtccat cacctgcaat    600
gtggcccacc cggcaagcag caccaaggtg gacaagaaaa ttgagcccag agggcccaca    660
atcaagccct gtcctccatg caaatgccca gcacctaacc tcttgggtgg accatccgtc    720
```

-continued

```
ttcatcttcc ctccaaagat caaggatgta ctcatgatct ccctgagccc catagtcaca    780
tgtgtggtgg tggatgtgag cgaggatgac ccagatgtcc agatcagctg gtttgtgaac    840
aacgtggaag tacacacagc tcagacacaa acccatagag aggattacaa cagtactctc    900
cgggtggtca gtgccctccc catccagcac caggactgga tgagtggcaa ggagttcaaa    960
tgcaaggtca acaacaaaga cctcccagcg cccatcgaga gaaccatctc aaaacccaaa   1020
gggtcagtaa gagctccaca ggtatatgtc ttgcctccac cagaagaaga gatgactaag   1080
aaacaggtca ctctgacctg catggtcaca gacttcatgc ctgaagacat ttacgtggag   1140
tggaccaaca cgggaaaaac agagctaaac tacaagaaca ctgaaccagt cctggactct   1200
gatggttctt acttcatgta cagcaagctg agagtggaaa agaagaactg ggtggaaaga   1260
aatagctact cctgttcagt ggtccacgag ggtctgcaca atcaccacac gactaagagc   1320
ttctcccgga ctccgggtaa atga                                          1344
```

<210> SEQ ID NO 43
<211> LENGTH: 219
<212> TYPE: PRT
<213> ORGANISM: Mus musculus

<400> SEQUENCE: 43

```
Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Ser Ile Val His Ser
            20                  25                  30

Asn Gly Asn Thr Tyr Leu Glu Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Val Pro Leu Thr Phe Gly Ala Gly Thr Lys Leu Glu Leu Lys
            100                 105                 110

Arg Ala Asp Ala Ala Pro Thr Val Ser Ile Phe Pro Pro Ser Ser Glu
        115                 120                 125

Gln Leu Thr Ser Gly Gly Ala Ser Val Val Cys Phe Leu Asn Asn Phe
    130                 135                 140

Tyr Pro Lys Asp Ile Asn Val Lys Trp Lys Ile Asp Gly Ser Glu Arg
145                 150                 155                 160

Gln Asn Gly Val Leu Asn Ser Trp Thr Asp Gln Asp Ser Lys Asp Ser
                165                 170                 175

Thr Tyr Ser Met Ser Ser Thr Leu Thr Leu Thr Lys Asp Glu Tyr Glu
            180                 185                 190

Arg His Asn Ser Tyr Thr Cys Glu Ala Thr His Lys Thr Ser Thr Ser
        195                 200                 205

Pro Ile Val Lys Ser Phe Asn Arg Asn Glu Cys
    210                 215
```

<210> SEQ ID NO 44
<211> LENGTH: 660
<212> TYPE: DNA
<213> ORGANISM: Mus musculus

<400> SEQUENCE: 44

```
gatgttttga tgacccaaac tccactctcc ctgcctgtca gtcttggaga tcaagcctcc      60
atctcttgca gatctagtca gagcattgta catagtaatg gaaacaccta tttagaatgg     120
tacctgcaga aaccaggcca gtctccaaag ctcctgatct acaaagtttc caaccgattt     180
tctggggtcc cagacaggtt cagtggcagt ggatcaggga cagatttcac actcaagatc     240
agtagagtgg aggctgagga tctgggagtt tattactgct ttcaaggttc acatgttccg     300
ctcacgttcg gtgctgggac caagctggag ctgaaacggg ctgatgctgc accaactgta     360
tccatcttcc caccatccag tgagcagtta acatctggag gtgcctcagt cgtgtgcttc     420
ttgaacaact ctacccccaa agacatcaat gtcaagtgga agattgatgg cagtgaacga     480
caaaatggcg tcctgaacag ttggactgat caggacagca agacagcac ctacagcatg     540 agcagtaccc tcacgttgac caaggacgag tatgaacgac ataacagcta cctgtgag      600 gccactcaca agacatcaac ttcacccatt gtcaagagct caacaggaa tgagtgttag     660
```

<210> SEQ ID NO 45
<211> LENGTH: 117
<212> TYPE: PRT
<213> ORGANISM: Mus musculus

<400> SEQUENCE: 45

```
Gln Val Thr Leu Lys Asp Ser Gly Pro Gly Ile Leu Gln Pro Ser Gln
1               5                   10                  15

Thr Leu Ser Leu Thr Cys Ser Phe Ser Gly Phe Ser Leu Ser Thr Ser
            20                  25                  30

Gly Met Gly Val Ser Trp Ile Arg Gln Pro Ser Gly Lys Gly Leu Glu
        35                  40                  45

Trp Leu Ala His Ile Tyr Trp Asp Asp Asp Lys Arg Tyr Asn Pro Ser
    50                  55                  60

Leu Lys Ser Arg Leu Thr Ile Ser Lys Asp Thr Ser Ser Asn Gln Val
65                  70                  75                  80

Phe Leu Lys Ile Thr Ser Val Asp Thr Ala Asp Ser Ala Thr Tyr Tyr
                85                  90                  95

Cys Ser Thr Met Ile Thr Gly Phe Val Tyr Trp Gly Gln Gly Thr Leu
            100                 105                 110

Val Thr Val Ser Ala
        115
```

<210> SEQ ID NO 46
<211> LENGTH: 351
<212> TYPE: DNA
<213> ORGANISM: Mus musculus

<400> SEQUENCE: 46

```
caggttactc tgaaagactc tggccctggg atattgcagc cctcccagac cctcagtctg      60
acttgttctt tctctgggtt ttcactgagc acttctggta tgggtgtgag ctggattcgt     120
cagccttcag gaaagggtct ggagtggctg gcacacattt actgggatga tgacaagcgc     180
tataacccat ccctgaagag ccggctcaca atctccaagg atacctccag caaccaggta     240
ttcctcaaga tcaccagtgt ggacactgca gattctgcca catactactg ttccactatg     300
attacggggt tgtttactg gggccaaggg actctggtca ctgtctctgc a               351
```

<210> SEQ ID NO 47
<211> LENGTH: 112
<212> TYPE: PRT
<213> ORGANISM: Mus musculus

<400> SEQUENCE: 47

Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Ser Ile Val His Ser
            20                  25                  30

Asn Gly Asn Thr Tyr Leu Glu Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Val Pro Leu Thr Phe Gly Ala Gly Thr Lys Leu Glu Leu Lys
            100                 105                 110

<210> SEQ ID NO 48
<211> LENGTH: 336
<212> TYPE: DNA
<213> ORGANISM: Mus musculus

<400> SEQUENCE: 48
gatgttttga tgacccaaac tccactctcc ctgcctgtca gtcttggaga tcaagcctcc     60
atctcttgca gatctagtca gagcattgta catagtaatg gaaacaccta tttagaatgg    120
tacctgcaga aaccaggcca gtctccaaag ctcctgatct acaaagtttc caaccgattt    180
tctggggtcc cagacaggtt cagtggcagt ggatcaggga cagatttcac actcaagatc    240
agtagagtgg aggctgagga tctgggagtt tattactgct ttcaaggttc acatgttccg    300
ctcacgttcg gtgctgggac caagctggag ctgaaa                              336

<210> SEQ ID NO 49
<211> LENGTH: 7
<212> TYPE: PRT
<213> ORGANISM: Mus musculus

<400> SEQUENCE: 49

Thr Ser Gly Met Gly Val Ser
1               5

<210> SEQ ID NO 50
<211> LENGTH: 21
<212> TYPE: DNA
<213> ORGANISM: Mus musculus

<400> SEQUENCE: 50
acttctggta tgggtgtgag c                                               21

<210> SEQ ID NO 51
<211> LENGTH: 9
<212> TYPE: PRT
<213> ORGANISM: Mus musculus

<400> SEQUENCE: 51

His Ile Tyr Trp Asp Asp Asp Lys Arg
1               5

<210> SEQ ID NO 52
<211> LENGTH: 27
<212> TYPE: DNA
<213> ORGANISM: Mus musculus

<400> SEQUENCE: 52
cacatttact gggatgatga caagcgc    27

<210> SEQ ID NO 53
<211> LENGTH: 7
<212> TYPE: PRT
<213> ORGANISM: Mus musculus

<400> SEQUENCE: 53

Met Ile Thr Gly Phe Val Tyr
1               5

<210> SEQ ID NO 54
<211> LENGTH: 21
<212> TYPE: DNA
<213> ORGANISM: Mus musculus

<400> SEQUENCE: 54
atgattacgg ggtttgttta c    21

<210> SEQ ID NO 55
<211> LENGTH: 16
<212> TYPE: PRT
<213> ORGANISM: Mus musculus

<400> SEQUENCE: 55

Arg Ser Ser Gln Ser Ile Val His Ser Asn Gly Asn Thr Tyr Leu Glu
1               5                   10                  15

<210> SEQ ID NO 56
<211> LENGTH: 48
<212> TYPE: DNA
<213> ORGANISM: Mus musculus

<400> SEQUENCE: 56
agatctagtc agagcattgt acatagtaat ggaaacacct atttagaa    48

<210> SEQ ID NO 57
<211> LENGTH: 7
<212> TYPE: PRT
<213> ORGANISM: Mus musculus

<400> SEQUENCE: 57

Lys Val Ser Asn Arg Phe Ser
1               5

<210> SEQ ID NO 58
<211> LENGTH: 21
<212> TYPE: DNA
<213> ORGANISM: Mus musculus

<400> SEQUENCE: 58
aaagtttcca accgattttc t    21

<210> SEQ ID NO 59
<211> LENGTH: 9
<212> TYPE: PRT
<213> ORGANISM: Mus musculus

<400> SEQUENCE: 59

Phe Gln Gly Ser His Val Pro Leu Thr
1               5

-continued

```
<210> SEQ ID NO 60
<211> LENGTH: 27
<212> TYPE: DNA
<213> ORGANISM: Mus musculus

<400> SEQUENCE: 60
tttcaaggtt cacatgttcc gctcacg                                             27

<210> SEQ ID NO 61
<211> LENGTH: 445
<212> TYPE: PRT
<213> ORGANISM: Mus musculus

<400> SEQUENCE: 61
```

Asp Val Gln Leu Val Glu Ser Gly Gly Gly Leu Val Gln Pro Gly Gly
1               5                   10                  15

Ser Arg Lys Leu Ser Cys Ala Ala Ser Gly Phe Thr Phe Ser Ser Phe
                20                  25                  30

Gly Met His Trp Val Arg Gln Ala Pro Glu Lys Gly Leu Glu Trp Val
            35                  40                  45

Ala Tyr Ile Ser Ser Gly Ser Ser Thr Ile Tyr Tyr Ala Asp Thr Val
        50                  55                  60

Lys Gly Arg Phe Thr Ile Ser Arg Asp Asn Pro Lys Asn Thr Leu Phe
65                  70                  75                  80

Leu Gln Met Thr Ser Leu Arg Ser Glu Asp Thr Ala Met Tyr Tyr Cys
                85                  90                  95

Ala Gly Thr Gly Thr Arg Ala Tyr Trp Gly Gln Gly Thr Leu Val Thr
            100                 105                 110

Val Ser Ala Ala Lys Thr Thr Ala Pro Ser Val Tyr Pro Leu Ala Pro
        115                 120                 125

Val Cys Gly Asp Thr Thr Gly Ser Ser Val Ala Leu Gly Cys Leu Val
    130                 135                 140

Lys Gly Tyr Phe Pro Glu Pro Val Thr Leu Thr Trp Asn Ser Gly Ser
145                 150                 155                 160

Leu Ser Ser Gly Val His Thr Phe Pro Ala Val Leu Gln Ser Asp Leu
                165                 170                 175

Tyr Thr Leu Ser Ser Ser Val Thr Val Thr Ser Ser Thr Trp Pro Ser
            180                 185                 190

Gln Ser Ile Thr Cys Asn Val Ala His Pro Ala Ser Ser Thr Lys Val
        195                 200                 205

Asp Lys Lys Ile Glu Pro Arg Gly Pro Thr Ile Lys Pro Cys Pro Pro
    210                 215                 220

Cys Lys Cys Pro Ala Pro Asn Leu Leu Gly Gly Pro Ser Val Phe Ile
225                 230                 235                 240

Phe Pro Pro Lys Ile Lys Asp Val Leu Met Ile Ser Leu Ser Pro Ile
                245                 250                 255

Val Thr Cys Val Val Asp Val Ser Glu Asp Pro Asp Val Gln
            260                 265                 270

Ile Ser Trp Phe Val Asn Asn Val Glu Val His Thr Ala Gln Thr Gln
        275                 280                 285

Thr His Arg Glu Asp Tyr Asn Ser Thr Leu Arg Val Val Ser Ala Leu
    290                 295                 300

Pro Ile Gln His Gln Asp Trp Met Ser Gly Lys Glu Phe Lys Cys Lys
305                 310                 315                 320

Val Asn Asn Lys Asp Leu Pro Ala Pro Ile Glu Arg Thr Ile Ser Lys
                325                 330                 335

```
Pro Lys Gly Ser Val Arg Ala Pro Gln Val Tyr Val Leu Pro Pro Pro
            340                 345                 350

Glu Glu Glu Met Thr Lys Lys Gln Val Thr Leu Thr Cys Met Val Thr
            355                 360                 365

Asp Phe Met Pro Glu Asp Ile Tyr Val Glu Trp Thr Asn Asn Gly Lys
        370                 375                 380

Thr Glu Leu Asn Tyr Lys Asn Thr Glu Pro Val Leu Asp Ser Asp Gly
385                 390                 395                 400

Ser Tyr Phe Met Tyr Ser Lys Leu Arg Val Glu Lys Lys Asn Trp Val
                405                 410                 415

Glu Arg Asn Ser Tyr Ser Cys Ser Val Val His Glu Gly Leu His Asn
            420                 425                 430

His His Thr Thr Lys Ser Phe Ser Arg Thr Pro Gly Lys
            435                 440                 445

<210> SEQ ID NO 62
<211> LENGTH: 1338
<212> TYPE: DNA
<213> ORGANISM: Mus musculus

<400> SEQUENCE: 62
gatgtgcagc tggtggagtc tgggggaggc ttagtgcagc ctggagggtc cggaaactc      60
tcctgtgcag cctctggatt cactttcagt agctttggaa tgcactgggt cgtcaggct     120
ccagagaagg ggctggagtg ggtcgcatac attagtagtg gcagtagtac catctactat    180
gcagacacag tgaagggccg attcaccatc tccagagaca tcccaagaa caccctgttc     240
ctgcaaatga ccagtctaag gtctgaggac acggccatgt attactgtgc cgggactggg    300
acgagagctt actggggcca agggactctg gtcactgtct ctgcagccaa acaacagcc     360
ccatcggtct atcccctggc cctgtgtgt ggagatacaa ctggctcctc ggtggctcta    420
ggatgcctgg tcaagggtta tttccctgag ccagtgacct tgacctggaa ctctggatcc    480
ctgtccagtg gtgtgcacac cttcccagct gtcctgcagt ctgacctcta cacctcagc     540
agctcagtga ctgtaacctc gagcacctgg cccagccagt ccatcacctg caatgtggcc    600
cacccggcaa gcagcaccaa ggtggacaag aaaattgagc ccagagggcc acaatcaag     660
ccctgtcctc catgcaaatg cccagcacct aacctcttgg gtggaccatc cgtcttcatc    720
ttccctccaa agatcaagga tgtactcatg atctccctga gccccatagt cacatgtgtg    780
gtggtggatg tgagcgagga tgacccagat gtccagatca gctggtttgt gaacaacgtg    840
gaagtacaca cagctcagac acaaacccat agagaggatt acaacagtac tctccgggtg    900
gtcagtgccc tccccatcca gcaccaggac tggatgagtg gcaaggagtt caaatgcaag    960
gtcaacaaca agacctcccc agcgcccatc gagagaacca tctcaaaacc caagggtca    1020
gtaagagctc cacaggtata tgtcttgcct ccaccagaag aagagatgac taagaaacag   1080
gtcactctga cctgcatggt cacagacttc atgcctgaag catttacgt ggagtggacc    1140
aacaacggga aaacagagct aaactacaag aacactgaac cagtcctgga ctctgatggt    1200
tcttacttca tgtacagcaa gctgagagtg gaaaagaaga ctgggtgga agaaatagc     1260
tactcctgtt cagtggtcca cgagggtctg cacaatcacc acacgactaa gagcttctcc    1320
cggactccgg gtaaatga                                                  1338

<210> SEQ ID NO 63
<211> LENGTH: 219
<212> TYPE: PRT
<213> ORGANISM: Mus musculus
```

<400> SEQUENCE: 63

| | | | | | | | | | | | | | | | |
|---|---|---|---|---|---|---|---|---|---|---|---|---|---|---|---|
|Asp|Val|Leu|Met|Thr|Gln|Thr|Pro|Leu|Ser|Leu|Pro|Val|Ser|Leu|Gly|
|1| | | |5| | | | |10| | | | |15| |

Asp Gln Ala Ser Ile Ser Cys Arg Ser Ser Gln Ser Ile Val His Ser
                20                  25                  30

Asn Gly Asn Thr Tyr Leu Glu Trp Tyr Leu Gln Lys Pro Gly Gln Ser
            35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Val Pro Pro Thr Phe Gly Gly Gly Thr Lys Leu Glu Ile Lys
                100                 105                 110

Arg Ala Asp Ala Ala Pro Thr Val Ser Ile Phe Pro Pro Ser Ser Glu
            115                 120                 125

Gln Leu Thr Ser Gly Gly Ala Ser Val Val Cys Phe Leu Asn Asn Phe
130                 135                 140

Tyr Pro Lys Asp Ile Asn Val Lys Trp Lys Ile Asp Gly Ser Glu Arg
145                 150                 155                 160

Gln Asn Gly Val Leu Asn Ser Trp Thr Asp Gln Asp Ser Lys Asp Ser
                165                 170                 175

Thr Tyr Ser Met Ser Ser Thr Leu Thr Leu Thr Lys Asp Glu Tyr Glu
            180                 185                 190

Arg His Asn Ser Tyr Thr Cys Glu Ala Thr His Lys Thr Ser Thr Ser
        195                 200                 205

Pro Ile Val Lys Ser Phe Asn Arg Asn Glu Cys
    210                 215

<210> SEQ ID NO 64
<211> LENGTH: 660
<212> TYPE: DNA
<213> ORGANISM: Mus musculus

<400> SEQUENCE: 64

```
gatgttttga tgacccaaac tccactctcc ctgcctgtca gtcttggaga tcaagcctcc        60
atctcttgca gatctagtca gagcattgta catagtaatg aaacaccta  tttagaatgg       120
tacctgcaga aaccaggcca gtctcctaag ctcctgatct acaaagtttc caaccgattt       180
tctggggtcc cagacaggtt cagtggcagt ggatcaggga cagatttcac actcaagatc       240
agcagagtgg aggctgagga tctgggagtt tattactgct ttcaaggttc acatgttcct       300
ccgacgttcg gtggaggcac caagctggaa atcaaacggg ctgatgctgc accaactgta       360
tccatcttcc caccatccag tgagcagtta acatctggag gtgcctcagt cgtgtgcttc       420
ttgaacaact ctaccccaa  agacatcaat gtcaagtgga agattgatgg cagtgaacga       480
caaaatggcg tcctgaacag ttggactgat caggacagca agacagcac  ctacagcatg       540
agcagtaccc tcacgttgac caaggacgag tatgaacgac ataacagcta cctgtgcgag       600
gccactcaca gacatcaac  ttcacccatt gtcaagagct tcaacaggaa tgagtgttag       660
```

<210> SEQ ID NO 65
<211> LENGTH: 115
<212> TYPE: PRT
<213> ORGANISM: Mus musculus

<400> SEQUENCE: 65

Asp Val Gln Leu Val Glu Ser Gly Gly Gly Leu Val Gln Pro Gly Gly
1               5                   10                  15

Ser Arg Lys Leu Ser Cys Ala Ala Ser Gly Phe Thr Phe Ser Ser Phe
            20                  25                  30

Gly Met His Trp Val Arg Gln Ala Pro Glu Lys Gly Leu Glu Trp Val
        35                  40                  45

Ala Tyr Ile Ser Ser Gly Ser Ser Thr Ile Tyr Tyr Ala Asp Thr Val
    50                  55                  60

Lys Gly Arg Phe Thr Ile Ser Arg Asp Asn Pro Lys Asn Thr Leu Phe
65                  70                  75                  80

Leu Gln Met Thr Ser Leu Arg Ser Glu Asp Thr Ala Met Tyr Tyr Cys
                85                  90                  95

Ala Gly Thr Gly Thr Arg Ala Tyr Trp Gly Gln Gly Thr Leu Val Thr
            100                 105                 110

Val Ser Ala
        115

<210> SEQ ID NO 66
<211> LENGTH: 345
<212> TYPE: DNA
<213> ORGANISM: Mus musculus

<400> SEQUENCE: 66
gatgtgcagc tggtggagtc tgggggaggc ttagtgcagc ctggagggtc ccggaaactc      60
tcctgtgcag cctctggatt cactttcagt agctttggaa tgcactgggt tcgtcaggct    120
ccagagaagg ggctggagtg ggtcgcatac attagtagtg gcagtagtac catctactat    180
gcagacacag tgaagggccg attcaccatc tccagagaca atcccaagaa caccctgttc    240
ctgcaaatga ccagtctaag gtctgaggac acggccatgt attactgtgc cgggactggg    300
acgagagctt actggggcca aggactctg gtcactgtct ctgca                     345

<210> SEQ ID NO 67
<211> LENGTH: 112
<212> TYPE: PRT
<213> ORGANISM: Mus musculus

<400> SEQUENCE: 67

Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Ser Ile Val His Ser
            20                  25                  30

Asn Gly Asn Thr Tyr Leu Glu Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Val Pro Pro Thr Phe Gly Gly Gly Thr Lys Leu Glu Ile Lys
            100                 105                 110

<210> SEQ ID NO 68
<211> LENGTH: 336
<212> TYPE: DNA

<210> SEQ ID NO 68
<211> LENGTH: 336
<212> TYPE: DNA
<213> ORGANISM: Mus musculus

<400> SEQUENCE: 68
gatgttttga tgacccaaac tccactctcc ctgcctgtca gtcttggaga tcaagcctcc    60
atctcttgca gatctagtca gagcattgta catagtaatg gaaacaccta tttagaatgg   120
tacctgcaga aaccaggcca gtctcctaag ctcctgatct acaaagtttc caaccgattt   180
tctggggtcc cagacaggtt cagtggcagt ggatcaggga cagatttcac actcaagatc   240
agcagagtgg aggctgagga tctgggagtt tattactgct ttcaaggttc acatgttcct   300
ccgacgttcg gtggaggcac caagctggaa atcaaa                             336

<210> SEQ ID NO 69
<211> LENGTH: 5
<212> TYPE: PRT
<213> ORGANISM: Mus musculus

<400> SEQUENCE: 69

Ser Phe Gly Met His
1               5

<210> SEQ ID NO 70
<211> LENGTH: 15
<212> TYPE: DNA
<213> ORGANISM: Mus musculus

<400> SEQUENCE: 70
agctttggaa tgcac                                                     15

<210> SEQ ID NO 71
<211> LENGTH: 10
<212> TYPE: PRT
<213> ORGANISM: Mus musculus

<400> SEQUENCE: 71

Tyr Ile Ser Ser Gly Ser Ser Thr Ile Tyr
1               5                   10

<210> SEQ ID NO 72
<211> LENGTH: 30
<212> TYPE: DNA
<213> ORGANISM: Mus musculus

<400> SEQUENCE: 72
tacattagta gtggcagtag taccatctac                                     30

<210> SEQ ID NO 73
<211> LENGTH: 6
<212> TYPE: PRT
<213> ORGANISM: Mus musculus

<400> SEQUENCE: 73

Thr Gly Thr Arg Ala Tyr
1               5

<210> SEQ ID NO 74
<211> LENGTH: 18
<212> TYPE: DNA
<213> ORGANISM: Mus musculus

<400> SEQUENCE: 74
actgggacga gagcttac                                                  18

<210> SEQ ID NO 75
<211> LENGTH: 16
<212> TYPE: PRT
<213> ORGANISM: Mus musculus

<400> SEQUENCE: 75

Arg Ser Ser Gln Ser Ile Val His Ser Asn Gly Asn Thr Tyr Leu Glu
1               5                   10                  15

<210> SEQ ID NO 76
<211> LENGTH: 48
<212> TYPE: DNA
<213> ORGANISM: Mus musculus

<400> SEQUENCE: 76
agatctagtc agagcattgt acatagtaat ggaaacacct atttagaa              48

<210> SEQ ID NO 77
<211> LENGTH: 7
<212> TYPE: PRT
<213> ORGANISM: Mus musculus

<400> SEQUENCE: 77

Lys Val Ser Asn Arg Phe Ser
1               5

<210> SEQ ID NO 78
<211> LENGTH: 21
<212> TYPE: DNA
<213> ORGANISM: Mus musculus

<400> SEQUENCE: 78
aaagtttcca accgattttc t                                           21

<210> SEQ ID NO 79
<211> LENGTH: 9
<212> TYPE: PRT
<213> ORGANISM: Mus musculus

<400> SEQUENCE: 79

Phe Gln Gly Ser His Val Pro Pro Thr
1               5

<210> SEQ ID NO 80
<211> LENGTH: 27
<212> TYPE: DNA
<213> ORGANISM: Mus musculus

<400> SEQUENCE: 80
tttcaaggtt cacatgttcc tccgacg                                     27

<210> SEQ ID NO 81
<211> LENGTH: 442
<212> TYPE: PRT
<213> ORGANISM: Mus musculus

<400> SEQUENCE: 81

Gln Val Gln Leu Gln Gln Pro Gly Ala Glu Leu Val Lys Pro Gly Ala
1               5                   10                  15

Ser Val Lys Leu Ser Cys Lys Ala Ser Gly Tyr Thr Phe Thr Ser Tyr
            20                  25                  30

Trp Met His Trp Val Lys Leu Arg Pro Gly Gln Gly Phe Glu Trp Ile
        35                  40                  45

Gly Glu Ile Asn Pro Arg Asn Gly Gly Thr Asn Asn Glu Asn Phe

```
                50                  55                  60
Lys Arg Lys Ala Thr Leu Thr Val Asp Lys Ser Ser Thr Ala Tyr
 65                  70                  75                  80

Met Gln Leu Ser Ser Leu Thr Ser Glu Asp Ser Ala Val Tyr Tyr Cys
                 85                  90                  95

Thr Arg Asp Gly Asn Tyr Asp Pro Phe Ala Tyr Trp Gly Gln Gly Thr
                100                 105                 110

Leu Val Thr Val Ser Ala Ala Lys Thr Thr Pro Pro Ser Val Tyr Pro
                115                 120                 125

Leu Ala Pro Gly Ser Ala Ala Gln Thr Asn Ser Met Val Thr Leu Gly
            130                 135                 140

Cys Leu Val Lys Gly Tyr Phe Pro Glu Pro Val Thr Val Thr Trp Asn
145                 150                 155                 160

Ser Gly Ser Leu Ser Ser Gly Val His Thr Phe Pro Ala Val Leu Gln
                165                 170                 175

Ser Asp Leu Tyr Thr Leu Ser Ser Ser Val Thr Val Pro Ser Ser Thr
            180                 185                 190

Trp Pro Ser Glu Thr Val Thr Cys Asn Val Ala His Pro Ala Ser Ser
        195                 200                 205

Thr Lys Val Asp Lys Lys Ile Val Pro Arg Asp Cys Gly Cys Lys Pro
210                 215                 220

Cys Ile Cys Thr Val Pro Glu Val Ser Ser Val Phe Ile Phe Pro Pro
225                 230                 235                 240

Lys Pro Lys Asp Val Leu Thr Ile Thr Leu Thr Pro Lys Val Thr Cys
                245                 250                 255

Val Val Val Asp Ile Ser Lys Asp Asp Pro Glu Val Gln Phe Ser Trp
            260                 265                 270

Phe Val Asp Asp Val Glu Val His Thr Ala Gln Thr Gln Pro Arg Glu
        275                 280                 285

Glu Gln Phe Asn Ser Thr Phe Arg Ser Val Ser Glu Leu Pro Ile Met
290                 295                 300

His Gln Asp Trp Leu Asn Gly Lys Glu Phe Lys Cys Arg Val Asn Ser
305                 310                 315                 320

Ala Ala Phe Pro Ala Pro Ile Glu Lys Thr Ile Ser Lys Thr Lys Gly
                325                 330                 335

Arg Pro Lys Ala Pro Gln Val Tyr Thr Ile Pro Pro Pro Lys Glu Gln
            340                 345                 350

Met Ala Lys Asp Lys Val Ser Leu Thr Cys Met Ile Thr Asp Phe Phe
        355                 360                 365

Pro Glu Asp Ile Thr Val Glu Trp Gln Trp Asn Gly Gln Pro Ala Glu
370                 375                 380

Asn Tyr Lys Asn Thr Gln Pro Ile Met Asp Thr Asp Gly Ser Tyr Phe
385                 390                 395                 400

Val Tyr Ser Lys Leu Asn Val Gln Lys Ser Asn Trp Glu Ala Gly Asn
                405                 410                 415

Thr Phe Thr Cys Ser Val Leu His Glu Gly Leu Leu Asn Leu His Thr
            420                 425                 430

Glu Lys Ser Leu Ser Leu Ser Pro Gly Lys
        435                 440

<210> SEQ ID NO 82
<211> LENGTH: 1329
<212> TYPE: DNA
<213> ORGANISM: Mus musculus
```

<400> SEQUENCE: 82

```
caggtccaac tccagcagcc tggggctgaa ctggtgaagc tggggcttc  agtgaagttg      60
tcctgcaagg cttctggcta caccttcacc agctactgga tgcactgggt gaagctgagg     120
cctggacaag gctttgagtg gattggagag attaatccta gaaatggtgg tactaacaac     180
aatgagaact tcaagagaaa ggccacactg actgtagaca atcctccag  cacagcctac     240
atgcaactca gcagcctgac atctgaggac tctgcggtct attactgtac aagagatggt     300
aactacgacc cctttgctta ctggggccaa gggactctgg tcactgtctc tgcagccaaa     360
acgacacccc catctgtcta tccactggcc cctggatctg ctgcccaaac taactccatg     420
gtgaccctgg atgcctggt  caagggctat ttccctgagc cagtgacagt gacctggaac     480
tctggatccc tgtccagcgg tgtgcacacc ttcccagctg tcctgcagtc tgacctctac     540
actctgagca gctcagtgac tgtcccctcc agcacctggc ccagcgagac cgtcacctgc     600
aacgttgccc acccggccag cagcaccaag gtggacaaga aaattgtgcc cagggattgt     660
ggttgtaagc cttgcatatg tacagtccca gaagtatcat ctgtcttcat cttcccccca     720
aagcccaagg atgtgctcac cattactctg actcctaagg tcacgtgtgt tgtggtagac     780
atcagcaagg atgatcccga ggtccagttc agctggtttg tagatgatgt ggaggtgcac     840
acagctcaga cgcaacccg  ggaggagcag ttcaacagca cttccgctc  agtcagtgaa     900
cttcccatca tgcaccagga ctggctcaat ggcaaggagt tcaaatgcag ggtcaacagt     960
gcagctttcc ctgcccccat cgagaaaacc atctccaaaa ccaaaggcag accgaaggct    1020
ccacaggtgt acaccattcc acctcccaag gagcagatgg ccaaggataa agtcagtctg    1080
acctgcatga taacagactt cttccctgaa gacattactg tggagtggca gtggaatggg    1140
cagccagcgg agaactacaa gaacactcag cccatcatgg acacagatgg ctcttacttc    1200
gtttacagca agctcaatgt gcagaagagc aactgggagg caggaaatac tttcacctgc    1260
tctgtgttac atgagggcct gctcaacctc catactgaga agagcctctc cctctctcct    1320
ggtaaatga                                                            1329
```

<210> SEQ ID NO 83
<211> LENGTH: 220
<212> TYPE: PRT
<213> ORGANISM: Mus musculus

<400> SEQUENCE: 83

```
Asp Val Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Val His Ser
            20                  25                  30

Asn Gly Asn Thr Tyr Leu His Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Ser
                85                  90                  95

Thr His Val Pro Pro Tyr Thr Phe Gly Gly Gly Thr Lys Leu Glu Ile
            100                 105                 110

Lys Arg Ala Asp Ala Ala Pro Thr Val Ser Ile Phe Pro Pro Ser Ser
        115                 120                 125
```

```
Glu Gln Leu Thr Ser Gly Gly Ala Ser Val Val Cys Phe Leu Asn Asn
        130                 135                 140
Phe Tyr Pro Lys Asp Ile Asn Val Lys Trp Lys Ile Asp Gly Ser Glu
145                 150                 155                 160
Arg Gln Asn Gly Val Leu Asn Ser Trp Thr Asp Gln Asp Ser Lys Asp
                165                 170                 175
Ser Thr Tyr Ser Met Ser Ser Thr Leu Thr Leu Thr Lys Asp Glu Tyr
            180                 185                 190
Glu Arg His Asn Ser Tyr Thr Cys Glu Ala Thr His Lys Thr Ser Thr
        195                 200                 205
Ser Pro Ile Val Lys Ser Phe Asn Arg Asn Glu Cys
    210                 215                 220
```

```
<210> SEQ ID NO 84
<211> LENGTH: 663
<212> TYPE: DNA
<213> ORGANISM: Mus musculus

<400> SEQUENCE: 84
gatgttgtga tgacccaaac tccactctcc ctgcctgtca gtcttggaga tcaagcctcc     60
atctcttgca gatctagtca gagccttgta cacagtaatg gaaacaccta tttacattgg    120
tacctgcaga agccaggcca gtctccaaag ctcctgatct acaaagtttc caaccgattt    180
tctggggtcc cagacaggtt cagtggcagt ggatcaggga cagatttcac actcaagatc    240
agcagagtgg aggctgagga tctgggagtt tatttctgct ctcaaagtac acatgttcct    300
ccgtacacgt tcggaggggg gaccaagctg gaaataaaac gggctgatgc tgcaccaact    360
gtatccatct tcccaccatc cagtgagcag ttaacatctg gaggtgcctc agtcgtgtgc    420
ttcttgaaca acttctaccc caaagacatc aatgtcaagt ggaagattga tggcagtgaa    480
cgacaaaatg gcgtcctgaa cagttggact gatcaggaca gcaaagacag cacctacagc    540
atgagcagta ccctcacgtt gaccaaggac gagtatgaac gacataacag ctatacctgt    600
gaggccactc acaagacatc aacttcaccc attgtcaaga gcttcaacag gaatgagtgt    660
tag                                                                  663
```

```
<210> SEQ ID NO 85
<211> LENGTH: 118
<212> TYPE: PRT
<213> ORGANISM: Mus musculus

<400> SEQUENCE: 85

Gln Val Gln Leu Gln Gln Pro Gly Ala Glu Leu Val Lys Pro Gly Ala
1               5                   10                  15
Ser Val Lys Leu Ser Cys Lys Ala Ser Gly Tyr Thr Phe Thr Ser Tyr
            20                  25                  30
Trp Met His Trp Val Lys Leu Arg Pro Gly Gln Gly Phe Glu Trp Ile
        35                  40                  45
Gly Glu Ile Asn Pro Arg Asn Gly Gly Thr Asn Asn Glu Asn Phe
    50                  55                  60
Lys Arg Lys Ala Thr Leu Thr Val Asp Lys Ser Ser Ser Thr Ala Tyr
65                  70                  75                  80
Met Gln Leu Ser Ser Leu Thr Ser Glu Asp Ser Ala Val Tyr Tyr Cys
                85                  90                  95
Thr Arg Asp Gly Asn Tyr Asp Pro Phe Ala Tyr Trp Gly Gln Gly Thr
            100                 105                 110
Leu Val Thr Val Ser Ala
```

<210> SEQ ID NO 86
<211> LENGTH: 354
<212> TYPE: DNA
<213> ORGANISM: Mus musculus

<400> SEQUENCE: 86

```
caggtccaac tccagcagcc tggggctgaa ctggtgaagc ctggggcttc agtgaagttg    60
tcctgcaagg cttctggcta caccttcacc agctactgga tgcactgggt gaagctgagg   120
cctggacaag ctttgagtg gattggagag attaatccta gaaatggtgg tactaacaac   180
aatgagaact tcaagagaaa ggccacactg actgtagaca atcctccag cacagcctac    240
atgcaactca gcagcctgac atctgaggac tctgcggtct attactgtac aagagatggt   300
aactacgacc cctttgctta ctggggccaa gggactctgg tcactgtctc tgca           354
```

<210> SEQ ID NO 87
<211> LENGTH: 113
<212> TYPE: PRT
<213> ORGANISM: Mus musculus

<400> SEQUENCE: 87

Asp Val Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Val His Ser
            20                  25                  30

Asn Gly Asn Thr Tyr Leu His Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Ser
                85                  90                  95

Thr His Val Pro Pro Tyr Thr Phe Gly Gly Gly Thr Lys Leu Glu Ile
            100                 105                 110

Lys

<210> SEQ ID NO 88
<211> LENGTH: 339
<212> TYPE: DNA
<213> ORGANISM: Mus musculus

<400> SEQUENCE: 88

```
gatgttgtga tgacccaaac tccactctcc ctgcctgtca gtcttggaga tcaagcctcc    60
atctcttgca gatctagtca gagccttgta cacagtaatg gaaacaccta tttacattgg   120
tacctgcaga agccaggcca gtctccaaag ctcctgatct acaaagtttc caaccgattt   180
tctggggtcc cagacaggtt cagtggcagt ggatcaggga cagatttcac actcaagatc   240
agcagagtgg aggctgagga tctgggagtt tatttctgct ctcaaagtac acatgttcct   300
ccgtacacgt tcggagggggg gaccaagctg gaaataaaa                            339
```

<210> SEQ ID NO 89
<211> LENGTH: 5
<212> TYPE: PRT
<213> ORGANISM: Mus musculus

<400> SEQUENCE: 89

Ser Tyr Trp Met His
1               5

<210> SEQ ID NO 90
<211> LENGTH: 15
<212> TYPE: DNA
<213> ORGANISM: Mus musculus

<400> SEQUENCE: 90
agctactgga tgcac                                                      15

<210> SEQ ID NO 91
<211> LENGTH: 10
<212> TYPE: PRT
<213> ORGANISM: Mus musculus

<400> SEQUENCE: 91

Glu Ile Asn Pro Arg Asn Gly Gly Thr Asn
1               5                   10

<210> SEQ ID NO 92
<211> LENGTH: 30
<212> TYPE: DNA
<213> ORGANISM: Mus musculus

<400> SEQUENCE: 92
gagattaatc ctagaaatgg tggtactaac                                      30

<210> SEQ ID NO 93
<211> LENGTH: 9
<212> TYPE: PRT
<213> ORGANISM: Mus musculus

<400> SEQUENCE: 93

Asp Gly Asn Tyr Asp Pro Phe Ala Tyr
1               5

<210> SEQ ID NO 94
<211> LENGTH: 27
<212> TYPE: DNA
<213> ORGANISM: Mus musculus

<400> SEQUENCE: 94
gatggtaact acgaccccctt tgcttac                                        27

<210> SEQ ID NO 95
<211> LENGTH: 16
<212> TYPE: PRT
<213> ORGANISM: Mus musculus

<400> SEQUENCE: 95

Arg Ser Ser Gln Ser Leu Val His Ser Asn Gly Asn Thr Tyr Leu His
1               5                   10                  15

<210> SEQ ID NO 96
<211> LENGTH: 48
<212> TYPE: DNA
<213> ORGANISM: Mus musculus

<400> SEQUENCE: 96
agatctagtc agagccttgt acacagtaat ggaaacacct atttacat                  48

<210> SEQ ID NO 97
<211> LENGTH: 7

```
<212> TYPE: PRT
<213> ORGANISM: Mus musculus

<400> SEQUENCE: 97

Lys Val Ser Asn Arg Phe Ser
1               5

<210> SEQ ID NO 98
<211> LENGTH: 21
<212> TYPE: DNA
<213> ORGANISM: Mus musculus

<400> SEQUENCE: 98
aaagtttcca accgattttc t                                            21

<210> SEQ ID NO 99
<211> LENGTH: 10
<212> TYPE: PRT
<213> ORGANISM: Mus musculus

<400> SEQUENCE: 99

Ser Gln Ser Thr His Val Pro Pro Tyr Thr
1               5                   10

<210> SEQ ID NO 100
<211> LENGTH: 30
<212> TYPE: DNA
<213> ORGANISM: Mus musculus

<400> SEQUENCE: 100
tctcaaagta cacatgttcc tccgtacacg                                   30

<210> SEQ ID NO 101
<211> LENGTH: 453
<212> TYPE: PRT
<213> ORGANISM: Mus musculus

<400> SEQUENCE: 101

Gln Val Thr Leu Lys Glu Ser Gly Pro Gly Ile Leu Gln Pro Ser Gln
1               5                   10                  15

Thr Leu Ser Leu Thr Cys Ser Phe Ser Gly Phe Ser Leu Ser Thr Ser
            20                  25                  30

Gly Met Gly Val Ser Trp Ile Arg Gln Pro Ser Gly Glu Gly Leu Glu
        35                  40                  45

Trp Leu Ala His Ile Tyr Trp Asp Asp Lys Arg Tyr Asn Pro Ser
    50                  55                  60

Leu Lys Ser Arg Leu Thr Ile Ser Lys Asp Thr Ser Arg Asn Gln Val
65              70                  75                  80

Phe Leu Lys Ile Thr Ser Val Asp Thr Ala Asp Thr Ala Thr Tyr Tyr
                85                  90                  95

Cys Gly Arg Tyr Arg Tyr Gly Phe Ala Tyr Trp Gly Gln Gly Thr Leu
            100                 105                 110

Val Thr Val Ser Ala Ala Lys Thr Thr Pro Pro Ser Val Tyr Pro Leu
        115                 120                 125

Ala Pro Gly Cys Gly Asp Thr Thr Gly Ser Ser Val Thr Leu Gly Cys
    130                 135                 140

Leu Val Lys Gly Tyr Phe Pro Glu Ser Val Thr Val Thr Trp Asn Ser
145                 150                 155                 160

Gly Ser Leu Ser Ser Ser Val His Thr Phe Pro Ala Leu Leu Gln Ser
                165                 170                 175
```

```
Gly Leu Tyr Thr Met Ser Ser Val Thr Val Pro Ser Ser Thr Trp
            180                 185                 190
Pro Ser Gln Thr Val Thr Cys Ser Val Ala His Pro Ala Ser Ser Thr
            195                 200                 205
Thr Val Asp Lys Lys Leu Glu Pro Ser Gly Pro Ile Ser Thr Ile Asn
    210                 215                 220
Pro Cys Pro Pro Cys Lys Glu Cys His Lys Cys Pro Ala Pro Asn Leu
225                 230                 235                 240
Glu Gly Gly Pro Ser Val Phe Ile Phe Pro Pro Asn Ile Lys Asp Val
                245                 250                 255
Leu Met Ile Ser Leu Thr Pro Lys Val Thr Cys Val Val Val Asp Val
                260                 265                 270
Ser Glu Asp Asp Pro Asp Val Gln Ile Ser Trp Phe Val Asn Asn Val
            275                 280                 285
Glu Val His Thr Ala Gln Thr Gln Thr His Arg Glu Asp Tyr Asn Ser
        290                 295                 300
Thr Ile Arg Val Val Ser Thr Leu Pro Ile Gln His Gln Asp Trp Met
305                 310                 315                 320
Ser Gly Lys Glu Phe Lys Cys Lys Val Asn Asn Lys Asp Leu Pro Ser
                325                 330                 335
Pro Ile Glu Arg Thr Ile Ser Lys Ile Lys Gly Leu Val Arg Ala Pro
            340                 345                 350
Gln Val Tyr Ile Leu Pro Pro Ala Glu Gln Leu Ser Arg Lys Asp
        355                 360                 365
Val Ser Leu Thr Cys Leu Val Val Gly Phe Asn Pro Gly Asp Ile Ser
370                 375                 380
Val Glu Trp Thr Ser Asn Gly His Thr Glu Glu Asn Tyr Lys Asp Thr
385                 390                 395                 400
Ala Pro Val Leu Asp Ser Asp Gly Ser Tyr Phe Ile Tyr Ser Lys Leu
                405                 410                 415
Asn Met Lys Thr Ser Lys Trp Glu Lys Thr Asp Ser Phe Ser Cys Asn
            420                 425                 430
Val Arg His Glu Gly Leu Lys Asn Tyr Tyr Leu Lys Lys Thr Ile Ser
        435                 440                 445
Arg Ser Pro Gly Lys
    450

<210> SEQ ID NO 102
<211> LENGTH: 1362
<212> TYPE: DNA
<213> ORGANISM: Mus musculus

<400> SEQUENCE: 102
caggttactc tgaaagagtc tggccctggg atattgcagc cctcccagac cctcagtctg      60
acttgttctt tctctgggtt ttcactgagc acttctggta tgggtgtgag ctggattcgt     120
cagccttcag agagggtctg gagtggctg gcacacattt actgggatga tgacaagcgc     180
tataacccat ccctgaagag ccggctcaca atctccaagg atacctccag aaaccaggta     240
ttcctcaaga tcaccagtgt ggacactgca gatactgcca catactactg tgtcgatat     300
aggtacggct tgcttactg gggccaaggg actctggtca ctgtctctgc agccaaaaca     360
acaccccat cagtctatcc actggcccct gggtgtggag atacaactgg ttcctccgtg     420
actctgggat gcctggtcaa gggctacttc cctgagtcag tgactgtgac ttggaactct     480
ggatccctgt ccagcagtgt gcacaccttc ccagctctcc tgcagtctgg actctacact     540
```

```
atgagcagct cagtgactgt cccctccagc acctggccaa gtcagaccgt cacctgcagc    600
gttgctcacc cagccagcag caccacggtg gacaaaaaac ttgagcccag cgggcccatt    660
tcaacaatca acccctgtcc tccatgcaag gagtgtcaca aatgcccagc tcctaacctc    720
gagggtggac catccgtctt catcttccct ccaaatatca aggatgtact catgatctcc    780
ctgacaccca aggtcacgtg tgtggtggtg gatgtgagcg aggatgaccc agacgtccag    840
atcagctggt ttgtgaacaa cgtggaagta cacacagctc agacacaaac ccatagagag    900
gattacaaca gtactatccg ggtggtcagc accctcccca tccagcacca ggactggatg    960
agtggcaagg agttcaaatg caaggtcaac aacaaagacc tcccatcacc catcgagaga   1020
accatctcaa aaattaaagg gctagtcaga gctccacaag tatacatctt gccgccacca   1080
gcagagcagt tgtccaggaa agatgtcagt ctcacttgcc tggtcgtggg cttcaaccct   1140
ggagacatca gtgtggagtg gaccagcaat gggcatacag aggagaacta caaggacacc   1200
gcaccagtcc tggactctga cggttcttac ttcatatata gcaagctcaa tatgaaaaca   1260
agcaagtggg agaaaacaga ttccttctca tgcaacgtga gacacgaggg tctgaaaaat   1320
tactacctga agaagaccat ctcccggtct ccgggtaaat ga                      1362
```

<210> SEQ ID NO 103
<211> LENGTH: 219
<212> TYPE: PRT
<213> ORGANISM: Mus musculus

<400> SEQUENCE: 103

```
Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Ser Ile Val His Ser
            20                  25                  30

Asn Gly Asn Thr Tyr Leu Glu Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Val Pro Leu Thr Phe Gly Ala Gly Thr Lys Leu Glu Leu Lys
            100                 105                 110

Arg Ala Asp Ala Ala Pro Thr Val Ser Ile Phe Pro Pro Ser Ser Glu
        115                 120                 125

Gln Leu Thr Ser Gly Gly Ala Ser Val Val Cys Phe Leu Asn Asn Phe
    130                 135                 140

Tyr Pro Lys Asp Ile Asn Val Lys Trp Lys Ile Asp Gly Ser Glu Arg
145                 150                 155                 160

Gln Asn Gly Val Leu Asn Ser Trp Thr Asp Gln Asp Ser Lys Asp Ser
                165                 170                 175

Thr Tyr Ser Met Ser Ser Thr Leu Thr Leu Thr Lys Asp Glu Tyr Glu
            180                 185                 190

Arg His Asn Ser Tyr Thr Cys Glu Ala Thr His Lys Thr Ser Thr Ser
        195                 200                 205

Pro Ile Val Lys Ser Phe Asn Arg Asn Glu Cys
    210                 215
```

<210> SEQ ID NO 104

```
<211> LENGTH: 660
<212> TYPE: DNA
<213> ORGANISM: Mus musculus

<400> SEQUENCE: 104
gatgttttga tgacccaaac tccactctcc ctgcctgtca gtcttggaga tcaagcctcc      60
atctcttgca gatctagtca gagcattgta catagtaatg aaacaccta tttagaatgg     120 tacctgcaga aaccaggcca gtctccaaag ctcctgatct acaaagtttc caaccgattt     180
tctggggtcc cagacaggtt cagtggcagt ggatcaggga cagatttcac actcaagatc     240
agcagagtgg aggctgagga tctgggagtt tattactgct ttcaaggttc acatgttccg     300
ctcacgttcg gtgctgggac caagctggag ctgaaacggg ctgatgctgc accaactgta     360
tccatcttcc caccatccag tgagcagtta acatctggag gtgcctcagt cgtgtgcttc     420
ttgaacaact tctaccccaa agacatcaat gtcaagtgga agattgatgg cagtgaacga     480
caaaatggcg tcctgaacag ttggactgat caggacagca agacagcac ctacagcatg     540 agcagtaccc tcacgttgac caaggacgag tatgaacgac ataacagcta tacctgtgag     600
gccactcaca gacatcaac ttcacccatt gtcaagagct caacaggaa tgagtgttag     660

<210> SEQ ID NO 105
<211> LENGTH: 116
<212> TYPE: PRT
<213> ORGANISM: Mus musculus

<400> SEQUENCE: 105

Gln Val Thr Leu Lys Glu Ser Gly Pro Gly Ile Leu Gln Pro Ser Gln
  1               5                  10                  15

Thr Leu Ser Leu Thr Cys Ser Phe Ser Gly Phe Ser Leu Ser Thr Ser
             20                  25                  30

Gly Met Gly Val Ser Trp Ile Arg Gln Pro Ser Gly Glu Gly Leu Glu
         35                  40                  45

Trp Leu Ala His Ile Tyr Trp Asp Asp Asp Lys Arg Tyr Asn Pro Ser
     50                  55                  60

Leu Lys Ser Arg Leu Thr Ile Ser Lys Asp Thr Ser Arg Asn Gln Val
 65                  70                  75                  80

Phe Leu Lys Ile Thr Ser Val Asp Thr Ala Asp Thr Ala Thr Tyr Tyr
                 85                  90                  95

Cys Gly Arg Tyr Arg Tyr Gly Phe Ala Tyr Trp Gly Gln Gly Thr Leu
            100                 105                 110

Val Thr Val Ser
        115

<210> SEQ ID NO 106
<211> LENGTH: 348
<212> TYPE: DNA
<213> ORGANISM: Mus musculus

<400> SEQUENCE: 106
caggttactc tgaaagagtc tggccctggg atattgcagc cctcccagac cctcagtctg      60
acttgttctt tctctgggtt ttcactgagc acttctggta tgggtgtgag ctggattcgt     120
cagccttcag gagagggtct ggagtggctg gcacacattt actgggatga tgacaagcgc     180
tataacccat ccctgaagag ccggctcaca atctccaagg atacctccag aaaccaggta     240
ttcctcaaga tcaccagtgt ggacactgca gatactgcca catactactg tggtcgatat     300
aggtacggct tgcttactg gggccaaggg actctggtca ctgtctct                  348
```

<210> SEQ ID NO 107
<211> LENGTH: 112
<212> TYPE: PRT
<213> ORGANISM: Mus musculus

<400> SEQUENCE: 107

Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Ser Ile Val His Ser
            20                  25                  30

Asn Gly Asn Thr Tyr Leu Glu Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Val Pro Leu Thr Phe Gly Ala Gly Thr Lys Leu Glu Leu Lys
            100                 105                 110

<210> SEQ ID NO 108
<211> LENGTH: 336
<212> TYPE: DNA
<213> ORGANISM: Mus musculus

<400> SEQUENCE: 108
gatgttttga tgacccaaac tccactctcc ctgcctgtca gtcttggaga tcaagcctcc      60
atctcttgca gatctagtca gagcattgta catagtaatg aaacaccta tttagaatgg     120 tacctgcaga aaccaggcca gtctccaaag ctcctgatct acaaagtttc caaccgattt     180
tctggggtcc cagacaggtt cagtggcagt ggatcaggga cagatttcac actcaagatc     240
agcagagtgg aggctgagga tctgggagtt tattactgct ttcaaggttc acatgttccg     300
ctcacgttcg gtgctgggac caagctggag ctgaaa                               336

<210> SEQ ID NO 109
<211> LENGTH: 7
<212> TYPE: PRT
<213> ORGANISM: Mus musculus

<400> SEQUENCE: 109

Thr Ser Gly Met Gly Val Ser
1               5

<210> SEQ ID NO 110
<211> LENGTH: 21
<212> TYPE: DNA
<213> ORGANISM: Mus musculus

<400> SEQUENCE: 110
acttctggta tgggtgtgag c                                                21

<210> SEQ ID NO 111
<211> LENGTH: 9
<212> TYPE: PRT
<213> ORGANISM: Mus musculus

<400> SEQUENCE: 111

His Ile Tyr Trp Asp Asp Asp Lys Arg
1               5

```
<210> SEQ ID NO 112
<211> LENGTH: 27
<212> TYPE: DNA
<213> ORGANISM: Mus musculus

<400> SEQUENCE: 112
cacatttact gggatgatga caagcgc                                          27

<210> SEQ ID NO 113
<211> LENGTH: 7
<212> TYPE: PRT
<213> ORGANISM: Mus musculus

<400> SEQUENCE: 113

Tyr Arg Tyr Gly Phe Ala Tyr
1               5

<210> SEQ ID NO 114
<211> LENGTH: 21
<212> TYPE: DNA
<213> ORGANISM: Mus musculus

<400> SEQUENCE: 114
tataggtacg gctttgctta c                                                21

<210> SEQ ID NO 115
<211> LENGTH: 16
<212> TYPE: PRT
<213> ORGANISM: Mus musculus

<400> SEQUENCE: 115

Arg Ser Ser Gln Ser Ile Val His Ser Asn Gly Asn Thr Tyr Leu Glu
1               5                   10                  15

<210> SEQ ID NO 116
<211> LENGTH: 48
<212> TYPE: DNA
<213> ORGANISM: Mus musculus

<400> SEQUENCE: 116
agatctagtc agagcattgt acatagtaat ggaaacacct atttagaa                   48

<210> SEQ ID NO 117
<211> LENGTH: 7
<212> TYPE: PRT
<213> ORGANISM: Mus musculus

<400> SEQUENCE: 117

Lys Val Ser Asn Arg Phe Ser
1               5

<210> SEQ ID NO 118
<211> LENGTH: 21
<212> TYPE: DNA
<213> ORGANISM: Mus musculus

<400> SEQUENCE: 118
aaagtttcca accgattttc t                                                21

<210> SEQ ID NO 119
<211> LENGTH: 9
<212> TYPE: PRT
<213> ORGANISM: Mus musculus
```

```
<400> SEQUENCE: 119

Phe Gln Gly Ser His Val Pro Leu Thr
1               5

<210> SEQ ID NO 120
<211> LENGTH: 27
<212> TYPE: DNA
<213> ORGANISM: Mus musculus

<400> SEQUENCE: 120
tttcaaggtt cacatgttcc gctcacg                                         27
```